United States Patent
Sato et al.

(10) Patent No.: US 7,414,072 B2
(45) Date of Patent: Aug. 19, 2008

(54) ARYL 5-THIO-β-D-GLUCOPYRANOSIDE DERIVATIVES AND THERAPEUTIC AGENTS FOR DIABETES CONTAINING THE SAME

(75) Inventors: Masakazu Sato, Tokyo (JP); Hiroyuki Kakinuma, Tokyo (JP); Hajime Asanuma, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 244 days.

(21) Appl. No.: 10/518,788

(22) PCT Filed: Aug. 8, 2003

(86) PCT No.: PCT/JP03/10160

§ 371 (c)(1),
(2), (4) Date: Dec. 21, 2004

(87) PCT Pub. No.: WO2004/014931

PCT Pub. Date: Feb. 19, 2004

(65) Prior Publication Data

US 2005/0209309 A1    Sep. 22, 2005

(30) Foreign Application Priority Data

Aug. 9, 2002 (JP) .............................. 2002-233015
Apr. 1, 2003 (JP) .............................. 2003-097839

(51) Int. Cl.
*A01N 43/04*  (2006.01)
*A01N 43/18*  (2006.01)
*C07D 335/02* (2006.01)

(52) U.S. Cl. .................... 514/432; 514/23; 514/25; 514/42; 549/28; 536/4.1; 536/22.1

(58) Field of Classification Search ................ 549/28; 536/4.1, 22.1; 514/23, 25, 42
See application file for complete search history.

(56) References Cited

U.S. PATENT DOCUMENTS

2004/0063646 A1   4/2004   Fujikura et al.
2006/0194809 A1   8/2006   Kakinuma et al.

FOREIGN PATENT DOCUMENTS

| EP | 0850948  | A1 | 7/1998 |
|---|---|---|---|
| EP | 1213296  | A1 | 6/2002 |
| EP | 1272584  | A1 | 1/2003 |
| EP | 1338603  | A1 | 8/2003 |
| EP | 1 405 859 | A1 | 4/2004 |
| JP | 10-237089 | A | 9/1998 |
| WO | 01/16147 | A1 | 3/2001 |
| WO | 01/68660 | A1 | 9/2001 |
| WO | 01/74834 | A1 | 10/2001 |
| WO | 01/74835 | A1 | 10/2001 |
| WO | 02/36602 | A1 | 5/2002 |
| WO | 02/053573 | A1 | 7/2002 |
| WO | 03/000712 | A1 | 1/2003 |
| WO | 2004/089967 | A1 | 10/2004 |

OTHER PUBLICATIONS

Yuasa et al., Relative Nucleophilicity of the Two Sulfur Atoms in 1,5-Dithioglucopyranoside, Angewandte Chemie, Internation Edition in English, 36(8), pp. 868-870, 1997.*
Silverman et al., The organic Chemistry of Drug Design and Drug Action, pp. 19-23.*
Bozo, E., et al. "Synthesis of 4-cyanophenyl and 4-nitrophenyl 1,5-dithio-L- and -D-arabinopyranosides possessing antithrombotic activity[1,2]"., Carbohydrate Research, 1998, 311, pp. 191-202.
Randell, K.D., et al. Synthesis and glycosides inhibitory activity of 5-thioglucopyranosylamines. Molecular modeling of complexes with glucoamilase., Carbohydrate Research, 1999, 321, pp. 143-156.
Yuasa, H., et al. Relative Nucleophilicity of the Two Sulfur Atoms in 1,5-Dithioglucopyranoside., Angew. Chem. Int. Ed. Engl., 1997, 36, No. 8, pp. 868-870.
Supplementary European Search Report with mail date Apr. 2, 2007 for EP 03 78 4623.

* cited by examiner

*Primary Examiner*—Shaojia Anna Jiang
*Assistant Examiner*—Traviss C. McIntosh, III
(74) *Attorney, Agent, or Firm*—Sughrue Mion, PLLC

(57) ABSTRACT

There is provided a 5-thio-β-D-glucopyranoside compound of the following formula, which has an inhibitory effect on SGLT2 activity, or a pharmaceutically acceptable salt thereof or a hydrate thereof. There is also provided a pharmaceutical preparation, particularly a prophylactic or therapeutic agent for diabetes, diabetes-related diseases or diabetic complications, which comprises such a compound as an active ingredient.

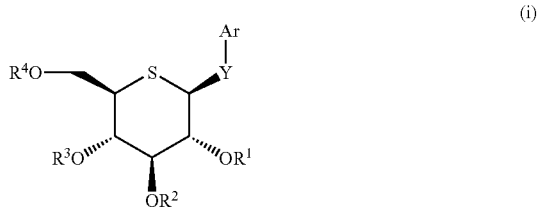

(i)

18 Claims, No Drawings

ARYL 5-THIO-β-D-GLUCOPYRANOSIDE DERIVATIVES AND THERAPEUTIC AGENTS FOR DIABETES CONTAINING THE SAME

This is a National Stage of Application No. PCT/JP03/10160 filed Aug. 8, 2003.

TECHNICAL FIELD

The present invention relates to 5-thio-β-D-glucopyranoside compounds capable of inhibiting the activity of sodium-dependent glucose transporter 2 (SGLT2), which is specifically present in the kidney and is involved in glucose reabsorption. The present invention also relates to pharmaceutical preparations, particularly therapeutic agents for diabetes, which comprise such a compound as an active ingredient.

BACKGROUND ART

Chronic hyperglycemia is believed to reduce both insulin secretion and insulin sensitivity, which in turn will cause elevation of blood glucose levels and lead to exacerbation of diabetes. Drugs conventionally used as therapeutic agents for diabetes include biguanides, sulfonylureas, glycosidase inhibitors and insulin-resistance improving agents. However, adverse side effects of these drugs have been reported; for example, lactic acidosis for biguanides, hypoglycemia for sulfonylureas, and diarrhea for glycosidase inhibitors. It is therefore desirable to develop therapeutic agents for diabetes that depend on a new mechanism of action which is different from those conventionally proposed.

Phloridzin, a glucose derivative isolated from nature, has been identified as having a hypoglycemic effect by inhibiting excessive glucose reabsorption in the kidney to accelerate the glucose excretion (J. Clin. Invest., vol. 80, p. 1037, 1987; J. Clin. Invest., vol. 87, p. 1510, 1987). There have been indications that this glucose reabsorption event is mediated by sodium-dependent glucose transporter 2 (SGLT2) present at the S1 site of renal proximal tubules (J. Clin. Invest., vol. 93, p. 397, 1994).

Under these backgrounds, an increasing number of studies have been conducted to develop therapeutic agents for diabetes that depend on SGLT2 inhibition, and a large number of phloridzin derivatives have been reported.

By way of example, there has been reported an aryl β-D-glucopyranoside compound having the following formula:

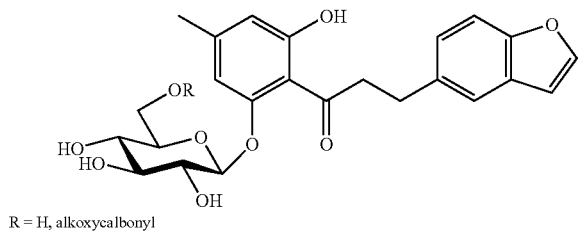

R = H, alkoxycalbonyl (European Patent Publication No. EP0850948). In addition to this, other relevant compounds have also been disclosed (International Patent Publication Nos. WO0168660, WO0116147, WO0174834, WO0174835, WO0253573, WO0268439, WO0268440, WO0236602, WO0288157, WO0228872, WO0244192, WO0264606, WO0311880, WO0320737, WO0300712, etc.).

When administered orally, phloridzin derivatives are hydrolyzed at glycosidic linkages by the action of glycosidase present in the small intestine, thus resulting in low absorption efficiency of unchanged form and a weak hypoglycemic effect. For this reason, various attempts have been made, for example, to increase absorption efficiency by administering phloridzin derivatives in the form of prodrugs and/or to prevent digestion by synthesizing compounds replaced by carbon-carbon linkages instead of glycosidic linkages (U.S. Pat. Nos. 20010041674, 2002137903 and 20031143, International Patent Publication No. WO0127128 and International Patent Publication No. WO0283066).

However, since no chemical synthesis technique has been developed for β-selective glycosylation of 5-thioglucose derivatives in which the ring oxygen atom of glucose is replaced by a sulfur atom, there is no report on 5-thio-β-D-glucopyranoside compounds. Thus, there is also no report on the SGLT2-inhibiting effect of 5-thio-β-D-glucopyranoside derivatives.

DISCLOSURE OF THE INVENTION

The object of the present invention is to provide novel compounds which have a hypoglycemic effect by inhibiting the activity of SGLT2 involved in glucose reabsorption in the kidney to accelerate excretion of urinary sugar.

As a result of extensive and intensive efforts made to overcome the problems stated above, the inventors of the present invention have found a method of enabling selective synthesis of 5-thio-β-D-glucopyranosides. Using this method, they also have synthesized aryl 5-thio-β-D-glucopyranoside derivatives or pharmaceutically acceptable salts thereof (hereinafter referred to as "the compound of the present invention") and have found that these compounds have an SGLT2-inhibiting effect. These findings led to the completion of the present invention.

Namely, the present invention is directed to a 5-thio-β-D-glucopyranoside compound of the following formula or a pharmaceutically acceptable salt thereof or a hydrate thereof:

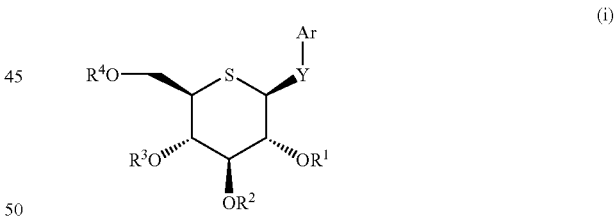

[wherein

Y represents —O— or —NH—, $R^1$, $R^2$, $R^3$ and $R^4$, which may be the same or different, each represent a hydrogen atom, a $C_{2-10}$ acyl group, a $C_{7-10}$ aralkyl group, a $C_{2-6}$ alkoxycarbonyl group, a $C_{1-6}$ alkoxy-$C_{2-10}$ acyl group or a $C_{1-6}$ alkoxy-$C_{2-6}$ alkoxycarbonyl group, Ar represents an aryl group substituted with —X-$A^1$, in which the aryl group may further be substituted with the same or different 1 to 4 substituents selected from:

a halogen atom;

a hydroxyl group;

a $C_{1-6}$ alkyl group which may be substituted with 1 to 4 substituents selected from the group consisting of a halogen atom and a hydroxyl group;

a group represented by the formula:

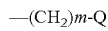—(CH$_2$)$m$-Q

{wherein m represents an integer of 0 to 4 and Q represents a formyl group, an amino group, a nitro group, a cyano group, a carboxyl group, a sulfonic acid group, a C$_{1-6}$ alkoxy group which may be substituted with 1 to 4 halogen atoms, a C$_{1-6}$ alkoxy-C$_{1-6}$ alkoxy group, a C$_{2-10}$ acyloxy group, a C$_{2-10}$ acyl group, a C$_{2-6}$ alkoxycarbonyl group, a C$_{1-6}$ alkylthio group, a C$_{1-6}$ alkylsulfinyl group, a C$_{1-6}$ alkylsulfonyl group, —NHC(=O)H, a C$_{2-10}$ acylamino group, a C$_{1-6}$ alkylsulfonylamino group, a C$_{1-6}$ alkylamino group, an N,N-di(C$_{1-6}$ alkyl)amino group, a carbamoyl group, an N—(C$_{1-6}$ alkyl)aminocarbonyl group, or an N,N-di(C$_{1-6}$ alkyl)aminocarbonyl group}; or a C$_{3-7}$ cycloalkyl group, a C$_{3-7}$ cycloalkyloxy group, an aryl group, a C$_{7-10}$ aralkyl group, an aryloxy group, a C$_{7-10}$ aralkyloxy group, a C$_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a C$_{1-6}$ alkyl group and a C$_{1-6}$ alkoxy group, X represents —(CH$_2$)n-, —CO(CH$_2$)n-, —CH(OH)(CH$_2$)n-, —O—(CH$_2$)n-, —CONH(CH$_2$)n-, —NHCO(CH$_2$)n- (wherein n represents an integer of 0 to 3), —COCH=CH—, —S— or —NH—, and A$^1$ represents an aryl group, a heteroaryl group or a 4- to 6-membered heterocycloalkyl group, each of which may be substituted with the same or different 1 to 4 substituents selected from:
 a halogen atom;
 a hydroxyl group;
 a C$_{1-6}$ alkyl group which may be substituted with 1 to 4 substituents selected from the group consisting of a halogen atom and a hydroxyl group;
 a group represented by the formula:

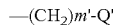—(CH$_2$)$m'$-Q'

{wherein m' represents an integer of 0 to 4 and Q' represents a formyl group, an amino group, a nitro group, a cyano group, a carboxyl group, a sulfonic acid group, a C$_{1-6}$ alkoxy group which may be substituted with 1 to 4 substituents selected from the group consisting of a halogen atom and a hydroxyl group, a C$_{1-6}$ alkoxy-C$_{1-6}$ alkoxy group, a C$_{2-10}$ acyloxy group, a C$_{2-10}$ acyl group, a C$_{2-6}$ alkoxycarbonyl group, a C$_{1-6}$ alkylthio group, a C$_{1-6}$ alkylsulfinyl group, a C$_{1-6}$ alkylsulfonyl group, —NHC(=O)H, a C$_{2-10}$ acylamino group, a C$_{1-6}$ alkylsulfonylamino group, a C$_{1-6}$ alkylamino group, an N,N-di(C$_{1-6}$ alkyl)amino group, a carbamoyl group, an N—(C$_{1-6}$ alkyl)aminocarbonyl group, or an N,N-di(C$_{1-6}$ alkyl)aminocarbonyl group}; or a C$_{3-7}$ cycloalkyl group, a C$_{3-7}$ cycloalkyloxy group, an aryl group, a C$_{7-10}$ aralkyl group, an aryloxy group, a C$_{7-10}$ aralkyloxy group, a C$_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a C$_{1-6}$ alkyl group and a C$_{1-6}$ alkoxy group].

BEST MODE FOR CARRYING OUT THE INVENTION

According to another embodiment of the present invention, there is provided a 5-thio-β-D-glucopyranoside compound of the following formula or a pharmaceutically acceptable salt thereof or a hydrate thereof:

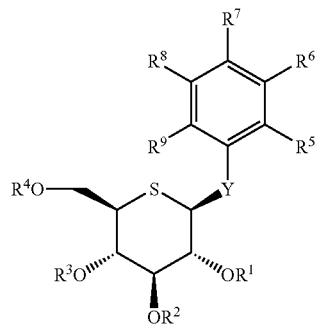

(I)

[wherein
 Y represents —O— or —NH—,
 R$^1$, R$^2$, R$^3$ and R$^4$, which may be the same or different, each represent a hydrogen atom, a C$_{2-10}$ acyl group, a C$_{7-10}$ aralkyl group, a C$_{2-6}$ alkoxycarbonyl group, a C$_{1-6}$ alkoxy-C$_{2-10}$ acyl group or a C$_{1-6}$ alkoxy-C$_{2-6}$ alkoxycarbonyl group, and
 at least one of R$^5$, R$^6$, R$^7$, R$^8$ and R$^9$ represents —X-A$^1$ (wherein X and A$^1$ are as defined above) and the other, which may be the same or different, each represent:
 a hydrogen atom;
 a halogen atom;
 a hydroxyl group;
 a C$_{1-6}$ alkyl group which may be substituted with 1 to 4 substituents selected from the group consisting of a halogen atom and a hydroxyl group;
 a group represented by the formula:

—(CH$_2$)$m$-Q (wherein m and Q are as defined above); or
 a C$_{3-7}$ cycloalkyl group, a C$_{3-7}$ cycloalkyloxy group, an aryl group, a C$_{7-10}$ aralkyl group, an aryloxy group, a C$_{7-10}$ aralkyloxy group, a C$_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a C$_{1-6}$ alkyl group and a C$_{1-6}$ alkoxy group].

According to another embodiment of the present invention, there is provided a 5-thio-β-D-glucopyranoside compound of the above formula wherein Y is —O—, or a pharmaceutically acceptable salt thereof or a hydrate thereof.

According to another embodiment of the present invention, there is provided a 5-thio-β-D-glucopyranoside compound of the above formula wherein R$^5$ is —X-A', or a pharmaceutically acceptable salt thereof or a hydrate thereof.

According to another embodiment of the present invention, there is provided a 5-thio-β-D-glucopyranoside compound of the above formula wherein X is —(CH$_2$)n- (wherein n represents an integer of 0 to 3), or a pharmaceutically acceptable salt thereof or a hydrate thereof.

According to another embodiment of the present invention, there is provided a 5-thio-β-D-glucopyranoside compound of the above formula wherein X is —CO(CH$_2$)n- (wherein n represents an integer of 0 to 3), or a pharmaceutically acceptable salt thereof or a hydrate thereof.

According to another embodiment of the present invention, there is provided a 5-thio-β-D-glucopyranoside compound of the following formula or a pharmaceutically acceptable salt thereof or a hydrate thereof:

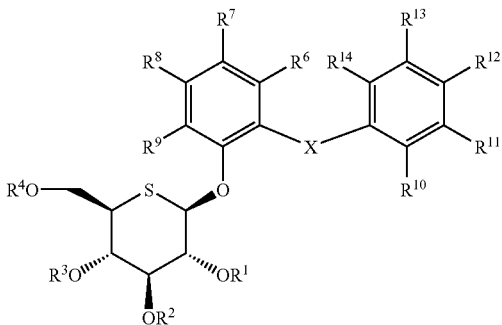

[wherein
X represents —(CH$_2$)n-, —CO(CH$_2$)n-, —CH(OH)(CH$_2$)n-, —O—(CH$_2$)n-, —CONH(CH$_2$)n-, —NHCO(CH$_2$)n- (wherein n represents an integer of 0 to 3), —COCH═CH—, —S— or —NH—, R$^1$, R$^2$, R$^3$ and R$^4$, which may be the same or different, each represent a hydrogen atom, a C$_{2-10}$ acyl group, a C$_{7-10}$ aralkyl group, a C$_{2-6}$ alkoxycarbonyl group, a C$_{1-6}$ alkoxy-C$_{2-10}$ acyl group or a C$_{1-6}$ alkoxy-C$_{2-6}$ alkoxycarbonyl group, R$^6$, R$^7$, R$^8$ and R$^9$, which may be the same or different, each represent:
a hydrogen atom;
a halogen atom;
a hydroxyl group;
a C$_{1-6}$ alkyl group which may be substituted with 1 to 4 substituents selected from the group consisting of a halogen atom and a hydroxyl group;
a group represented by the formula:

—(CH$_2$)m-Q

{wherein m represents an integer of 0 to 4 and Q represents a formyl group, an amino group, a nitro group, a cyano group, a carboxyl group, a sulfonic acid group, a C$_{1-6}$ alkoxy group which may be substituted with 1 to 4 halogen atoms, a C$_{1-6}$ alkoxy-C$_{1-6}$ alkoxy group, a C$_{2-10}$ acyloxy group, a C$_{2-10}$ acyl group, a C$_{2-6}$ alkoxycarbonyl group, a C$_{1-6}$ alkylthio group, a C$_{1-6}$ alkylsulfinyl group, a C$_{1-6}$ alkylsulfonyl group, —NHC(═O)H, a C$_{2-10}$ acylamino group, a C$_{1-6}$ alkylsulfonylamino group, a C$_{1-6}$ alkylamino group, an N,N-di(C$_{1-6}$ alkyl)amino group, a carbamoyl group, an N—(C$_{1-6}$ alkyl)aminocarbonyl group, or an N,N-di(C$_{1-6}$ alkyl)aminocarbonyl group}; or a C$_{3-7}$ cycloalkyl group, a C$_{3-7}$ cycloalkyloxy group, an aryl group, a C$_{7-10}$ aralkyl group, an aryloxy group, a C$_{7-10}$ aralkyloxy group, a C$_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a C$_{1-6}$ alkyl group and a C$_{1-6}$ alkoxy group, and R$^{10}$, R$^{11}$, R$^{12}$, R$^{13}$ and R$^{14}$, which may be the same or different, each represent:
a hydrogen atom;
a halogen atom;
a hydroxyl group;
a C$_{1-6}$ alkyl group which may be substituted with 1 to 4 substituents selected from the group consisting of a halogen atom and a hydroxyl group;

a group represented by the formula:

—(CH$_2$)m'-Q'

{wherein m' represents an integer of 0 to 4 and Q' represents a formyl group, an amino group, a nitro group, a cyano group, a carboxyl group, a sulfonic acid group, a C$_{1-6}$ alkoxy group which may be substituted with 1 to 4 halogen atoms, a C$_{1-6}$ alkoxy-C$_{1-6}$ alkoxy group, a C$_{2-10}$ acyloxy group, a C$_{2-10}$ acyl group, a C$_{2-6}$ alkoxycarbonyl group, a C$_{1-6}$ alkylthio group, a C$_{1-6}$ alkylsulfinyl group, a C$_{1-6}$ alkylsulfonyl group, —NHC(═O)H, a C$_{2-10}$ acylamino group, a C$_{1-6}$ alkylsulfonylamino group, a C$_{1-6}$ alkylamino group, an N,N-di(C$_{1-6}$ alkyl)amino group, a carbamoyl group, an N—(C$_{1-6}$ alkyl)aminocarbonyl group, or an N,N-di(C$_{1-6}$ alkyl)aminocarbonyl group}; or a C$_{3-7}$ cycloalkyl group, a C$_{3-7}$ cycloalkyloxy group, an aryl group, a C$_{7-10}$ aralkyl group, an aryloxy group, a C$_{7-10}$ aralkyloxy group, a C$_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a C$_{1-6}$ alkyl group and a C$_{1-6}$ alkoxy group].

According to another embodiment of the present invention, there is provided a 5-thio-β-D-glucopyranoside compound of Formula (II) wherein X is —CH$_2$—, or a pharmaceutically acceptable salt thereof or a hydrate thereof.

According to another embodiment of the present invention, there is provided a 5-thio-β-D-glucopyranoside compound of Formula (II) wherein X is —O— or —NH—, or a pharmaceutically acceptable salt thereof or a hydrate thereof.

According to another embodiment of the present invention, there is provided a 5-thio-β-D-glucopyranoside compound of the following formula or a pharmaceutically acceptable salt thereof:

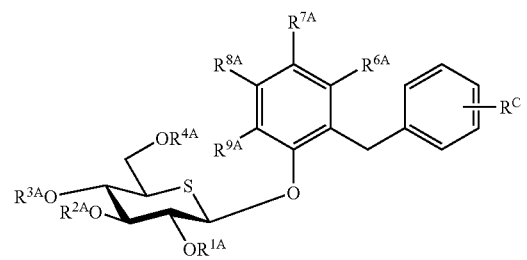

(A)

(wherein R$^{6A}$ to R$^{9A}$, which may be the same or different, each represent a hydrogen atom, a halogen atom, a C$_{1-6}$ alkyl group, a C$_{1-6}$ alkoxy group, a C$_{1-6}$ alkoxy-C$_{1-6}$ alkoxy group, a carboxyl group, a C$_{2-6}$ alkoxycarbonyl group, a hydroxyl group or a hydroxy-C$_{1-4}$ alkyl group, R$^C$ represents a hydrogen atom, a halogen atom, a C$_{1-6}$ alkyl group, a C$_{1-6}$ alkoxy group, a hydroxy-C$_{1-4}$ alkyl group, a halogen-substituted C$_{1-6}$ alkyl group or a C$_{1-6}$ alkylthio group, R$^{4A}$ represents a hydrogen atom, a C$_{2-6}$ alkoxycarbonyl group or a C$_{2-6}$ alkanoyl group, and R$^{1A}$ to R$^{3A}$, which may be the same or different, each represent a hydrogen atom, a C$_{2-8}$ alkanoyl group or a benzoyl group).

According to another embodiment of the present invention, there is provided a 5-thio-β-D-glucopyranoside compound of the following formula or a pharmaceutically acceptable salt thereof:

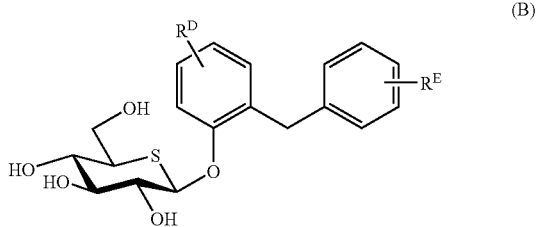

(B)

(wherein R^D represents a hydrogen atom, a halogen atom, a $C_{1-6}$ alkyl group or a hydroxy-$C_{1-4}$ alkyl group, and $R^E$ represents a hydrogen atom, a halogen atom, a $C_{1-6}$ alkyl group, a $C_{1-6}$ alkoxy group or a hydroxy-$C_{1-4}$ alkyl group).

According to another embodiment of the present invention, there is provided a 5-thio-β-D-glucopyranoside compound of the following formula or a pharmaceutically acceptable salt thereof or a hydrate thereof:

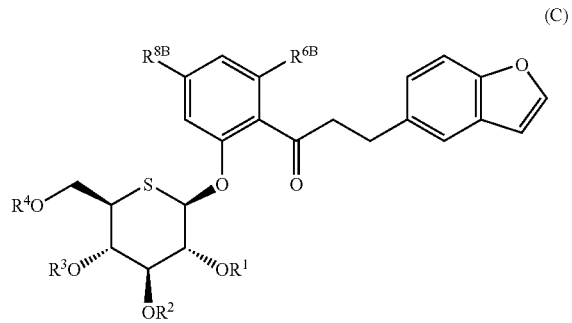

(C)

(wherein $R^1$, $R^2$, $R^3$ and $R^4$, which may be the same or different, each represent a hydrogen atom, a $C_{2-10}$ acyl group, a $C_{7-10}$ aralkyl group, a $C_{2-6}$ alkoxycarbonyl group, a $C_{1-6}$ alkoxy-$C_{2-10}$ acyl group or a $C_{1-6}$ alkoxy-$C_{2-6}$ alkoxycarbonyl group, $R^{6B}$ represents a hydrogen atom, a halogen atom, a hydroxyl group, a $C_{2-10}$ acyloxy group (preferably a $C_{2-4}$ alkanoyloxy group), or a $C_{1-6}$ alkyl or $C_{1-6}$ alkoxy group which may be substituted with 1 to 4 halogen atoms, and $R^{8B}$ represents a hydrogen atom, a halogen atom or a $C_{1-6}$ alkyl group which may be substituted with 1 to 4 halogen atoms).

According to another embodiment of the present invention, there is provided a pharmaceutical preparation, which comprises any one of the above 5-thio-β-D-glucopyranoside compounds or a pharmaceutically acceptable salt thereof or a hydrate thereof as an active ingredient.

According to another embodiment of the present invention, there is provided an inhibitor of sodium-dependent glucose transporter 2 (SGLT2) activity, which comprises any one of the above 5-thio-β-D-glucopyranoside compounds or a pharmaceutically acceptable salt thereof or a hydrate thereof as an active ingredient.

According to another embodiment of the present invention, there is provided a prophylactic or therapeutic agent for diabetes, diabetes-related diseases or diabetic complications, which comprises any one of the above 5-thio-β-D-glucopyranoside compounds or a pharmaceutically acceptable salt thereof or a hydrate thereof as an active ingredient.

According to another embodiment of the present invention, there is provided a pharmaceutical preparation, which comprises any one of the above 5-thio-β-D-glucopyranoside compounds or a pharmaceutically acceptable salt thereof or a hydrate thereof, in combination with at least one drug selected from the group consisting of an insulin sensitizer (which is selected from the group consisting of a PPARγ agonist, a PPARα/γ agonist, a PPARδ agonist and a PPARα/γ/δ agonist), a glycosidase inhibitor, a biguanide, an insulin secretagogue, an insulin formulation and a dipeptidyl peptidase IV inhibitor.

According to another embodiment of the present invention, there is provided a pharmaceutical preparation, which comprises any one of the above 5-thio-β-D-glucopyranoside compounds or a pharmaceutically acceptable salt thereof or a hydrate thereof, in combination with at least one drug selected from the group consisting of a hydroxymethylglutaryl coenzyme A reductase inhibitor, a fibrate, a squalene synthase inhibitor, an acyl-coenzyme A:cholesterol acyltransferase inhibitor, a low-density lipoprotein receptor promoter, a microsomal triglyceride transfer protein inhibitor and an anorectic.

Further, the present invention provides a 5-thio-β-D-glucopyranoside compound of the following formula, which is a synthetic intermediate for a compound of Formula (I), or a pharmaceutically acceptable salt thereof or a hydrate thereof:

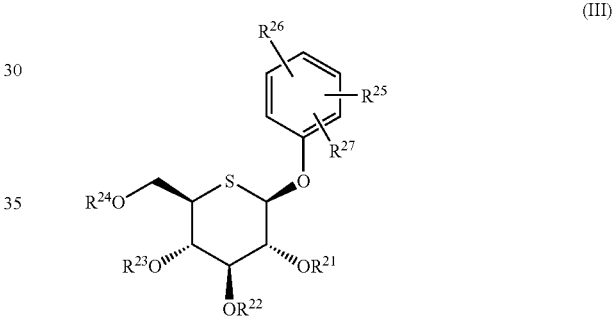

(III)

(wherein $R^{21}$, $R^{22}$, $R^{23}$ and $R^{24}$, which may be the same or different, each represent a hydrogen atom or a $C_{2-10}$ acyl group, $R^{25}$ represents an amino group, a $C_{2-6}$ alkanoyl group, a carboxyl group, a formyl group, a halogen atom, a $C_{2-6}$ alkoxycarbonyl group or a hydroxyl group, and $R^{26}$ and $R^{27}$, which may be the same or different, each represent a hydrogen atom, a halogen atom, a hydroxyl group, a $C_{1-6}$ alkyl group which may be substituted with 1 to 4 substituents selected from the group consisting of a halogen atom and a hydroxyl group, or a $C_{1-6}$ alkoxy group which may be substituted with 1 to 4 halogen atoms).

The terms and phrases used herein are defined as follows.

As used herein, the designation "$C_{x-y}$" is intended to mean a group containing x to y carbon atoms.

The term "$C_{2-10}$ acyl group" is intended to mean a linear or branched aliphatic acyl group (preferably a $C_{2-6}$ alkanoyl group) or an aromatic acyl group, which contains 2 to 10 carbon atoms. Examples include an acetyl group, a propionyl group, a pivaloyl group, a butyryl group, an isobutyryl group, a valeryl group and a benzoyl group, with an acetyl group being preferred.

The term "$C_{7-10}$ aralkyl group" refers to an aryl alkyl group containing 7 to 10 carbon atoms. Examples include a benzyl group and a phenylethyl group.

The term "$C_{1-6}$ alkoxy group" is intended to mean a linear or branched alkoxy group containing 1 to 6 carbon atoms. Preferred are $C_{1-4}$ alkoxy groups including a methoxy group, an ethoxy group, a propoxy group, an isopropoxy group, a n-butoxy group, an isobutoxy group and a tert-butoxy group.

The term "$C_{2-6}$ alkoxycarbonyl group" is intended to mean a structure composed of a linear or branched $C_{1-5}$ alkoxy group and a carbonyl group. Preferred are $C_{2-5}$ alkoxycarbonyl groups including a methoxycarbonyl group, an ethoxycarbonyl group, a propoxycarbonyl group, an isopropoxycarbonyl group and a butoxycarbonyl group. Among them, a methoxycarbonyl group is preferred.

The term "$C_{1-6}$ alkoxy-$C_{2-10}$ acyl group" is intended to mean a structure composed of a linear or branched $C_{1-6}$ alkoxy group and a $C_{2-10}$ acyl group. Preferred are a $C_{1-6}$ alkoxy-$C_{2-6}$ alkanoyl group and the like.

The term "$C_{1-6}$ alkoxy-$C_{2-6}$ alkoxycarbonyl group" is intended to mean a structure composed of a linear or branched $C_{1-6}$ alkoxy group and a $C_{2-6}$ alkoxycarbonyl group.

The term "halogen atom" encompasses a fluorine atom, a chlorine atom, a bromine atom, an iodine atom and the like.

The term "$C_{1-6}$ alkyl group" is intended to mean a linear or branched alkyl group containing 1 to 6 carbon atoms. Examples include a methyl group, an ethyl group, a n-propyl group, an isopropyl group, a n-butyl group, an isobutyl group, a tert-butyl group, a sec-butyl group, a n-pentyl group, a tert-amyl group, a 3-methylbutyl group and a neopentyl group.

The phrase "$C_{1-6}$ alkyl group substituted with 1 to 4 halogen atoms" refers to a $C_{1-6}$ alkyl group whose hydrogen atoms are replaced by 1 to 4 halogen atoms (preferably fluorine atoms). Examples include a trifluoromethyl group, a 1,1,1-trifluoroethyl group, a 1,1,1-trifluoropropyl group and a 1,1,1-trifluorobutyl group, with a trifluoromethyl group and a 1,1,1-trifluoroethyl group being preferred.

The phrase "$C_{1-6}$ alkyl group substituted with 1 to 4 hydroxyl groups" refers to an alkyl group whose hydrogen atoms are replaced by 1 to 4 hydroxyl groups. Preferred is a hydroxy-$C_{1-6}$ alkyl group (i.e., a $C_{1-6}$ alkyl group substituted with one hydroxyl group), and more preferred is a hydroxy-$C_{1-4}$ alkyl group. Examples include a hydroxymethyl group, a hydroxyethyl group (e.g., a 1-hydroxyethyl group), a hydroxypropyl group and a hydroxybutyl group.

The phrase "$C_{1-6}$ alkoxy group substituted with 1 to 4 halogen atoms" refers to an alkoxy group whose hydrogen atoms are replaced by halogen atoms. Examples include a trifluoromethoxy group, a 1,1,1-trifluoroethoxy group, a 1,1,1-trifluoropropoxy group and a 1,1,1-trifluorobutoxy group, with a trifluoromethoxy group and a 1,1,1-trifluoroethoxy group being preferred.

The term "$C_{1-6}$ alkoxy-$C_{1-6}$ alkoxy group" is intended to mean, for example, a methoxymethoxy group.

The term "$C_{2-10}$ acyloxy group" is intended to mean a structure composed of a $C_{2-10}$ acyl group and a —O— moiety. Preferred are a $C_{2-6}$ alkanoyloxy group (e.g., an acetyloxy group) and a benzoyloxy group.

The term "$C_{1-6}$ alkylthio group" is intended to mean a structure composed of a linear or branched $C_{1-6}$ alkyl group and one thio group (—S—), preferably refers to a $C_{1-4}$ alkylthio group. Examples of a $C_{1-6}$ alkylthio group include a methylthio group, an ethylthio group and a propylthio group.

The term "$C_{1-6}$ alkylsulfinyl group" is intended to mean a structure composed of a $C_{1-6}$ alkyl group and a sulfinyl group (—SO—). Preferred are a methanesulfinyl group and an ethanesulfinyl group.

The term "$C_{1-6}$ alkylsulfonyl group" is intended to mean a structure composed of a $C_{1-6}$ alkyl group and a sulfonyl group (—SO$_2$—). Preferred are a methanesulfonyl group and an ethanesulfonyl group.

The term "$C_{2-10}$ acylamino group" is intended to mean a structure composed of a $C_{2-10}$ acyl group and an amino group. Preferred is an acetylamino group.

The term "$C_{1-6}$ alkylsulfonylamino group" is intended to mean a structure composed of a $C_{1-6}$ alkylsulfonyl group and an amino group. Examples include a methanesulfonylamino group and an ethanesulfonylamino group.

The term "$C_{1-6}$ alkylamino group" is intended to mean a structure composed of a $C_{1-6}$ alkyl group and an amino group. Examples include a methylamino group and an ethylamino group.

The term "N,N-di($C_{1-6}$ alkyl)amino group" is intended to mean a structure composed of two $C_{1-6}$ alkyl groups and an amino group. Examples include a dimethylamino group and a diethylamino group.

The term "N—($C_{1-6}$ alkyl)aminocarbonyl group" is intended to mean a structure composed of an N—($C_{1-6}$ alkyl)amino group and a carbonyl group. Preferred are N—($C_{1-4}$ alkyl)aminocarbonyl groups including an N-methylaminocarbonyl group.

The term "N,N-di($C_{1-6}$ alkyl)aminocarbonyl group" is intended to mean a structure composed of an N,N-di($C_{1-6}$ alkyl)amino group and a carbonyl group. Preferred are N,N-di($C_{1-4}$ alkyl)aminocarbonyl groups including an N,N-dimethylaminocarbonyl group.

Examples of the groups —(CH$_2$)m-Q and —(CH$_2$)m'-Q' wherein m and m' each represent an integer of 1 or more will be provided below.

In a case where Q and Q' each represent a $C_{1-6}$ alkoxy group, examples include a methoxymethyl group.

In a case where Q and Q' each represent an amino group, examples include an aminomethyl group.

In a case where Q and Q' each represent a $C_{2-10}$ acyloxy group, examples include an acetyloxymethyl group and a benzoyloxyethyl group.

In a case where Q and Q' each represent a $C_{2-10}$ acylamino group, examples include an acetylaminomethyl group.

In a case where Q and Q' each represent an N,N-di($C_{1-6}$ alkyl)amino group, examples include an N,N-dimethylaminomethyl group.

The term "$C_{3-7}$ cycloalkyl group" is intended to mean a cyclic alkyl group containing 3 to 7 carbon atoms. Examples include a cyclopropyl group, a cyclobutyl group, a cyclopentyl group and a cyclohexyl group, with a cyclopropyl group being preferred.

The term "$C_{3-7}$ cycloalkyloxy group" is intended to mean a structure composed of a $C_{3-7}$ cycloalkyl group and a —O— moiety. Examples include a cyclopropyloxy group and a cyclopentyloxy group.

The term "aryl group" encompasses a phenyl group and a naphthyl group (including a 1-naphthyl group and a 2-naphthyl group), preferably refers to a phenyl group.

The term "aryloxy group" is intended to mean a structure composed of an aryl group and a —O— moiety. Examples include a phenoxy group and a naphthoxy group.

The term "$C_{7-10}$ aralkyloxy group" is intended to mean a structure composed of a $C_{7-10}$ aralkyl group and a —O— moiety. Examples include a benzyloxy group and a phenylethyloxy group.

The term "$C_{7-10}$ aralkylamino group" is intended to mean a structure composed of a $C_{7-10}$ aralkyl group and an —NH— moiety. Examples include a benzylamino group and a phenylethylamino group.

The term "heteroaryl group" encompasses a pyridyl group, a thiazolyl group, an isothiazolyl group, a thiadiazolyl group, a pyrazolyl group, an imidazolyl group, a furyl group (including a 2-furyl group and a 3-furyl group), a thienyl group (including a 2-thienyl group and a 3-thienyl group), an oxazolyl group, an isoxazolyl group, a pyrrolyl group (including a 1-pyrrolyl group, a 2-pyrrolyl group and a 3-pyrrolyl group, preferably a 1-pyrrolyl group), a triazolyl group, an isoxazolyl group, a pyrimidinyl group, a pyrazinyl group, a pyridazinyl group, a quinolinyl group, an isoquinolinyl group, a benzofuranyl group, a benzothiazolyl group and a benzothienyl group.

The term "4- to 6-membered heterocycloalkyl group" refers to a 4- to 6-membered heterocycloalkyl group containing at least one heteroatom (oxygen atom, nitrogen atom or sulfur atom) in the ring. For example, such a group may be a cyclic amino group that contains one or more nitrogen atoms in the ring and may further contain one or more oxygen atoms and/or sulfur atoms. Examples include a morpholino group, a piperidinyl group, a piperazinyl group and a 1-pyrrolidinyl group.

In relation to examples of a heteroaryl group substituted with 1 to 4 substituents, explanation will now be given of a case where the substituents are each a $C_{1-6}$ alkyl group.

A "thiazolyl group substituted with a $C_{1-6}$ alkyl group(s)" is intended to mean a thiazolyl group in which at least one hydrogen atom on the ring is replaced by a $C_{1-6}$ alkyl group, preferably by a $C_{1-4}$ alkyl group, and more preferably by a methyl group. Examples include a 4-methylthiazol-2-yl group.

A "pyridyl group substituted with a $C_{1-6}$ alkyl group(s)" is intended to mean a pyridyl group in which at least one hydrogen atom on the ring is replaced by a $C_{1-6}$ alkyl group, preferably by a $C_{1-4}$ alkyl group, and more preferably by a methyl group. Examples include a 2-methylpyridin-5-yl group.

A "pyrazolyl group substituted with a $C_{1-6}$ alkyl group(s)" is intended to mean a pyrazolyl group in which at least one hydrogen atom on the ring is replaced by a $C_{1-6}$ alkyl group, preferably by a $C_{1-4}$ alkyl group, and more preferably by a methyl group or an ethyl group. Examples include a 1-methylpyrazol-4-yl group and a 1-ethylpyrazol-4-yl group.

A "pyrrolyl group substituted with a $C_{1-6}$ alkyl group(s)" is intended to mean a pyrrolyl group in which at least one hydrogen atom on the ring is replaced by a $C_{1-6}$ alkyl group, preferably by a $C_{1-4}$ alkyl group, and more preferably by a methyl group. Examples include a 1-methylpyrrolyl group.

To mention examples of a heterocycloalkyl group substituted with 1 to 4 substituents, an explanation will be given of the case where the substituents are each a $C_{1-6}$ alkyl group.

A "4-$C_{1-6}$ alkylpiperazinyl group" is intended to mean a 1-piperazinyl group in which a hydrogen atom present on one nitrogen atom is replaced by a $C_{1-6}$ alkyl group. Examples include a 4-methylpiperazin-1-yl group and a 4-ethylpiperazin-1-yl group.

In addition, the term "pharmaceutically acceptable salt" is intended to mean, for example, a salt with an alkali metal, an alkaline earth metal, ammonium or an alkylammonium, or a salt with a mineral acid or an organic acid. Examples include a sodium salt, a potassium salt, a calcium salt, an ammonium salt, an aluminum salt, a triethylammonium salt, an acetate salt, a propionate salt, a butyrate salt, a formate salt, a trifluoroacetate salt, a maleate salt, a tartrate salt, a citrate salt, a stearate salt, a succinate salt, an ethylsuccinate salt, a lactobionate salt, a gluconate salt, a glucoheptate salt, a benzoate salt, a methanesulfonate salt, an ethanesulfonate salt, a 2-hydroxyethanesulfonate salt, a benzenesulfonate salt, a p-toluenesulfonate salt, a lauryl sulfate salt, a malate salt, an aspartate salt, a glutamate salt, an adipate salt, a salt with cysteine, a salt with N-acetylcysteine, a hydrochloride salt, a hydrobromide salt, a phosphate salt, a sulfate salt, a hydroiodide salt, a nicotinate salt, an oxalate salt, a picrate salt, a thiocyanate salt, an undecanoate salt, a salt with an acrylate polymer and a salt with a carboxyvinyl polymer.

Preferred embodiments for the compound of the present invention will be provided below.

Preferred examples of X are: —$(CH_2)$n- (wherein n is an integer of 0 to 3, preferably n=1), —$CO(CH_2)$n- (wherein n is an integer of 0 to 3, preferably n=2) and —$CONH(CH_2)$n- (wherein n is an integer of 0 to 3, preferably n=1).

More preferred as X is —$CH_2$—.

$R^6$, $R^7$, $R^8$ and $R^9$ in Formula (II) may be the same or different and each preferably represent:

a hydrogen atom;

a halogen atom;

a hydroxyl group;

a $C_{1-6}$ alkyl group which may be substituted with 1 to 4 substituents selected from the group consisting of a halogen atom and a hydroxyl group;

a group represented by the formula:

—$(CH_2)$m-Q

{wherein m represents an integer of 0 to 4 and Q represents an amino group, a cyano group, a carboxyl group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group (preferably a $C_{2-4}$ alkanoyloxy group), a $C_{2-10}$ acyl group, a $C_{2-6}$ alkoxycarbonyl group, a $C_{2-10}$ acylamino group, an N,N-di($C_{1-6}$ alkyl)amino group, or a carbamoyl group}; or a $C_{3-7}$ cycloalkyl group or a $C_{7-10}$ aralkyl group, each of which may be substituted with 1 to 4 substituents selected from the group consisting of a halogen atom, a hydroxyl group, a $C_{1-6}$ alkyl group and a $C_{1-6}$ alkoxy group.

More preferably, $R^6$ represents a hydrogen atom; a halogen atom; a hydroxyl group; a $C_{1-6}$ alkyl or $C_{1-6}$ alkoxy group which may be substituted with 1 to 4 halogen atoms; a $C_{2-4}$ alkanoyloxy group; or a $C_{3-7}$ cycloalkyl group which may be substituted with 1 to 4 substituents selected from the group consisting of a halogen atom, a hydroxyl group, a $C_{1-6}$ alkyl group and a $C_{1-6}$ alkoxy group. Even more preferably, $R^6$ represents a hydrogen atom; a halogen atom; or a hydroxyl group.

More preferably, $R^7$ represents a hydrogen atom; a halogen atom; a hydroxyl group; a $C_{1-6}$ alkyl group which may be substituted with 1 to 4 substituents selected from the group consisting of a halogen atom and a hydroxyl group; or a group represented by the formula:

—$(CH_2)$m-Q

{wherein m represents an integer of 0 to 4 and Q represents a carboxyl group, a $C_{1-6}$ alkoxy group which may be substituted with 1 to 4 halogen atoms, a $C_{2-10}$ acyloxy group, a $C_{2-10}$ acyl group, a $C_{2-6}$ alkoxycarbonyl group, or a carbamoyl group}. Even more preferably, $R^7$ represents a hydrogen atom; a halogen atom; a $C_{1-6}$ alkyl group which may be substituted with 1 to 4 substituents selected from the group consisting of a halogen atom and a hydroxyl group; a carboxyl group; or a $C_{2-6}$ alkoxycarbonyl group. Still more preferably, $R^7$ represents a hydrogen atom or a halogen atom.

More preferably, $R^8$ represents a hydrogen atom; a halogen atom; a hydroxyl group; a $C_{1-6}$ alkyl group which may be substituted with 1 to 4 substituents selected from the group consisting of a halogen atom and a hydroxyl group; or a group represented by the formula:

—(CH$_2$)$m$-Q

{wherein m represents an integer of 0 to 4 and Q represents an amino group, a cyano group, a carboxyl group, a C$_{1-6}$ alkoxy group which may be substituted with 1 to 4 halogen atoms, a C$_{1-6}$ alkoxy-C$_{1-6}$ alkoxy group, a C$_{2-10}$ acyloxy group, a C$_{2-10}$ acyl group, a C$_{2-6}$ alkoxycarbonyl group, a C$_{2-10}$ acylamino group, an N,N-di(C$_{1-6}$ alkyl)amino group, or a carbamoyl group}. Even more preferably, R$^8$ represents a hydrogen atom; a halogen atom; a hydroxyl group; a C$_{1-6}$ alkyl group which may be substituted with 1 to 4 substituents selected from the group consisting of a halogen atom and a hydroxyl group; or a group represented by the formula:

—(CH$_2$)$m$-Q

{wherein m represents an integer of 0 to 4 and Q represents a carboxyl group, a C$_{1-6}$ alkoxy-C$_{1-6}$ alkoxy group, a C$_{2-4}$ alkanoyloxy group, or a C$_{2-6}$ alkoxycarbonyl group}.

More preferably, R$^9$ represents a hydrogen atom; a halogen atom; a C$_{1-6}$ alkyl group which may be substituted with 1 to 4 halogen atoms; or a C$_{7-10}$ aralkyl group which may be substituted with 1 to 4 substituents selected from the group consisting of a halogen atom, a hydroxyl group, a C$_{1-6}$ alkyl group and a C$_{1-6}$ alkoxy group. Even more preferably, R$^9$ represents a hydrogen atom or a halogen atom.

R$^{10}$, R$^{11}$, R$^{12}$, R$^{13}$ and R$^{14}$ in Formula (II) may be the same or different and each preferably represent:

a hydrogen atom;

a halogen atom;

a hydroxyl group;

a C$_{1-6}$ alkyl group which may be substituted with 1 to 4 substituents selected from the group consisting of a halogen atom and a hydroxyl group;

a group represented by the formula:

—(CH$_2$)$m'$-Q'

{wherein m' represents an integer of 0 to 4 and Q' represents an amino group, a nitro group, a cyano group, a carboxyl group, a C$_{1-6}$ alkoxy group which may be substituted with 1 to 4 halogen atoms, a C$_{1-6}$ alkoxy-C$_{1-6}$ alkoxy group, a C$_{2-10}$ acyloxy group, a C$_{2-10}$ acyl group, a C$_{2-6}$ alkoxycarbonyl group, a C$_{1-6}$ alkylthio group, a C$_{1-6}$ alkylsulfinyl group, a C$_{1-6}$ alkylsulfonyl group, —NHC(=O)H, a C$_{2-10}$ acylamino group, a C$_{1-6}$ alkylsulfonylamino group, an N,N-di(C$_{1-6}$ alkyl)amino group, a carbamoyl group, or an N,N-di(C$_{1-6}$ alkyl) aminocarbonyl group); or a C$_{3-7}$ cycloalkyl group, a C$_{3-7}$ cycloalkyloxy group, an aryl group, a C$_{7-10}$ aralkyl group, an aryloxy group, a C$_{7-10}$ aralkyloxy group, a C$_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a C$_{1-6}$ alkyl group and a C$_{1-6}$ alkoxy group.

More preferably, only R$^{12}$ represents any substituent selected from the preferred examples listed above and the other symbols R$^{10}$, R$^{11}$, R$^{13}$ and R$^{14}$ each represent a hydrogen atom; a halogen atom; or a C$_{1-6}$ alkyl or C$_{1-6}$ alkoxy group which may be substituted with 1 to 4 halogen atoms.

Preferred compounds are any of those specifically listed below:

2'-(4'-ethylbenzyl)phenyl 5-thio-β-D-glucopyranoside (Compound 1);

4'-chloro-2'-(4'-ethylbenzyl)phenyl 5-thio-β-D-glucopyranoside (Compound 2);

2'-(4'-methylbenzyl)phenyl 5-thio-β-D-glucopyranoside (Compound 3);

2'-(4'-methoxybenzyl)phenyl 5-thio-β-D-glucopyranoside (Compound 4);

2'-(4'-ethoxybenzyl)phenyl 5-thio-β-D-glucopyranoside (Compound 5);

2'-(4'-trifluoromethylbenzyl)phenyl 5-thio-β-D-glucopyranoside (Compound 6);

2'-(4'-ethylbenzyl)-4'-methylphenyl 5-thio-β-D-glucopyranoside (Compound 7);

2'-(4'-ethylbenzyl)-4'-fluorophenyl 5-thio-β-D-glucopyranoside (Compound 8);

2'-(4'-fluorobenzyl)phenyl 5-thio-β-D-glucopyranoside (Compound 9);

4'-bromo-2'-(4'-ethylbenzyl)phenyl 5-thio-β-D-glucopyranoside (Compound 10);

2'-benzylphenyl 5-thio-β-D-glucopyranoside (Compound 11);

2'-(4'-ethylbenzyl)-4'-(hydroxymethyl)phenyl 5-thio-β-D-glucopyranoside (Compound 13);

2'-(4'-ethylbenzyl)-3'-hydroxyphenyl 5-thio-β-D-glucopyranoside (Compound 14);

2'-(4'-ethylbenzyl)-4'-methoxycarbonylphenyl 5-thio-β-D-glucopyranoside (Compound 15);

4'-carboxy-2'-(4'-ethylbenzyl)phenyl 5-thio-β-D-glucopyranoside (Compound 16);

4',6'-dibromo-2'-(4'-ethylbenzyl)phenyl 5-thio-β-D-glucopyranoside (Compound 17);

2'-(4'-hydroxybenzyl)phenyl 5-thio-β-D-glucopyranoside (Compound 18);

2'-(4'-hydroxyethylbenzyl)phenyl 5-thio-β-D-glucopyranoside (Compound 19);

2'-(4'-ethylbenzyl)-5'-(methoxymethyloxy)phenyl 5-thio-β-D-glucopyranoside (Compound 20);

2'-(4'-ethylbenzyl)-5'-hydroxyphenyl 5-thio-β-D-glucopyranoside (Compound 21);

2'-[3'-(benzofuran-5'-yl)-1'-oxopropyl]-3'-hydroxy-5'-methylphenyl 5-thio-β-D-glucopyranoside (Compound 22);

2'-(4'-ethylbenzyl)phenyl 6-O-methoxycarbonyl 5-thio-β-D-glucopyranoside (Compound 23); 1 4',6'-dichloro-2'-(4'-ethylbenzyl)phenyl 5-thio-β-D-glucopyranoside (Compound 31);

4',6'-difluoro-2'-(4'-ethylbenzyl)phenyl 5-thio-β-D-glucopyranoside (Compound 32);

2'-(4'-ethylbenzyl)-5'-(hydroxymethyl)phenyl 5-thio-β-D-glucopyranoside (Compound 39);

4'-chloro-2'-(4'-methoxycarbonylbenzyl)phenyl 5-thio-β-D-glucopyranoside (Compound 40);

4'-chloro-2'-(4'-nitrobenzyl)phenyl 5-thio-β-D-glucopyranoside (Compound 41);

2'-(4'-aminobenzyl)-4'-chlorophenyl 5-thio-β-D-glucopyranoside (Compound 42);

2'-(4'-pyrazol-1'-ylbenzyl)phenyl 5-thio-β-D-glucopyranoside (Compound 43);

4'-chloro-2'-(2'-fluorobenzyl)phenyl 5-thio-β-D-glucopyranoside (Compound 44);

2'-(4'-butoxybenzyl)-4'-chlorophenyl 5-thio-β-D-glucopyranoside (Compound 45);

2'-(4'-butylbenzyl)-4'-chlorophenyl 5-thio-β-D-glucopyranoside (Compound 46);

2'-(4'-acetylaminobenzyl)-4'-chlorophenyl 5-thio-β-D-glucopyranoside (Compound 47);

2'-(4'-ethylthiobenzyl)phenyl 5-thio-β-D-glucopyranoside (Compound 48);

4'-chloro-2'-(4'-methylsulfonylaminobenzyl)phenyl 5-thio-β-D-glucopyranoside (Compound 51);

4'-chloro-2'-(4'-N,N-dimethylaminobenzyl)phenyl 5-thio-β-D-glucopyranoside (Compound 52);

2'-(4'-hydroxymethylbenzyl)phenyl 5-thio-β-D-glucopyranoside (Compound 56);

2'-(2'-chloro-6'-fluorobenzyl)-4'-chlorophenyl 5-thio-β-D-glucopyranoside (Compound 59);

4'-chloro-2'-(2',4'-difluorobenzyl)phenyl 5-thio-β-D-glucopyranoside (Compound 60);

4'-chloro-2'-(3'-fluorobenzyl)phenyl 5-thio-β-D-glucopyranoside (Compound 61);

4'-chloro-2'-(4'-isopropylbenzyl)phenyl 5-thio-β-D-glucopyranoside (Compound 63);

2'-(4'-ethylbenzyl)-5'-fluorophenyl 5-thio-β-D-glucopyranoside (Compound 64);

2'-(2',4',6'-trimethoxybenzyl)phenyl 5-thio-β-D-glucopyranoside (Compound 65);

4'-chloro-2'-(2',3',5',6'-tetrafluorobenzyl)phenyl 5-thio-β-D-glucopyranoside (Compound 66);

4'-chloro-2'-(4'-phenylbenzyl)phenyl 5-thio-β-D-glucopyranoside (Compound 67);

4'-chloro-2'-(3'-trifluoromethoxybenzyl)phenyl 5-thio-β-D-glucopyranoside (Compound 69);

4'-chloro-2'-(2',4'-dichlorobenzyl)phenyl 5-thio-β-D-glucopyranoside (Compound 70);

4'-chloro-2'-(4'-pentyloxybenzyl)phenyl 5-thio-β-D-glucopyranoside (Compound 72);

2'-(4'-morpholinobenzyl)phenyl 5-thio-β-D-glucopyranoside (Compound 73);

2'-(4'-piperidinobenzyl)phenyl 5-thio-β-D-glucopyranoside (Compound 74);

2'-(4'-t-butylbenzyl)-4'-chlorophenyl 5-thio-β-D-glucopyranoside (Compound 75);

4'-chloro-2'-(3'-fluoro-5'-trifluoromethylbenzyl)phenyl 5-thio-β-D-glucopyranoside (Compound 76);

5'-(acetoxymethyl)-2'-(4'-ethylbenzyl)phenyl 5-thio-β-D-glucopyranoside (Compound 77);

4'-chloro-2'-(2',4'-dimethoxybenzyl)phenyl 5-thio-β-D-glucopyranoside (Compound 80);

4'-chloro-2'-(2'-ethoxybenzyl)phenyl 5-thio-β-D-glucopyranoside (Compound 81);

4'-chloro-2'-(2'-methylbenzyl)phenyl 5-thio-β-D-glucopyranoside (Compound 82);

2'-[4'-(4'-ethylpiperazin-1'-yl)benzyl]phenyl 5-thio-β-D-glucopyranoside (Compound 83);

3'-hydroxy-2'-(4'-methoxybenzylaminocarbonyl)phenyl 5-thio-β-D-glucopyranoside (Compound 84);

2'-(4'-carbamoylbenzyl)phenyl 5-thio-β-D-glucopyranoside (Compound 85);

2'-(4'-N,N-dimethylaminocarbonylbenzyl)phenyl 5-thio-β-D-glucopyranoside (Compound 86);

2'-(4'-acetylbenzyl)phenyl 5-thio-β-D-glucopyranoside (Compound 88);

2'-[4'-(1'-hydroxyethyl)benzyl]phenyl 5-thio-β-D-glucopyranoside (Compound 89);

2'-(4'-cyclopropylbenzyl)phenyl 5-thio-β-D-glucopyranoside (Compound 90); and

2'-(4'-cyanobenzyl)phenyl 5-thio-β-D-glucopyranoside (Compound 91).

More preferred are any of the compounds specifically listed below:

2'-(4'-ethylbenzyl)phenyl 5-thio-β-D-glucopyranoside (Compound 1);

4'-chloro-2'-(4'-ethylbenzyl)phenyl 5-thio-β-D-glucopyranoside (Compound 2);

2'-(4'-methylbenzyl)phenyl 5-thio-β-D-glucopyranoside (Compound 3);

2'-(4'-methoxybenzyl)phenyl 5-thio-β-D-glucopyranoside (Compound 4);

2'-(4'-ethoxybenzyl)phenyl 5-thio-β-D-glucopyranoside (Compound 5);

2'-(4'-trifluoromethylbenzyl)phenyl 5-thio-β-D-glucopyranoside (Compound 6);

2'-(4'-ethylbenzyl)-4'-methylphenyl 5-thio-β-D-glucopyranoside (Compound 7);

2'-(4'-ethylbenzyl)-4'-fluorophenyl 5-thio-β-D-glucopyranoside (Compound 8);

2'-(4'-fluorobenzyl)phenyl 5-thio-β-D-glucopyranoside (Compound 9);

4'-bromo-2'-(4'-ethylbenzyl)phenyl 5-thio-β-D-glucopyranoside (Compound 10);

2'-benzylphenyl 5-thio-β-D-glucopyranoside (Compound 11);

2'-(4'-hydroxybenzyl)phenyl 5-thio-β-D-glucopyranoside (Compound 18);

2'-(4'-hydroxyethylbenzyl)phenyl 5-thio-β-D-glucopyranoside (Compound 19);

2'-(4'-ethylbenzyl)-5'-(methoxymethyloxy)phenyl 5-thio-β-D-glucopyranoside (Compound 20);

2'-(4'-ethylbenzyl)-5'-hydroxyphenyl 5-thio-β-D-glucopyranoside (Compound 21);

2'-[3'-(benzofuran-5'-yl)-1'-oxopropyl]-3'-hydroxy-5'-methylphenyl 5-thio-β-D-glucopyranoside (Compound 22);

2'-(4'-ethylbenzyl)-5'-(hydroxymethyl)phenyl 5-thio-β-D-glucopyranoside (Compound 39);

2'-(4'-pyrazol-1'-ylbenzyl)phenyl 5-thio-β-D-glucopyranoside (Compound 43);

2'-(4'-ethylthiobenzyl)phenyl 5-thio-β-D-glucopyranoside (Compound 48);

5'-(acetoxymethyl)-2'-(4'-ethylbenzyl)phenyl 5-thio-β-D-glucopyranoside (Compound 77);

3'-hydroxy-2'-(4'-methoxybenzylaminocarbonyl)phenyl 5-thio-β-D-glucopyranoside (Compound 84);

2'-(4'-carbamoylbenzyl)phenyl 5-thio-β-D-glucopyranoside (Compound 85);

2'-(4'-N,N-dimethylaminocarbonylbenzyl)phenyl 5-thio-β-D-glucopyranoside (Compound 86);

2'-(4'-acetylbenzyl)phenyl 5-thio-β-D-glucopyranoside (Compound 88);

2'-[4'-(1'-hydroxyethyl)benzyl]phenyl 5-thio-β-D-glucopyranoside (Compound 89);

2'-(4'-cyclopropylbenzyl)phenyl 5-thio-β-D-glucopyranoside (Compound 90); and

2'-(4'-cyanobenzyl)phenyl 5-thio-β-D-glucopyranoside (Compound 91).

The compound of the present invention allows inhibition of sodium-dependent glucose transporter 2 (SGLT2) involved in glucose reabsorption in the kidney (J. Clin. Invest., vol. 93, p. 397, 1994).

Through inhibition of SGLT2, the compound of the present invention prevents sugar reabsorption and removes excess sugar from the body to thereby treat diabetes. Thus, the compound of the present invention corrects hyperglycemia without applying any load to pancreatic β cells, and improves insulin resistance.

Thus, the present invention provides a pharmaceutical preparation for preventing or treating diseases or conditions which can be ameliorated by inhibition of SGLT2 activity, e.g., diabetes, diabetes-related diseases and diabetic complications.

As used herein, the term "diabetes" encompasses type I diabetes, type II diabetes, and other types of diabetes with specific etiology.

As used herein, the term "diabetes-related diseases" includes adiposis, hyperinsulinemia, abnormal carbohydrate metabolism, hyperlipidemia, hypercholesterolemia, hypertriglyceridemia, abnormal lipid metabolism, hypertension, congestive heart failure, edema, hyperuricemia and gout.

As used herein, the term "diabetic complications" can be classified into acute complications and chronic complications.

The term "acute complications" includes hyperglycemia (e.g., ketoacidosis), infections (e.g., skin, soft tissue, biliary system, respiratory system and urinary tract infections), etc.

The term "chronic complications" includes microangiopathy (e.g., nephropathy, retinopathy), arteriosclerosis (e.g., atherosclerosis, heart infarction, brain infarction, lower extremity arterial occlusion), neuropathy (e.g., sensory nerves, motor nerves, autonomic nerves), foot gangrene, etc.

Major complications are diabetic retinopathy, diabetic nephropathy and diabetic neuropathy.

The compound of the present invention may also be used in combination with any therapeutic agent for diabetes, diabetic complications, hyperlipidemia or hypertension, which depends on a different mechanism of action other than inhibition of SGLT2 activity. When combined with other drugs, the compound of the present invention can be expected to produce an additive effect on these diseases, which is greater than either one alone.

Examples of a "therapeutic agent for diabetes or diabetic complications" available for combination use include, for example, insulin sensitizers (e.g., PPARγ agonists, PPARα/γ agonists, PPARδ agonists, PPARα/γ/δ agonists), glycosidase inhibitors, biguanides, insulin secretagogues, insulin formulations, glucagon receptor antagonists, insulin receptor kinase stimulators, tripeptidyl peptidase II inhibitors, dipeptidyl peptidase IV inhibitors, protein tyrosine phosphatase-1B inhibitors, glycogen phosphorylase inhibitors, glucose-6-phosphatase inhibitors, gluconeogenesis inhibitors, fructose-bisphosphatase inhibitors, pyruvate dehydrogenase inhibitors, glucokinase activators, D-chiroinositol, glycogen synthase kinase-3 inhibitors, glucagon-like peptide-1, glucagon-like peptide-1 analogs, glucagon-like peptide-1 agonists, amylin, amylin analogs, amylin agonists, glucocorticoid receptor antagonists, 11β-hydroxysteroiddehydrogenase inhibitors, aldose reductase inhibitors, protein kinase C inhibitors, γ-aminobutyric acid receptor antagonists, sodium channel antagonists, transcription factor NF-κB inhibitors, IKKβ inhibitors, lipid peroxidase inhibitors, N-acetylated-α-linked-acid-dipeptidase inhibitors, insulin-like growth factor-I, platelet-derived growth factors (PDGF), platelet-derived growth factor (PDGF) analogs, epidermal growth factors (EGF), nerve growth factors, carnitine derivatives, uridine, 5-hydroxy-1-methylhydantoin, EGB-761, bimoclomol, sulodexide, Y-128 and TAK-428.

Illustrative examples of a therapeutic agent for diabetes or diabetic complications are as follows.

"Biguanides" include metformin hydrochloride and phenformin.

"Insulin secretion stimulators" include those of the sulfonylurea type such as glyburide (glibenclamide), glypizide, gliclazide and chlorpropamide, as well as those of the non-sulfonylurea type such as nateglinide, repaglinide and mitiglinide.

"Insulin formulations" encompass both recombinantly produced human insulin and animal-derived insulin. Such formulations can be divided into three groups depending on the length of their duration: fast-acting formulations (e.g., human insulin, human neutral insulin); intermediate-acting formulations (e.g., insulin-human isophane insulin aqueous suspension, human neutral insulin-human isophane insulin aqueous suspension, human insulin zinc aqueous suspension, insulin zinc aqueous suspension); and long-acting formulations (e.g., human crystalline insulin zinc suspension).

"Glycosidase inhibitors" include acarbose, voglibose and miglitol.

"Insulin sensitivity enhancers" include PPARγ agonists such as troglitazone, pioglitazone and rosiglitazone, PPARα/γ dual agonists such as MK-767 (KRP-297), tesaglitazar, LM4156, LY510929, DRF-4823 and TY-51501, as well as PPARδ agonists such as GW-501516.

"Tripeptidyl peptidase II inhibitors" include UCL-139.

"Dipeptidyl peptidase IV inhibitors" include NVP-DPP728A, LAF-237, P32/98 and TSL-225.

"Aldose reductase inhibitors" include ascorbyl gamolenate, tolrestat, epalrestat, fidarestat, sorbinil, ponalrestat, risarestat and zenarestat.

"γ-Aminobutyric acid receptor antagonists" include topiramate.

"Sodium channel antagonists" include mexiletine hydrochloride.

"Transcription factor NF-κB inhibitors" include dexlipotam.

"Lipid peroxidase inhibitors" include tirilazad mesylate.

"N-Acetylated-α-linked-acid-dipeptidase inhibitors" include GPI-5693.

"Carnitine derivatives" include carnitine and levacecamine hydrochloride.

Examples of a "therapeutic agent for hyperlipidemia or hypertension" available for combination use include, for example, hydroxymethylglutaryl coenzyme A reductase inhibitors, fibrates, β$_3$-adrenergic receptor agonists, AMPK activators, acyl-coenzyme A:cholesterol acyltransferase inhibitors, probucol, thyroid hormone receptor agonists, cholesterol absorption inhibitors, lipase inhibitors, microsomal triglyceride transfer protein inhibitors, lipoxygenase inhibitors, carnitine palmitoyl transferase inhibitors, squalene synthase inhibitors, low-density lipoprotein receptor promoters, nicotinic acid derivatives, bile acid binding resins, sodium-dependent bile acid transporter inhibitors, cholesterol ester transport protein inhibitors, angiotensin-converting enzyme inhibitors, angiotensin II receptor antagonists, endothelin-converting enzyme inhibitors, endothelin receptor antagonists, diuretics, calcium antagonists, vasodilator antihypertensives, sympatholytic agents, central-acting antihypertensives, α$_2$-adrenergic receptor agonists, antiplatelet agents, uric acid production inhibitors, uric acid excretion stimulators, urine alkalizers, anorectics, AGE inhibitors, adiponectin receptor agonists, GPR40 agonists and GPR40 antagonists.

Illustrative examples of a therapeutic agent for hyperlipidemia or hypertension are as follows.

"Hydroxymethylglutaryl coenzyme A reductase inhibitors" include fluvastatin, lovastatin, pravastatin, cerivastatin and pitavastatin.

"Fibrates" include bezafibrate, beclobrate and binifibrate.

"Squalene synthase inhibitors" include TAK-475 and α-phosphonosulfonate derivatives (U.S. Pat. No. 5,712,396).

"Acyl-coenzyme A: cholesterol acyltransferase inhibitors" include CI-1011, NTE-122, FCE-27677, RP-73163, MCC-147 and DPU-129.

"Low-density lipoprotein receptor promoters" include MD-700 and LY-295427.

"Microsomal triglyceride transfer protein inhibitors (MTP inhibitors)" include compounds as described in, e.g., U.S. Pat. No. 5,739,135, U.S. Pat. No. 5,712,279 and U.S. Pat. No. 5,760,246.

"Anorectics" include adrenaline/noradrenaline agonists (e.g., mazindol, ephedrine), serotonin agonists (selective serotonin reuptake inhibitors such as fluvoxamine), adrenaline/serotonin agonists (e.g., sibutramine), melanocortin 4 receptor (MC4R) agonists, α-melanocyte-concentrating hormones (α-MCH), leptin, as well as cocaine- and amphetamine-regulated transcripts (CART).

"Thyroid hormone receptor agonists" include liothyronine sodium and levothyroxine sodium.

"Cholesterol absorption inhibitors" include ezetimibe.

"Lipase inhibitors" include orlistat.

"Carnitine palmitoyl transferase inhibitors" include etomoxir.

"Nicotinic acid derivatives" include nicotinic acid, nicotinamide, nicomol and nicorandil.

"Bile acid binding resins" include cholestyramine, colestilan and colesevelam hydrochloride.

"Angiotensin-converting enzyme inhibitors" include captoril, enalapril maleate, alacepril and cilazapril.

"Angiotensin II receptor antagonists" include candesartan cilexetil, losartan potassium and eprosartan mesylate.

"Endothelin-converting enzyme inhibitors" include CGS-31447 and CGS-35066.

"Endothelin receptor antagonists" include L-749805, TBC-3214 and BMS-182874.

By way of example, in treating diabetes or the like, it would be preferable to use the compound of the present invention in combination with at least one drug selected from the group consisting of an insulin sensitizer (e.g., a PPARγ agonist, a PPARα/γ agonist, a PPARδ agonist, a PPARα/γ/δ agonist), a glycosidase inhibitor, a biguanide, an insulin secretagogue, an insulin formulation and a dipeptidyl peptidase IV inhibitor.

Alternatively, it would be preferable to use the compound of the present invention in combination with at least one drug selected from the group consisting of a hydroxymethylglutaryl coenzyme A reductase inhibitor, a fibrate compound, a squalene synthase inhibitor, an acyl-coenzyme A:cholesterol acyltransferase inhibitor, a low-density lipoprotein receptor promoter, a microsomal triglyceride transfer protein inhibitor and an anorectic.

The pharmaceutical preparation of the present invention can be administered systemically or topically via oral route or parenteral (e.g., intrarectal, subcutaneous, intramuscular, intravenous, percutaneous) route.

For use as a pharmaceutical preparation, the compound of the present invention may be formulated into any desired dosage form selected from solid compositions, liquid compositions and other compositions, as appropriate for the intended purpose. The pharmaceutical preparation of the present invention can be prepared by blending the compound of the present invention with pharmaceutically acceptable carrier(s). More specifically, the compound of the present invention may be supplemented with commonly used excipients, extenders, binders, disintegrating agents, coating agents, sugar-coating agents, pH regulators, solubilizers, aqueous or non-aqueous solvents and so on, and then formulated using standard techniques into tablets, pills, capsules, granules, powders, solutions, emulsions, suspensions, injections, etc. Examples of excipients and extenders include, for example, lactose, magnesium stearate, starch, talc, gelatin, agar, pectin, gum arabic, olive oil, sesame oil, cacao butter, ethylene glycol and other commonly used materials.

Also, the compound of the present invention may be modified to form an inclusion compound with, e.g., α-, β- or γ-cyclodextrin or methylated cyclodextrin before being formulated.

The dose of the compound of present invention will vary depending on the disease or symptom to be treated, body weight, age, sex, the route of administration, etc. The adult dose is preferably 0.1 to 1000 mg/kg body weight/day, more preferably 0.1 to 200 mg/kg body weight/day, given as a single dose or in divided doses.

The compound of the present invention can be synthesized, for example, as shown in the production schemes below.

A key intermediate 5-thio-D-glucopyranose (VII) can be prepared as follows, by way of example.

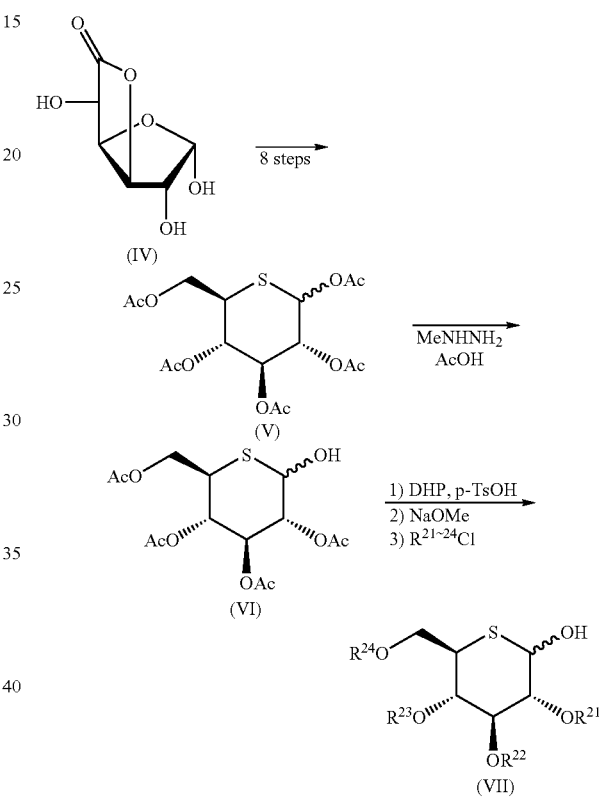

Scheme 1

The penta-O-acetate derivative (V) (Tetrahedron Lett., vol. 22, p. 5061, 1981; J. Org. Chem., vol. 31, p. 1514, 1966) can be synthesized via 8 steps from D-glucofurano-3,6-lactone (IV).

Next, Compound (V) may be treated in an appropriate solvent (e.g., DMF, THF, methanol, ethanol) using hydrazine acetate (Tetrahedron, Lett., vol. 33, p. 7675, 1992) or benzylamine, preferably a 1:1 mixture of methylhydrazine and acetic acid, to effect selective deprotection of the 1-position acetyl group, thereby preparing Compound (VI). The reaction temperature ranges from room temperature to 80° C., while the reaction time ranges from 20 minutes to 24 hours.

After the 1-position hydroxyl group of Compound (VI) is protected (e.g., with a tetrahydropyranyl group), the compound may be deprotected to remove the acetyl groups and treated with a $C_{2-10}$ acyl chloride (e.g., a $C_{2-6}$ alkanoyl chloride or benzoyl chloride) under basic conditions, thereby giving the 5-thio-D-glucopyranose derivative (VII) {wherein $R^{21}$, $R^{22}$, $R^{23}$ and $R^{24}$, which may be the same or different, each represent a $C_{2-10}$ acyl group (e.g., a $C_{2-6}$ alkanoyl group or a benzoyl group)} (Chem. Lett., p. 626, 2002).

With respect to the intermediate Ar—YH corresponding to the aglycon, a compound of the following formula:

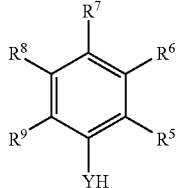

(VIII)

(wherein $R^5$, $R^6$, $R^7$, $R^8$, $R^9$ and Y are as defined above), which is an intermediate for the compound of Formula (I), can be synthesized by reference to the following official gazettes: International Patent Publication Nos. WO0168660, WO0174834, WO0174835, WO0228872, WO0244192, WO0264606 and WO0311880.

In the case of an intermediate for the compound of Formula (II) wherein X is —$CH_2$—, for example, phenol (IX) may be condensed with benzyl alcohol (X) under acidic conditions to prepare Compound (XI).

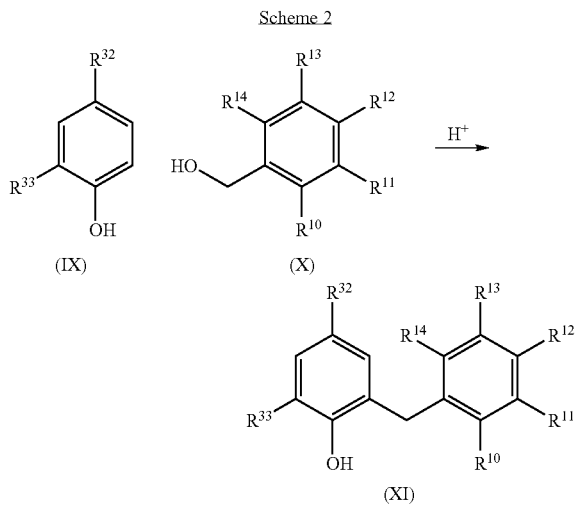

Scheme 2

(wherein $R^{32}$ and $R^{33}$, which may be the same or different, each represent a hydrogen atom, a halogen atom or a $C_{1-6}$ alkyl group, and $R^{10}$, $R^{11}$, $R^{12}$, $R^{13}$ and $R^{14}$ are as defined above.)

An acid available for use in the condensation may be, for example, methanesulfonic acid or p-toluenesulfonic acid. If a solvent is used, a high-boiling solvent such as nitrobenzene is preferred. The reaction temperature ranges from 100° C. to 200° C., while the reaction time ranges from 10 minutes to 150 minutes.

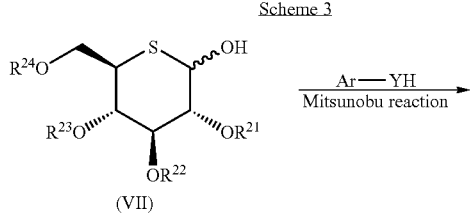

Scheme 3

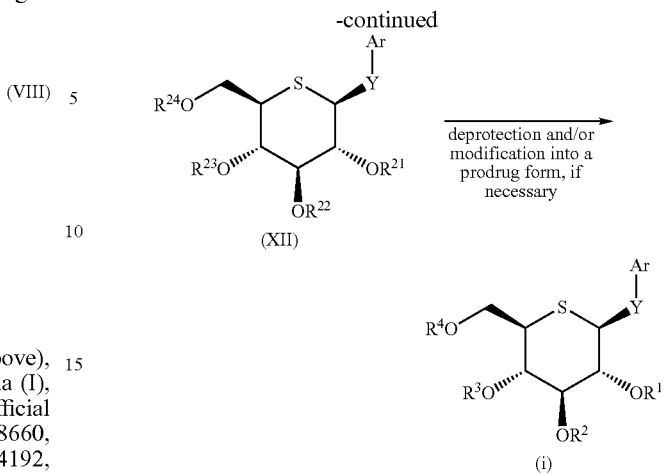

(XII)

(i)

(wherein the wavy line means containing any stereoisomer selected from D-form, L-form and a mixture thereof, and each substituent is as defined above.)

Next, the 5-thio-D-glucopyranose derivative (VI) or (VII) may be condensed with Ar—YH under Mitsunobu reaction conditions using an azo reagent and phosphines (Org. Reactions, vol. 42, p. 335) to prepare Compound (XII).

Solvents available for use in the Mitsunobu reaction include tetrahydrofuran, dioxane, toluene, methylene chloride, chloroform, acetonitrile, ethyl acetate, dimethyl sulfoxide and N,N-dimethylformamide. Preferred are tetrahydrofuran and toluene, and more preferred is toluene. Phosphines available for use include triphenylphosphine, tri-n-butylphosphine, tri-t-butylphosphine, tritolylphosphine and diphenyl-2-pyridylphosphine. Among them, preferred are triphenylphosphine and diphenyl-2-pyridylphosphine, and more preferred is triphenylphosphine. Azo reagents available for use include diethyl azodicarboxylate, diisopropyl azodicarboxylate and di-tert-butyl azodicarboxylate, as well as 1,1'-azobis(N,N-dimethylformamide) and 1,1'-(azodicarbonyl)dipiperidine. Among them, preferred are diethyl azodicarboxylate and diisopropyl azodicarboxylate. The reaction temperature preferably ranges from –20° C. to room temperature.

If necessary, Compound (XII) may further be deprotected to remove the protecting groups of sugar hydroxyl groups and/or optionally modified into a prodrug form, thus obtaining Compound (i) according to the present invention.

The deprotection may be accomplished by using a base such as sodium methoxide, sodium hydroxide, lithium hydroxide, potassium carbonate, cesium carbonate or triethylamine. Solvents suitable for the reaction include methanol, ethanol and aqueous methanol.

Likewise, the modification into a prodrug form may be accomplished by using any protective agent for hydroxyl groups well known to those skilled in the art (e.g., acid anhydrides, chloroformate esters) to convert —$OR^{21}$ to —$OR^{24}$ (wherein $R^{21}$ to $R^{24}$ are as defined above) into —$OR^1$ to —$OR^4$ (wherein $R^1$ to $R^4$ each represent a group constituting a prodrug). Solvents suitable for the above reaction include collidine, pyridine and N,N-dimethylformamide.

Examples of a "group constituting a prodrug" include protecting groups for hydroxyl groups which can be commonly used in prodrugs, such as a $C_{2-11}$ acyl group (e.g., a $C_{2-8}$ alkanoyl group (preferably a $C_{2-6}$ alkanoyl group) or a benzoyl group), a $C_{2-6}$ alkoxycarbonyl group, a $C_{1-6}$ alkoxy-$C_{2-10}$ acyl group (preferably a $C_{1-6}$ alkoxy-$C_{2-6}$ alkanoyl group) and a $C_{1-6}$ alkoxy-$C_{2-6}$ alkoxycarbonyl group.

Alternatively, when controlling the reaction conditions, only —OR$^{24}$ can be selectively reacted and converted into —OR$^{4}$. In this case, preferred as R$^{4}$ is a C$_{2-6}$ alkanoyl group, a C$_{2-6}$ alkoxycarbonyl group or the like.

Alternatively, Compound (XV) according to the present invention can be prepared as follows.

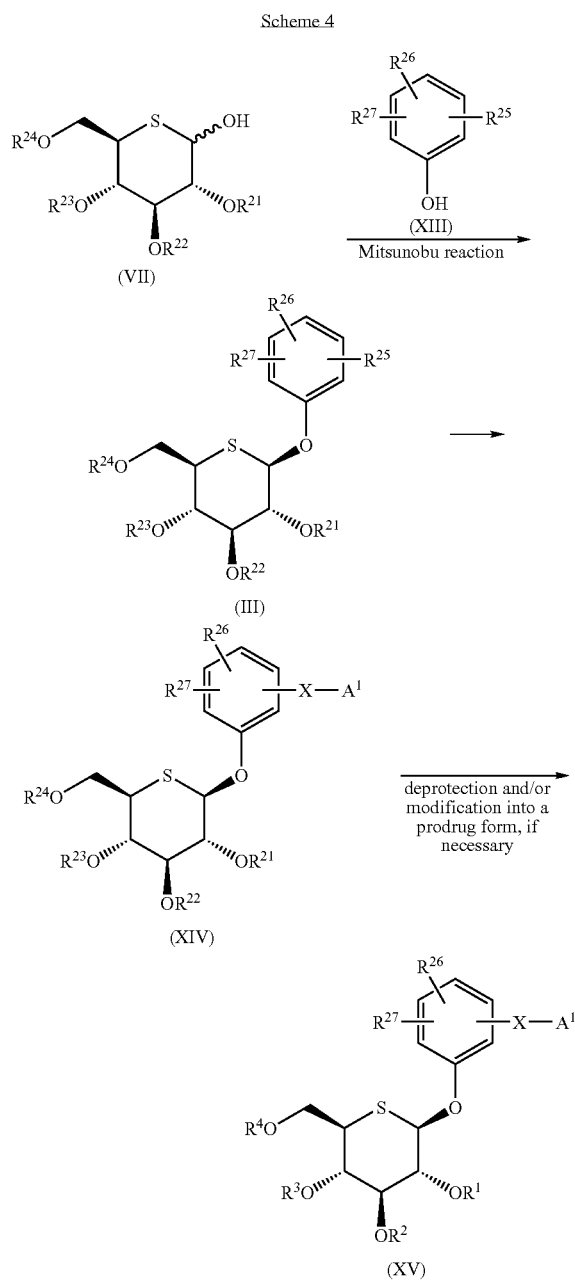

(wherein R$^{1}$ to R$^{4}$, R$^{21}$ to R$^{27}$, X and A$^{1}$ are as defined above.)

Compound (VII) may be condensed with Compound (XIII) through Mitsunobu reaction to prepare Compound (III). Next, the moiety X-A$^{1}$ may be constructed through Suzuki coupling reaction, Stille coupling reaction, dehydration condensation, aldol condensation or the like, thereby preparing Compound (XIV).

For example, in a case where R$^{25}$ is an amino group, a hydroxyl group or a halogen atom, these groups may be coupled with an optionally substituted arylboric acid (e.g., phenylboric acid) or an optionally substituted heteroarylboric acid in the presence of a palladium catalyst (e.g., Pd$_2$(OAc)$_2$, Pd(dba)$_2$, dba:dibenzyliden acetone, Pd(PPh$_3$)$_4$) or a copper catalyst (e.g., Cu(OAc)$_2$) to prepare a derivative in which A$^{1}$ is an optionally substituted aryl or heteroaryl group and X is —NH—, —O— or a single bond. In this reaction, a copper catalyst such as Cu(OAc)$_2$ is preferred.

Alternatively, in a case where R$^{25}$ is a halogen atom, this group may be coupled with an optionally substituted aryltributyltin (e.g., phenyltributyltin) or an optionally substituted heteroaryltributyltin in the presence of a palladium catalyst (e.g., Pd$_2$(OAc)$_2$, Pd(dba)$_2$, Pd(PPh$_3$)$_4$) to prepare a derivative in which A$^{1}$ is an optionally substituted aryl or heteroaryl group and X is a single bond.

Alternatively, in a case where R$^{25}$ is a C$_{2-6}$ alkanoyl group, this group may be subjected to aldol condensation with A$^{1}$-CHO (wherein A$^{1}$ is as defined above) (e.g., formylbenzofuran). Alternatively, in a case where R$^{25}$ is a formyl group, this group may be treated with A$^{1}$-MgBr or A$^{1}$Li to prepare a synthetic intermediate in which X is —CHOH—.

Alternatively, in a case where R$^{25}$ is an amino group or a carboxyl group, these groups may be condensed with A$^{1}$-(CH$_2$)$_n$CO$_2$H or A$^{1}$-(CH$_2$)$_n$NH$_2$ (wherein n represents an integer of 0 to 3) in the presence of a dehydration condensing agent (e.g., N,N-dicyclohexylcarbodiimide (DCC), water-soluble carbodiimide hydrochloride (WSCHCl), carbonyldiimidazole (CDI)} to prepare a compound in which X is —NHCO(CH$_2$)n- or —CONH(CH$_2$)n- (wherein n represents an integer of 0 to 3).

If necessary, Compound (XIV) may further be deprotected to remove the protecting groups of sugar hydroxyl groups and/or optionally modified into a prodrug form, thus obtaining Compound (XV) according to the present invention.

REFERENCE EXAMPLES

Preparation of intermediates required to prepare the compounds of the present invention will be illustrated below with reference to the following Reference Examples 1 to 11.

Reference Example 1

Preparation of 4-chloro-2-(4-ethylbenzyl)phenol

A mixture of 4-chlorophenol (2.0 g, 15.6 mmol), 4-ethylbenzylalcohol (2.12 g, 15.6 mmol) and methanesulfonic acid (80 mg, 0.83 mmol) was heated and stirred at 160° C. for 25 minutes. The reaction mixture was purified by silica gel column chromatography (hexane:ethyl acetate=9:1) to give 4-chloro-2-(4-ethylbenzyl)phenol (1.78 g, 46%) as a light-yellow oil.

Reference Example 2

Preparation of 4-bromo-2-(4-ethylbenzyl)phenol

The same procedure as shown in Reference Example 1 was repeated to give 4-bromo-2-(4-ethylbenzyl)phenol (35%) as a brown oil.

Reference Example 3

Preparation of 2,4-dibromo-6-(4-ethylbenzyl)phenol

The same procedure as shown in Reference Example 1 was repeated to give 2,4-dibromo-6-(4-ethylbenzyl)phenol (46%) as a colorless powder.

mp 90.0-91.5° C.

Alternatively, to a mixture of 2-(4-ethylbenzyl)phenol (1.01 g, 4.76 mmol) and DMF (5 mL), a solution of N-bromosuccinimide (1.86 g, 10.5 mmol) in DMF (5 mL) was added dropwise in ice. After 1 hour, the reaction mixture was diluted with ethyl acetate, washed with saturated aqueous sodium chloride and saturated $Na_2S_2O_3$ solution, and then dried over anhydrous magnesium sulfate. After the solvent was distilled off under reduced pressure, the resulting residue was purified by silica gel column chromatography (hexane:ethyl acetate=80:20) to give 2,4-dibromo-6-(4-ethylbenzyl)phenol (85%).

mp 90.0-91.5° C.

Reference Example 4

Preparation of methyl 3-(4-ethylbenzyl)-4-hydroxybenzoate

To a mixture of methyl 4-hydroxybenzoate (20 g, 131 mmol) and methanesulfonic acid (80 mL), hexamethylenetetramine (20 g, 144 mmol) was added in small portions at room temperature. After stirring at 100° C. for 3.5 hours, concentrated hydrochloric acid (10 mL) and water (300 mL) were added. The reaction mixture was extracted twice with ethyl acetate and the organic phase was dried over anhydrous magnesium sulfate. After the solvent was distilled off under reduced pressure, the resulting residue was purified by silica gel column chromatography (hexane:ethyl acetate=80:20-65:35) to give methyl 3-formyl-4-hydroxy-benzoate (7.24 g, 31%, mp 87.5-89.0° C.) as a colorless powder.

To a mixture of methyl 3-formyl-4-hydroxybenzoate (4.0 g, 22.2 mmol) and tetrahydrofuran (100 mL), 4-ethylphenyllithium [which had been prepared by stirring t-butyllithium (66 mmol) into a mixture of 1-bromo-4-ethylbenzene (12.3 g, 66 mmol) and tetrahydrofuran (200 mL) at −70° C. for 30 minutes] was added at −70° C. and stirred for 1 hour. After addition of saturated aqueous ammonium chloride, the reaction mixture was extracted with ethyl acetate, and the organic phase was washed with saturated aqueous sodium chloride and then dried over anhydrous magnesium sulfate. After the solvent was distilled off under reduced pressure, the resulting residue was purified by silica gel column chromatography (hexane:ethyl acetate=65:35-50:50) to give methyl 3-[(4-ethylphenyl)hydroxymethyl]benzoate (2.92 g, 46%) as a light-yellow gum.

The thus obtained methyl 3-[(4-ethylphenyl)hydroxy-methyl]benzoate (2.88 g, 10.0 mmol), 10% palladium carbon (200 mg), concentrated hydrochloric acid (0.5 mL) and methanol (15 mL) were mixed and stirred under a hydrogen atmosphere at room temperature for 14 hours. After filtration to remove the insoluble materials, the solvent was distilled off under reduced pressure and the resulting residue was purified by silica gel column chromatography (hexane:ethyl acetate=80:20) to give methyl 3-(4-ethylbenzyl)-4-hydroxybenzoate (2.38 g, 88%) as a colorless powder.

mp 134.0-137.0° C.

Reference Example 5

Preparation of 2-(4-ethylbenzyl)resorcinol

To a mixture of 1,3-dimethoxybenzene (6.9 g, 50 mmol) and tetrahydrofuran (70 mL), n-butyllithium (1.57 M in hexane, 35 mL) was added in ice and stirred for 1.5 hours. Subsequently, 4-ethylbenzyl bromide (10 g, 50 mmol) was added in ice and stirred for an additional 3.5 hours. After addition of saturated aqueous ammonium chloride, the reaction mixture was extracted with ethyl acetate, and the organic phase was washed with saturated aqueous sodium chloride and then dried over anhydrous magnesium sulfate. After the solvent was distilled off under reduced pressure, the resulting residue was purified by silica gel column chromatography (hexane:ethyl acetate=95:5-85:15) to give 1,3-dimethoxy-2-(4-ethylbenzyl)benzene (6.37 g, 49%, mp 62.5-66.5° C.) as a light-yellow powder.

A mixture of 1,3-dimethoxy-2-(4-ethylbenzyl)benzene (6.0 g, 23.4 mmol) and pyridine hydrochloride (21.6 g, 187 mmol) was heated and stirred at 180° C. for 15 hours. After addition of water, the reaction mixture was extracted with ethyl acetate, and the organic phase was washed with diluted aqueous hydrochloric acid and saturated aqueous sodium chloride and then dried over anhydrous magnesium sulfate. After the solvent was distilled off under reduced pressure, the resulting residue was purified by silica gel column chromatography (hexane:ethyl acetate 80:20) to give 2-(4-ethylbenzyl)resorcinol (5.2 g, 97%) as a light-brown oil.

Reference Example 6

Preparation of 2-(4-trifluoromethylbenzyl)phenol

To a mixture of magnesium (3.44 g, 142 mmol) and tetrahydrofuran (10 mL), 4-bromobenzotrifluoride (2-3 mL) was added at room temperature. After confirming the initiation of the reaction, a solution of additional 4-bromobenzotrifluoride (total 20.9 g, 93.1 mmol) in tetrahydrofuran (56 mL) was added dropwise and stirred for 30 minutes under the same conditions. After the reaction mixture was cooled in ice, a solution of 2-benzyloxybenzaldehyde (16.4 g, 77.2 mmol) in tetrahydrofuran (20 mL) was added and stirred at room temperature for 1 hour. The reaction mixture was poured into saturated aqueous ammonium chloride and extracted with ethyl acetate. The organic phase was washed with saturated aqueous sodium chloride and then dried over anhydrous magnesium sulfate. After the solvent was distilled off under reduced pressure, the resulting residue was purified by neutral silica gel column chromatography (hexane:ethyl acetate=90:10-85:15) to give 2-benzyloxy-(4'-trifluoromethyl)diphenylmethanol.

The thus obtained 2-benzyloxy-(4'-trifluoromethyl)diphenylmethanol, 10% palladium/carbon (1.68 g), concentrated hydrochloric acid (3.4 mL) and methanol (330 mL) were mixed and stirred under a hydrogen atmosphere at room temperature for 14.5 hours. After filtration to remove the insoluble materials, the solvent was distilled off under reduced pressure and the resulting residue was purified by silica gel column chromatography (hexane:ethyl acetate=93:7-85:15) to give 2-(4-trifluoromethylbenzyl)phenol (17.5 g, 90%) as a colorless oil.

Reference Example 7

The same procedure as shown in Reference Example 6 was repeated to give 2-(4-fluorobenzyl)phenol (99%) as a colorless oil.

Reference Example 8

The same procedure as shown in Reference Example 6 was repeated to give 2-(4-ethylbenzyl)-4-methylphenol (88%) as a yellow oil.

Reference Example 9

Preparation of 2-(4-ethylbenzyl)-4-fluorophenol

To a mixture of 2-bromo-4-fluorophenol (24.7 g, 129 mmol), tetrabutylammonium iodide (4.8 g, 13.0 mmol), potassium carbonate (35.9 g, 260 mmol) and N,N-dimethylformamide (390 mL), benzyl bromide (23.5 g, 137 mmol) was added at room temperature and stirred for 1.5 hours. The reaction mixture was poured into a mixture of ethyl acetate and saturated aqueous sodium chloride, and then extracted with ethyl acetate. The organic phase was washed twice with saturated aqueous sodium chloride and then dried over anhydrous magnesium sulfate. After the solvent was distilled off under reduced pressure, the resulting residue was purified by silica gel column chromatography (hexane:ethyl acetate=90:10-80:20) to give 1-benzyloxy-2-bromo-4-fluoro-benzene (33.0 g, 90%).

To a mixture of magnesium (3.2 g, 133 mmol) and tetrahydrofuran (10 mL), 1-benzyloxy-2-bromo-4-fluorobenzene (2-3 mL) was added at room temperature. After heating to start the reaction, a solution of additional 1-benzyloxy-2-bromo-4-fluorobenzene (total 30.0 g, 106 mmol) in tetrahydrofuran (60 mL) was added dropwise and stirred for 30 minutes under the same conditions. After the reaction mixture was cooled in ice, a solution of 4-ethylbenzaldehyde (16.4 g, 77.2 mmol) in tetrahydrofuran (20 mL) was added and stirred at room temperature for 3 hours. The reaction mixture was poured into saturated aqueous ammonium chloride and extracted with ethyl acetate. The organic phase was washed with saturated aqueous sodium chloride and then dried over anhydrous magnesium sulfate. After the solvent was distilled off under reduced pressure, the resulting residue was purified by neutral silica gel column chromatography (hexane:ethyl acetate=90:10-80:20) to give 2-benzyloxy-5-fluoro-(4'-ethyl)diphenylmethanol.

The thus obtained 2-benzyloxy-5-fluoro-(4'-ethyl)diphenylmethanol, 10% palladium carbon (1.77 g), concentrated hydrochloric acid (3.5 mL) and methanol (350 mL) were mixed and stirred under a hydrogen atmosphere at room temperature for 13 hours. After filtration to remove the insoluble materials, the solvent was distilled off under reduced pressure and the resulting residue was purified by silica gel column chromatography (hexane:ethyl acetate=90:10-80:20) to give 2-(4-ethylbenzyl)-4-fluorophenol (21.0 g, 85%) as a yellow oil.

Reference Example 10

Preparation of 2-(4-acetylbenzyl)phenol

A mixture of 2-(4-methoxycarbonylbenzyl)phenol (250 mg, 1.03 mmol), methanol (1.0 mL) and 2M NaOH (4.0 mL) was stirred at 75° C. for 1 hour. After cooling on ice, the reaction mixture was adjusted to pH 3.0 with 1M hydrochloric acid. The resulting precipitates were extracted with ethyl acetate, and the organic phase was washed with saturated aqueous sodium chloride and then dried over anhydrous magnesium sulfate. After the solvent was distilled off under reduced pressure, the resulting residue (230 mg) was diluted with tetrahydrofuran (10 mL), followed by addition of N—O-dimethylhydroxyamine hydrochloride (301 mg), triethylamine (0.456 mL), water (0.5 mL), WSC HCl (296 mg) and HOBT (210 mg). After stirring at room temperature for 2 hours, saturated aqueous $NaHCO_3$ was added to the reaction mixture. The mixture was extracted twice with ethyl acetate, and the combined organic phases were washed with saturated aqueous sodium chloride and dried over anhydrous magnesium sulfate.

After the solvent was concentrated, the resulting residue was purified by silica gel column chromatography (hexane:ethyl acetate=1:2) to give 4-(2-hydroxybenzyl)-N-methoxy-N-methylbenzamide (250 mg, 89%) as a colorless oil.

Next, 4-(2-hydroxybenzyl)-N-methoxy-N-methylbenzamide (250 mg, 0.921 mmol) was dissolved in tetrahydrofuran (10 mL), followed by addition of methylmagnesium bromide (12% in THF, 2.8 mL) at −20° C. After 15 minutes, a second addition of methylmagnesium bromide (12% in THF, 2.5 mL) was made, followed by a third addition of methylmagnesium bromide (12% in THF, 2.0 mL). After 10 minutes, saturated aqueous ammonium chloride was added to the reaction mixture, which was then extracted twice with ethyl acetate. The combined organic phases were washed with saturated aqueous sodium chloride and dried over anhydrous magnesium sulfate. After the solvent was concentrated, the resulting residue was purified by silica gel column chromatography (hexane:ethyl acetate=3:1) to give the titled compound (110 mg, 53%) as a colorless powder.

ESI $m/z$=249 (M+Na)

Reference Example 11

Preparation of 2,3,4,6-tetra-O-acetyl-5-thio-D-glucopyranose

To a solution of 1,2,3,4,6-penta-O-acetyl-5-thio-D-glucopyranose (34.0 g, 0.0837 mol) in N,N-dimethylformamide (300 mL), a mixture of methylhydrazine (6.70 mL, 0.120 mmol), acetic acid (15 mL, 0.120 mmol) and N,N-dimethylformamide (10 mL) was added in ice. After stirring at room temperature for 2.5 hours, 0.5M HCl (300 mL) was added to the reaction mixture in ice, which was then extracted twice with ethyl acetate (250 mL). The combined organic phases were washed sequentially with water (200 mL), saturated aqueous $NaHCO_3$ (100 mL), water (100 mL) and saturated aqueous sodium chloride (100 mL), followed by addition of $MgSO_4$ and activated charcoal (1 g). After filtration to remove the insoluble materials, the filtrate was concentrated under reduced pressure. The resulting residue was crystallized from isopropyl ether (70 mL) to give 2,3,4,6-tetra-O-acetyl-5-thio-glucopyranose (26.9 g, 88%) as a colorless crystal.

EXAMPLES

The compounds of the present invention will be further described in more detail in the following examples, which are not intended to limit the scope of the invention.

Example 1

Preparation of 2'-(4'-ethylbenzyl)phenyl 2,3,4,6-tetra-O-acetyl-5-thio-β-D-glucopyranoside 2,3,4,6-Tetra-O-acetyl-5-thio-D-glucopyranose (100 mg, 0.274 mmol), 2-(4-ethylbenzyl)phenol (117 mg, 0.551 mmol), triphenylphosphine (144 mg, 0.548 mmol) and THF (3 mL) were mixed, and to the resulting mixture, diethyl azodicarboxylate (40% in toluene, 0.24 mL) was then slowly added dropwise at room temperature. After stirring at room temperature for 20 hours, the reaction mixture was concentrated and the resulting residue was purified by silica gel column chromatography (hexane:ethyl acetate=7:3) to give the titled compound (12 mg, 11%) as a colorless powder.

¹H-NMR (300 MHz, CDCl₃): δ 1.20 (t, J=7.6 Hz, 3H), 1.90 (s, 3H), 2.01 (s, 3H), 2.04 (s, 3H), 2.05 (s, 3H), 2.60 (q, J=7.6 Hz, 2H), 3.20-3.30 (m, 1H), 3.88 (s, 2H), 4.08-4.17 (m, 1H), 4.25-4.35 (m, 1H), 5.16 (dd, J=8.9, 9.3 Hz, 1H), 5.33 (d, J=8.6 Hz, 1H), 5.39 (dd, J=9.3, 10.4 Hz, 1H), 5.62 (dd, J=8.6, 8.9 Hz, 1H), 6.94-7.00 (m, 1H), 7.04-7.14 (m, 6H), 7.17-7.24 (m, 1H).
ESI m/z=557 (M−H)
mp 114.0-119.0° C.

Example 2

Preparation of 2'-(4'-ethylbenzyl)-4'-chlorophenyl 2,3,4,6-tetra-O-acetyl-5-thio-β-D-glucopyranoside The same procedure as shown in Example 1 was repeated to give the titled compound in a yield of 28% as a light-yellow gum.
¹H-NMR (300 MHz, CDCl₃): δ 1.21 (t, J=7.6 Hz, 3H), 1.92 (s, 3H), 2.01 (s, 3H), 2.04 (s, 3H), 2.06 (s, 3H), 2.61 (q, J=7.6 Hz, 2H), 3.23-3.30 (m, 1H), 3.84 (s, 2H), 4.13 (dd, J=3.7 and 8.1 Hz, 1H), 4.25-4.36 (m, 1H), 5.14 (dd, J=9.0 and 9.5 Hz, 1H), 5.28 (d, J=8.7 Hz, 1H), 5.37 (dd, J=9.5 and 10.2 Hz, 1H), 5.60 (dd, J=8.7 and 9.0 Hz, 1H), 7.00-7.20 (m, 7H).
ESI m/z=615 (M+Na)

Example 3

Preparation of 2'-(4'-methylbenzyl)phenyl 2,3,4,6-tetra-O-acetyl-5-thio-β-D-glucopyranoside The same procedure as shown in Example 1 was repeated to give the titled compound in a yield of 14% as a colorless powder.
ESI m/z=567 (M+Na)
mp 109.0-113.0° C.

Example 4

Preparation of 2'-(4'-methoxybenzyl)phenyl 2,3,4,6-tetra-O-acetyl-5-thio-β-D-glucopyranoside 2,3,4,6-Tetra-O-acetyl-5-thio-D-glucopyranose (2.00 g, 5.48 mmol), 2-(4-methoxybenzyl)phenol (5.88 g, 27.4 mmol), triphenylphosphine (2.88 g, 10.9 mmol) and THF (20 mL) were mixed, and to the resulting mixture, diethyl azocarboxylate (40% in toluene, 4.79 g, 10.9 mmol) was then slowly added dropwise in ice. After stirring at room temperature for 20 hours, the reaction mixture was concentrated and the resulting residue was purified by silica gel column chromatography (hexane:ethyl acetate=65:35). The resulting crude product was recrystallized from methanol to give the titled compound (457 mg, 15%) as a colorless powder.
¹H-NMR (300 MHz, CDCl₃): δ 1.93 (s, 3H), 2.02 (s, 3H), 2.04 (s, 3H), 2.06 (s, 3H), 3.23-3.28 (m, 1H), 3.77 (s, 3H), 3.85 (s, 2H), 4.09-4.14 (m, 1H), 4.28-4.33 (m, 1H), 5.16 (dd, J=9.1, 9.3 Hz, 1H), 5.33 (d, J=8.7 Hz, 1H), 5.39 (dd, J=9.6, 10.2 Hz, 1H), 5.62 (dd, J=8.7, 9.0 Hz, 1H), 6.79-6.82 (m, 2H), 6.95-7.21 (m, 6H).
ESI m/z=583 (M+Na).
mp 87.0-89.0° C.

Example 5

Preparation of 2'-(4'-ethoxybenzyl)phenyl 2,3,4,6-tetra-O-acetyl-5-thio-β-D-glucopyranoside 2,3,4,6-Tetra-O-acetyl-5-thio-D-glucopyranose (2.0 g, 5.48 mmol), 2-(4-ethoxybenzyl)phenol (6.25 g, 27.4 mmol), triphenylphosphine (2.88 g, 10.9 mmol) and tetrahydrofuran (20 mL) were mixed, and to the resulting mixture, diethyl azocarboxylate (40% in toluene, 4.79 g) was then slowly added dropwise in ice. After stirring at room temperature for 17 hours, the reaction mixture was concentrated and the resulting residue was purified by silica gel column chromatography (hexane:ethyl acetate=65:35). The resulting powder was recrystallized from methanol to give the titled compound (598 mg, 19%) as a colorless powder.
ESI m/z=597 (M+Na)
mp 93.0-94.5° C.

Example 6

Preparation of 2'-(4'-trifluoromethylbenzyl)phenyl 2,3,4,6-tetra-O-acetyl-5-thio-β-D-glucopyranoside 2,3,4,6-Tetra-O-acetyl-5-thio-D-glucopyranose (2.00 g, 5.48 mmol), 2-(4-trifluoromethylbenzyl)phenol (6.91 g, 27.4 mmol), triphenylphosphine (2.88 g, 10.9 mmol) and THF (20 mL) were mixed, and to the resulting mixture, diethyl azocarboxylate (40% in toluene, 4.79 g, 10.9 mmol) was then slowly added dropwise in ice. After stirring at room temperature for 20 hours, the reaction mixture was concentrated and the resulting residue was purified by silica gel column chromatography (hexane:ethyl acetate=65:35). The resulting crude product was recrystallized from methanol to give the titled compound (630 mg, 19%) as a colorless powder.
¹H-NMR (300 MHz, CDCl₃): δ 1.90 (s, 3H), 2.01 (s, 3H), 2.05 (s, 6H), 3.23-3.30 (m, 1H), 3.96 (s, 2H), 4.07-4.13 (m, 1H), 4.27-4.32 (m, 1H), 5.16 (dd, J=9.0, 9.5 Hz, 1H), 5.34-5.41 (m, 2H), 5.57 (dd, J=8.5, 9.1 Hz, 1H), 7.01-7.29 (m, 6H), 7.50-7.53 (m, 2H).
ESI m/z=621 (M+Na).
mp 144.0-145.0° C.

Example 7

Preparation of 2'-(4'-ethylbenzyl)-4'-methylphenyl 2,3,4,6-tetra-O-acetyl-5-thio-β-D-glucopyranoside The same procedure as shown in Example 1 was repeated to give the titled compound in a yield of 18% as a colorless powder.
ESI m/z=595 (M+Na)
mp 77.0-79.5° C.

Example 8

Preparation of 2'-(4'-ethylbenzyl)-4'-fluorophenyl 2,3,4,6-tetra-O-acetyl-5-thio-β-D-glucopyranoside The same procedure as shown in Example 1 was repeated to give the titled compound in a yield of 23% as a yellow amorphous substance.
¹H-NMR (300 MHz, CDCl₃): δ 1.22 (t, J=7.6 Hz, 3H), 1.94 (s, 3H), 2.02 (s, 3H), 2.04 (s, 3H), 2.06 (s, 3H), 2.61 (q, J=7.6 Hz, 2H), 3.21-3.28 (m, 1H), 3.86 (s, 2H), 4.10-4.15 (m, 1H), 4.31-4.34 (m, 1H), 5.15 (dd, J=9.0 and, 9.5 Hz, 1H), 5.25 (d, J=8.7 Hz, 1H), 5.39 (dd, J=9.6 and 10.3 Hz, 1H), 5.61 (dd, J=8.7 and 9.0 Hz, 1H), 6.71-7.13 (m, 7H)
ESI m/z=599 (M+Na)

Example 9

Preparation of 2'-(4'-fluorobenzyl)phenyl 2,3,4,6-tetra-O-acetyl-5-thio-β-D-glucopyranoside 2,3,4,6-Tetra-O-acetyl-5-thio-D-glucopyranose (2.00 g, 5.48 mmol), 2-(4-fluorobenzyl)phenol (5.54 g, 27.4 mmol), triphenylphosphine (2.88 g, 10.9 mmol) and toluene (20 mL)

were mixed, and to the resulting mixture, diethyl azocarboxylate (40% in toluene, 4.79 g, 10.9 mmol) was then slowly added dropwise in ice. After stirring at room temperature for 20 hours, the reaction mixture was concentrated and the resulting residue was purified by silica gel column chromatography (hexane:ethyl acetate=90:10). The resulting crude product was recrystallized from methanol to give the titled compound (751 mg, 25%) as a colorless powder.

$^1$H-NMR (300 MHz, CDCl$_3$): δ 1.93 (s, 3H), 2.02 (s, 3H), 2.04 (s, 3H), 2.05 (s, 3H), 3.23-3.30 (m, 1H), 3.87 (s, 2H), 4.09-4.14 (m, 1H), 4.27-4.33 (m, 1H), 5.16 (dd, J=9.0, 9.4 Hz, 1H), 5.33-5.41 (m, 2H), 5.59 (dd, J=8.7, 9.0 Hz, 1H), 6.91-7.26 (m, 8H).

ESI m/z=571 (M+Na).

mp 99.0-103.0° C.

Example 10

Preparation of 4'-bromo-2'-(4'-ethylbenzyl)phenyl 2,3,4,6-tetra-O-acetyl-5-thio-β-D-glucopyranoside The same procedure as shown in Example 1 was repeated to give the titled compound in a yield of 36% as a yellow amorphous substance.

$^1$H-NMR (300 MHz, CDCl$_3$): δ 1.21 (t, J=7.6 Hz, 3H), 1.91 (s, 3H), 2.01 (s, 3H), 2.04 (s, 3H), 2.06 (s, 3H), 2.61 (q, J=7.6 Hz, 2H), 3.25-3.30 (m, 1H), 3.84 (s, 2H), 4.10-4.15 (m, 1H), 4.27-4.33 (m, 1H), 5.15 (dd, J=8.5 and 8.7 Hz, 1H), 5.38 (t, J=8.9 Hz, 1H), 5.60 (dd, J=8.7 and 8.9 Hz, 1H), 6.98-7.32 (m, 7H).

ESI m/z=659 (M+Na).

Example 11

Preparation of 2'-benzylphenyl 2,3,4,6-tetra-O-acetyl-5-thio-β-D-glucopyranoside The same procedure as shown in Example 1 was repeated to give the titled compound in a yield of 18% as a colorless powder.

ESI m/z=553 (M+Na).

mp 124.5-125.5° C.

Example 12

Preparation of 3'-acetoxy-2'-(4'-ethylbenzyl)phenyl 2,3,4,6-tetra-O-acetyl-5-thio-β-D-glucopyranoside 2,3,4,6-Tetra-O-acetyl-5-thio-D-glucopyranose (1.29 g, 3.54 mmol), 2-(4-ethylbenzyl)resorcinol (2.42 g, 10.6 mmol), triphenylphosphine (1.86 g, 7.09 mmol) and toluene (13 mL) were mixed, and to the resulting mixture, diisopropyl azodicarboxylate (40% in toluene, 3.58 g) was then slowly added dropwise in ice. After stirring at room temperature for 24 hours, the reaction mixture was concentrated and the resulting residue was purified by silica gel column chromatography (hexane:ethyl acetate=65:35-50:50) to give a crude product of 3-hydroxy-2-(4-ethylbenzyl)phenyl 2,3,4,6-tetra-O-acetyl-5-thio-β-D-glucopyranoside (338 mg). To a mixture of this crude product (338 mg) and pyridine (2 mL), acetic anhydride (0.5 mL) was added at room temperature. After stirring at room temperature for 20 hours, water was added to the reaction mixture, which was then extracted with ethyl acetate. The organic phase was washed with saturated aqueous sodium chloride and then dried over anhydrous magnesium sulfate. After the solvent was distilled off under reduced pressure, the resulting residue was purified by silica gel column chromatography (hexane:ethyl acetate =2:1) to give the titled compound (134 mg, 6%) as a light-yellow gum.

$^1$H-NMR (300 MHz, CDCl$_3$): δ 1.18 (t, J=7.6 Hz, 3H), 1.83 (s, 3H), 1.99 (s, 3H), 2.04 (s, 3H), 2.06 (s, 3H), 2.16 (s, 3H), 2.57 (q, J=7.6 Hz, 2H), 3.24-3.30 (m, 1H), 3.75-3.90 (m, 2H), 4.10 (dd, J=3.8 and 12.0 Hz, 1H), 4.29 (dd, J=5.2 and 12.0 Hz, 1H), 5.14 (dd, J=8.8 and 9.3 Hz, 1H), 5.32 (d, J=8.7 Hz, 1H), 5.36 (dd, J=9.5 and 10.0 Hz, 1H), 5.58 (dd, J=8.7 and 9.1 Hz, 1H), 6.82 (d, J=8.2 Hz, 1H), 6.98-7.07 (m, 5H), 7.20-7.30 (m, 1H).

ESI m/z=639 (M+Na).

Example 13

Preparation of 2'-(4'-ethylbenzyl)-4'-methoxycarbonylphenyl 2,3,4,6-tetra-O-acetyl-5-thio-β-D-glucopyranoside 2,3,4,6-Tetra-O-acetyl-5-thio-D-glucopyranose (1.0 g, 2.74 mmol), methyl 3-(4-ethylbenzyl)-4-hydroxybenzoate (2.23 g, 8.25 mmol), triphenylphosphine (1.44 g, 5.48 mmol) and toluene (5 mL) were mixed, and to the resulting mixture, diisopropyl azodicarboxylate (40% in toluene, 2.77 g) was then slowly added dropwise in ice. After stirring at room temperature for 17 hours, the reaction mixture was concentrated and the resulting residue was purified by silica gel column chromatography (hexane:ethyl acetate=65:35-50:50) to give the titled compound (646 mg, 38%) as a colorless amorphous substance.

$^1$H-NMR (300 MHz, CDCl$_3$): δ 1.20 (t, J=7.6 Hz, 3H), 1.88 (s, 3H), 2.01 (s, 3H), 2.04 (s, 3H), 2.05 (s, 3H), 2.59 (q, J=7.6 Hz, 2H), 3.27-3.35 (m, 1H), 3.86 (s, 3H), 3.89 (s, 2H), 4.13 (dd, J=3.9 and 12.0 Hz, 1H), 4.30 (dd, J=5.4 and 12.0 Hz, 1H), 5.17 (dd, J=8.8 and 9.3 Hz, 1H), 5.40 (dd, J=9.3 and 10.3 Hz, 1H), 5.40 (d, J=8.5 Hz, 1H), 5.61 (dd, J=8.5 and 8.8 Hz, 1H), 7.03-7.11 (m, 4H), 7.13 (d, J=8.7 Hz, 1H), 7.83 (d, J=2.2 Hz, 1H), 7.92 (d, J=2.2 and 8.7 Hz, 1H).

ESI m/z=639 (M+Na).

Example 14

Preparation of 4',6'-dibromo-2'-(4'-ethylbenzyl)phenyl 2,3,4,6-tetra-O-acetyl-5-thio-β-D-glucopyranoside 2,3,4,6-Tetra-O-acetyl-5-thio-D-glucopyranose (510 mg, 1.4 mmol), 4,6-dibromo-2-(4-ethylbenzyl)phenol (1.05 g, 2.8 mmol), triphenylphosphine (550 mg, 2.1 mmol) and toluene (8 mL) were mixed, and to the resulting mixture, diisopropyl azodicarboxylate (40% in toluene, 1.06 g, 2.1 mmol) was then slowly added dropwise in ice. After stirring at room temperature for 12 hours, the reaction mixture was concentrated and the resulting residue was purified by silica gel column chromatography (hexane:ethyl acetate=7:3) to give the titled compound (550 mg, 55%) as a colorless powder.

$^1$H-NMR (200 MHz, CDCl$_3$): δ 1.23 (t, J=7.5 Hz, 3H), 2.02 (s, 3H), 2.03 (s, 3H), 2.05 (s, 3H), 2.06 (s, 3H), 2.63 (q, J=7.5 Hz, 2H), 2.95 (m, 1H), (m, 1H), 3.92 (d, J=15.6 Hz, 1H), 4.02 (dd, J=3.3, 12.1 Hz, 1H), 4.12 (d, J=15.6 Hz, 1H), 4.31 (dd, J=5.1, 12.1 Hz, 1H), 5.11 (t, J=9.2 Hz, 1H), 5.34 (dd, J=9.2, 10.7 Hz, 1H), 5.52 (d, J=9.2 Hz, 1H), 5.71 (t, J=9.2 Hz, 1H), 7.07-7.17 (m, 5H), 7.56 (d, J=2.4 Hz, 1H).

ESI m/z=737, 739, 740, 742 (M+Na).

mp 152.0-155.0° C.

Example 15

Preparation of 2'-(4'-benzoyloxybenzyl)phenyl 2,3,4,6-tetra-O-acetyl-5-thio-β-D-glucopyranoside The same procedure as shown in Example 1 was repeated to give the titled compound in a yield of 16% as a colorless amorphous substance.

$^1$H-NMR (300 MHz, CDCl$_3$): δ 1.94 (s, 3H), 2.03 (s, 3H), 2.06 (s, 3H), 2.08 (s, 3H), 3.26-3.30 (m, 1H), 3.94 (s, 2H), 4.10-4.16 (m, 1H), 4.29-4.34 (m, 1H), 5.18 (dd, J=8.7 and 9.0 Hz, 1H), 5.34-5.40 (m, 2H), 5.62 (dd, J=8.5 and 9.0 Hz, 1H), 7.00-7.27 (m, 8H), 7.47-7.63 (m, 3H), 8.17-8.20 (m, 2H).
ESI m/z=673 (M+Na).

Example 16

Preparation of 2'-[4'-(2'-benzoyloxyethyl)benzyl]phenyl 2,3,4,6-tetra-O-acetyl-5-thio-β-D-glucopyranoside The same procedure as shown in Example 1 was repeated to give the titled compound as a yellow oil.

$^1$H-NMR (300 MHz, CDCl$_3$): δ 1.90 (s, 3H), 2.01 (s, 3H), 2.05 (s, 3H), 2.08 (s, 3H), 3.04 (t, J=7.0 Hz, 2H), 3.28-3.30 (m, 1H), 3.90 (s, 2H), 4.10-4.17 (m, 1H), 4.28-4.47 (m, 1H), 4.50 (t, J=7.0 Hz, 2H), 5.13-5.19 (m, 1H), 5.32-5.39 (m, 2H), 5.62 (dd, J=8.7 and 8.9 Hz, 1H), 6.97-7.27 (m, 8H), 7.40-7.55 (m, 3H), 7.99-8.03 (m, 2H).
ESI m/z=701 (M+Na).

Example 17

Preparation of 2'-(4'-ethylbenzyl)-5'-(methoxymethyloxy)phenyl 2,3,4,6-tetra-O-acetyl-5-thio-β-D-glucopyranoside The same procedure as shown in Example 1 was repeated to give the titled compound in a yield of 23% as a colorless gum.

$^1$H-NMR (300 MHz, CDCl$_3$): δ 1.20 (t, J=7.6 Hz, 3H), 1.90 (s, 3H), 2.00 (s, 3H), 2.04 (s, 3H), 2.06 (s, 3H), 2.59 (q, J=7.6 Hz, 2H), 3.21-3.31 (m, 1H), 3.48 (s, 3H), 3.81 (s, 2H), 4.13 (dd, J=3.7 and 11.8 Hz, 1H), 4.31 (dd, J=5.1 and 11.8 Hz, 1H), 5.12-5.20 (m, 1H), 5.15 (s, 2H), 5.28 (d, J=8.7 Hz, 1H), 5.38 (dd, J=9.5 and 10.3 Hz, 1H), 5.60 (dd, J=8.7 and 9.0 Hz, 1H), 6.68 (dd, J=2.3 and 8.4 Hz, 1H), 6.83 (d, J=2.3 Hz, 1H), 6.96 (d, J=8.4 Hz, 1H), 7.02-7.11 (m, 4H).
ESI m/z=641 (M+Na).

Example 18

Preparation of 4'-bromo-2'-benzoylphenyl 2,3,4,6-tetra-O-acetyl-5-thio-β-D-glucopyranoside 2,3,4,6-Tetra-O-acetyl-5-thio-D-glucopyranose (200 mg, 0.549 mmol), 4-bromo-2-benzoylphenol (773 mg, 2.79 mmol), triphenylphosphine (191 mg, 1.10 mmol) and toluene (1.6 mL) were mixed, and to the resulting mixture, diethyl azodicarboxylate (40% in toluene, 0.48 mL, 1.10 mmol) was then slowly added dropwise in ice. After stirring at room temperature for 12 hours, the reaction mixture was concentrated and the resulting residue was purified by silica gel column chromatography (hexane:ethyl acetate=7:3) to give the titled compound.

$^1$H-NMR (300 MHz, CDCl$_3$): δ 1.89 (s, 3H), 1.94 (s, 3H), 2.01 (s, 3H), 2.06 (s, 3H), 3.23 (m, 1H), 4.08-4.14 (m, 2H), 5.16-5.25 (m, 3H), 7.19 (d, J=8.9 Hz, 1H), 7.43-7.48 (m, 3H), 7.57-7.61 (m, 2H), 7.74-7.77 (m, 2H).
ESI m/z=645, 647 (M+Na).

Example 19

Preparation of 4'-chloro-2'-benzylphenyl 2,3,4,6-tetra-O-acetyl-5-thio-β-D-glucopyranoside 2,3,4,6-Tetra-O-acetyl-5-thio-D-glucopyranose (200 mg, 0.549 mmol), 4-chloro-2-benzylphenol (601 mg, 2.75 mmol), triphenylphosphine (191 mg, 1.10 mmol) and toluene (1.6 mL) were mixed, and to the resulting mixture, diethyl azodicarboxylate (40% in toluene, 0.48 mL, 1.10 mmol) was then slowly added dropwise in ice. After stirring at room temperature for 12 hours, the reaction mixture was concentrated and the resulting residue was purified by silica gel column chromatography (hexane:ethyl acetate=7:3) to give the titled compound (173 mg, 56%).

$^1$H-NMR (300 MHz, CDCl$_3$): δ 1.91 (s, 3H), 2.01 (s, 3H), 2.05 (s, 3H), 2.06 (s, 3H), 3.28 (m, 1H), 3.88 (s, 2H), 4.14 (dd, J=3.7, 12.0 Hz, 1H), 4.30 (dd, J=5.3, 12.0 Hz, 1H), 5.16 (dd, J=8.8, 9.5 Hz, 1H), 5.31 (d, J=8.6 Hz, 1H), 5.39 (dd, J=9.5, 10.3 Hz, 1H), 5.60 (dd, J=8.6, 8.8 Hz, 1H), 7.03-7.35 (m, 8H).
ESI m/z=587, 589 (M+Na).
mp 111.0-114.0° C.

Example 20

Preparation of 2'-(4'-ethylbenzyl)phenyl 2,4,6-tri-O-pivaloyl-5-thio-β-D-glucopyranoside 2,4,6-Tri-O-pivaloyl-5-thio-D-glucopyranose (200 mg, 0.446 mmol), 2-(4-ethylbenzyl)phenol (473 mg, 2.23 mmol), triphenylphosphine (155 mg, 0.892 mmol) and THF (1.6 mL) were mixed, and to the resulting mixture, diethyl azodicarboxylate (40% in toluene, 0.39 mL) was then slowly added dropwise at room temperature. After stirring at room temperature for 10 hours, the reaction mixture was concentrated and the resulting residue was purified by silica gel column chromatography (hexane:ethyl acetate 9:1) to give the titled compound (91 mg, 32%).

$^1$H-NMR (300 MHz, CDCl$_3$): δ 1.16 (s, 9H), 1.19 (s, 9H), 1.23 (s, 9H), 2.60 (q, J=7.7 Hz, 2H), 3.25 (m, 1H), 3.62 (dd, J=8.6, 9.2 Hz, 1H), 3.83 (d, J=15 Hz, 1H), 3.93 (d, J=15 Hz, 1H), 4.22 (m 2H), 5.27 (dd, J=9.2, 10.6 Hz, 1H), 5.37 (d, J=8.6 Hz, 1H), 5.49 (t, J=8.6 Hz, 1H), 6.92-7.20 (m, 8H).
ESI m/z=665 (M+Na).

Example 21

Preparation of 2'-(4'-ethylbenzyl)phenyl 2,3,4,6-tetra-O-benzoyl-5-thio-β-D-glucopyranoside 2,3,4,6-Tetra-O-benzoyl-5-thio-D-glucopyranose (200 mg, 0.33 mmol), 2-(4-ethylbenzyl)phenol (347 mg, 1.63 mmol), triphenylphosphine (171 mg, 0.65 mmol) and toluene (2 mL) were mixed, and to the resulting mixture, diethyl azodicarboxylate (40% in toluene, 284 mg) was then slowly added dropwise at room temperature. After stirring at room temperature for 16.5 hours, the reaction mixture was concentrated and the resulting residue was purified by silica gel column chromatography (hexane:ethyl acetate=4:1) to give the titled compound (41 mg, 15%) as a colorless amorphous substance.

$^1$H-NMR (300 MHz, CDCl$_3$): δ 1.16 (t, J=7.6 Hz, 3H), 2.53 (q, J=7.6 Hz, 2H), 3.70-3.80 (m, 1H), 3.76 (d, J=15.5 Hz, 1H), 3.87 (d, J=15.5 Hz, 1H), 4.54 (dd, J=5.1 and 12.0 Hz, 1H), 4.65 (dd, J=4.5 and 12.0 Hz, 1H), 5.65 (d, J=8.4 Hz, 1H), 5.84 (dd, J=9.1 and 9.5 Hz, 1H), 6.03 (dd, J=9.5 and 10.0 Hz, 1H), 6.17 (dd, J=8.4 and 9.1 Hz, 1H), 6.85-7.60 (m, 20H), 7.70-8.05 (m, 8H).

ESI m/z=829 (M+Na).

Example 22

Preparation of 5'-acetyloxymethyl-2'-(4'-ethylbenzyl)phenyl 2,3,4,6-tetra-O-acetyl-5-thio-β-D-glucopyranoside 2,3,4,6-Tetra-O-acetyl-5-thio-D-glucopyranose (1.0 g, 2.7 mmol), 5-acetyloxymethyl-2-(4-ethylbenzyl)phenol (1.5 g, 5.3 mmol), triphenylphosphine (941 mg, 5.4 mmol) and toluene (5 mL) were mixed, and to the resulting mixture, diisopropyl azodicarboxylate (40% in toluene, 3.2 mL) was then added dropwise in ice. After stirring at room temperature for 22 hours, the reaction mixture was concentrated and the resulting residue was purified by silica gel column chromatography (hexane:ethyl acetate=6:4) to give the titled compound (670 mg, 39%) as a colorless amorphous substance.

$^1$H-NMR (200 MHz, CDCl$_3$): δ 1.20 (t, J=7.7 Hz, 3H), 1.99 (s, 3H), 2.01 (s, 3H), 2.05 (s, 3H), 2.06 (s, 3H), 2.11 (s, 3H), 2.60 (q, J=7.7 Hz, 2H), 3.29 (ddd, J=4.0, 5.2, 10.1 Hz, 1H), 3.86-3.92 (m, 2H), 4.13 (dd, J=4.0, 12.0 Hz, 1H), 4.31 (dd, J=5.2, 12.0 Hz, 1H), 5.05-5.07 (m, 2H), 5.17 (dd, J=8.8, 9.4 Hz, 1H), 5.33 (d, J=8.8 Hz, 1H), 5.40 (dd, J=9.4, 10.1 Hz, 1H), 5.61 (d, J=8.8 Hz, 1H), 6.95-7.15 (m, 7H).

ESI m/z=653 (M+Na).

Example 23 (Compound 1)

Preparation of 2'-(4'-ethylbenzyl)phenyl 5-thio-β-D-glucopyranoside

To a mixture of 2'-(4'-ethylbenzyl)phenyl 2,3,4,6-tetra-O-acetyl-5-thio-β-D-glucopyranoside (310 mg, 0.555 mmol) and methanol (5 mL), sodium methoxide (30 mg, 0.555 mmol) was added and stirred at room temperature for 10 hours. After addition of Dowex-50W×8 ion exchange resin, the reaction mixture was neutralized and filtered. The resulting filtrate was concentrated and the residue was purified by silica gel column chromatography (chloroform:methanol=20:1) to give the titled compound (170 mg, 78%) as a colorless powder.

$^1$H-NMR (300 MHz, MeOH-d$_4$): δ 1.19 (t, J=7.3 Hz, 3H), 2.58 (q, J=7.3 Hz, 2H), 2.88-2.95 (m, 1H), 3.29-3.31 (m, 1H), 3.55-3.60 (m, 1H), 3.74-3.83 (m, 2H), 3.90-3.93 (m, 1H), 3.97-3.99 (m, 2H), 5.17 (d, J=8.5 Hz, 1H), 6.91 (dt, J=1.2, 7.4 Hz, 1H), 7.10-7.19 (m, 6H), 7.27 (d, J=7.9 Hz, 1H).

ESI m/z=389 (M−H).

mp 154.0-160.0° C.

Example 24 (Compound 1)

Preparation of 2'-(4'-ethylbenzyl)phenyl 5-thio-β-D-glucopyranoside

4',6'-Dibromo-2'-(4'-ethylbenzyl)phenyl 2,3,4,6-tetra-O-acetyl-5-thio-β-D-glucopyranoside (410 mg, 0.572 mmol), potassium carbonate (158 mg, 1.15 mmol), 10% palladium/activated charcoal (50% wet, 200 mg) and methanol (20 mL) were mixed and stirred under a hydrogen atmosphere at room temperature for 20 hours. The reaction mixture was filtered through celite to remove the insoluble materials and the filtrate was concentrated. The resulting residue was recrystallized from methanol/water to give the titled compound (177 mg, 79%) as a colorless powder.

$^1$H-NMR (300 MHz, MeOH-d$_4$): δ 1.19 (t, J=7.3 Hz, 3H), 2.58 (q, J=7.3 Hz, 2H), 2.88-2.95 (m, 1H), 3.29-3.31 (m, 1H), 3.55-3.60 (m, 1H), 3.74-3.83 (m, 2H), 3.90-3.93 (m, 1H), 3.97-3.99 (m, 2H), 5.17 (d, J=8.5 Hz, 1H), 6.91 (dt, J=1.2, 7.4 Hz, 1H), 7.10-7.19 (m, 6H), 7.27 (d, J=7.9 Hz, 1H).

ESI m/z=389 (M−H).

mp 156.5-157.5° C.

Example 25 (Compound 13)

Preparation of 2'-(4'-ethylbenzyl)-4'-(hydroxymethyl)phenyl 5-thio-β-D-glucopyranoside To a mixture of lithium aluminum hydride (90 mg, 2.37 mmol) and tetrahydrofuran (5 mL), a solution of 2'-(4'-ethylbenzyl)-4'-(methoxycarbonyl)phenyl 2,3,4,6-tetra-O-acetyl-5-thio-β-D-glucopyranoside (293 mg, 0.475 mmol) in tetrahydrofuran (10 mL) was added in ice and stirred at room temperature for 2 hours. After addition of a small amount of ethyl acetate and water, the reaction mixture was stirred for a period of time, extracted with chloroform and then dried over anhydrous magnesium sulfate. After the solvent was distilled off under reduced pressure, the resulting residue was purified by silica gel column chromatography (chloroform:methanol=9:1) to give the titled compound (55 mg, 28%) as a colorless powder.

$^1$H-NMR (300 MHz, CD$_3$OD): δ 1.19 (t, J=7.6 Hz, 3H), 2.57 (q, J=7.6 Hz, 2H), 2.87-2.95 (m, 1H), 3.28-3.33 (m, 1H), 3.57 (dd, J=8.9 and 10.3 Hz, 1H), 3.73-3.83 (m, 2H), 3.88-4.03 (m, 3H), 4.47 (s, 2H), 5.17 (d, J=8.7 Hz, 1H), 7.04-7.19 (m, 6H), 7.25 (d, J=8.4 Hz, 1H).

ESI m/z=443 (M+Na).

mp 202.5-205.0° C.

Example 26 (Compound 21)

Preparation of 2'-(4'-ethylbenzyl)-5'-hydroxyphenyl 5-thio-β-D-glucopyranoside

A mixture of 2'-(4'-ethylbenzyl)-5'-(methoxymethyloxy)phenyl 5-thio-β-D-glucopyranoside (115 mg, 0.255 mmol) and p-toluenesulfonic acid monohydrate (15 mg, 0.09 mmol) was stirred at room temperature for 23 hours and then at 50° C. for 1 hour, followed by addition of p-toluenesulfonic acid monohydrate (23 mg, 0.13 mmol) and further stirring at 50° C. for 5 hours. After addition of triethylamine (0.5 mL), the reaction mixture was evaporated under reduced pressure to remove the solvent and the resulting residue was purified by silica gel column chromatography (chloroform:methanol=20:1-9:1) to give the titled compound (85 mg, 82%) as a colorless powder.

$^1$H-NMR (300 MHz, CD$_3$OD): δ 1.19 (t, J=7.6 Hz, 3H), 2.57 (q, J=7.6 Hz, 2H), 2.85-2.94 (m, 1H), 3.24-3.33 (m, 1H), 3.56 (dd, J=9.0 and 10.3 Hz, 1H), 3.73-3.90 (m, 4H), 3.92 (dd, J=3.7 and 7.8 Hz, 1H), 5.08 (d, J=8.7 Hz, 1H), 6.37 (dd, J=2.3 and 8.2 Hz, 1H), 6.76 (d, J=2.3 Hz, 1H), 6.83 (d, J=8.2 Hz, 1H), 7.00-7.10 (m, 4H).

ESI m/z=429 (M+Na).

mp 172.0-173.5° C.

Example 27 (Compound 23)

Preparation of 2'-(4'-ethylbenzyl)phenyl 6-O-methoxycarbonyl 5-thio-β-D-glucopyranoside To a mixture of 2'-(4'-ethylbenzyl)phenyl 5-thio-β-D-glucopyranoside (500 mg, 1.33 mmol) and 2,4,6-collidine (5 mL), a solution of methyl chloroformate (151 mg, 1.6 mmol) in methylene chloride (0.5 mL) was added at −40° C. The reaction mixture was then warmed to −10° C. over 1 hour and stirred at room temperature for 2.5 hours. The reaction mixture was poured into ice-cold 10% aqueous hydrochloric acid and extracted with ethyl acetate. The organic phase was washed with saturated aqueous sodium bicarbonate and saturated aqueous sodium chloride, and then dried over anhydrous magnesium sulfate. After the solvent was distilled off under reduced pressure, the resulting residue was purified by silica gel column chromatography (chloroform:methanol=30:1-20:1-10:1) to give the titled compound (340 mg, 59%) as a colorless powder.

$^1$H-NMR (300 MHz, CD$_3$OD): δ 1.19 (t, J=7.6 Hz, 3H), 2.58 (q, J=7.6 Hz, 2H), 3.04-3.14 (m, 1H), 3.26-3.34 (m, 1H), 3.57 (dd, J=9.2 and 10.3 Hz, 1H), 3.74 (s, 3H), 3.76-3.85 (m, 1H), 3.92 (d, J=14.0 Hz, 1H), 3.99 (d, J=14.0 Hz, 1H), 4.35 (dd, J=6.2 and 11.3 Hz, 1H), 4.48 (dd, J=3.3 and 11.3 Hz, 1H), 5.19 (d, J=8.7 Hz, 1H), 6.88-6.95 (m, 1H), 7.02-7.28 (m, 7H).

ESI m/z=471 (M+Na).

mp 102.0-104.5° C.

Example 28 (Compound 39)

Preparation of 2'-(4'-ethylbenzyl)-5'-(hydroxymethyl)phenyl 5-thio-β-D-glucopyranoside A mixture of 5'-acetyloxymethyl-2'-(4'-ethylbenzyl)phenyl 2,3,4,6-tetra-O-acetyl-5-thio-β-D-glucopyranoside (660 mg, 1.05 mmol) and methanol:triethylamine:water (5:1:1; 6 mL) was stirred at room temperature for 12 hours. The reaction mixture was concentrated and the resulting residue was purified by silica gel column chromatography (chloroform:methanol=8:1) to give the titled compound (120 mg, 27%) as a colorless powder.

$^1$H-NMR (300 MHz, CD$_3$OD): δ 1.19 (t, J=7.6 Hz, 3H), 2.57 (q, J=7.6 Hz, 2H), 2.92 (ddd, J=3.6, 6.2, 10.2 Hz, 1H), 3.57 (dd, J=9.0, 10.2 Hz, 1H), 3.76 (dd, J=6.2, 11.3 Hz, 1H), 3.81 (t, J=8.9 Hz, 1H), 3.90-4.01 (m, 3H), 4.57 (s, 2H), 5.19 (d, J=8.7 Hz, 1H), 6.91 (m, 1H), 7.01 (m, 1H), 7.06 (m, JAB=8.3 Hz, 2H), 7.10 (m, JA8=8.3 Hz, 2H), 7.29 (s, 1H.).

ESI m/z=443 (M+Na).

mp 206.0-211.0° C.

Example 29 (Compound 22)

Preparation of 2'-[3'-(benzofuran-5'-yl)-1'-oxopropyl]-3'-hydroxy-5'-methylphenyl 5-thio-β-D-glucopyranoside 2,3,4,6-Tetra-O-acetyl-5-thio-D-glucopyranose (200 mg, 0.55 mmol), 2-acetyl-5-methylresorcinol (182 mg, 1.10 mmol), triphenylphosphine (288 mg, 1.10 mmol) and toluene (2 mL) were mixed, and to the resulting mixture, diisopropyl azodicarboxylate (40% in toluene, 555 mg) was then slowly added dropwise in ice. After stirring at room temperature for 18 hours, the reaction mixture was concentrated and the resulting residue was purified by silica gel column chromatography (hexane:ethyl acetate=70:30-50:50) to give 2-acetyl-3-hydroxy-5-methylphenyl 2,3,4,6-tetra-O-acetyl-5-thio-β-D-glucopyranoside (82 mg, 28%) as a light-yellow powder.

$^1$H-NMR (300 MHz, CDCl$_3$): δ 2.00 (s, 3H), 2.03 (s, 3H), 2.05 (s, 3H), 2.07 (s, 3H), 2.34 (s, 3H), 2.61 (s, 3H), 3.30-3.38 (m, 1H), 3.86 (s, 3H), 4.15 (dd, J=3.4 and 12.0 Hz, 1H), 4.35 (dd, J=5.0 and 12.0 Hz, 1H), 5.20 (dd, J=9.1 and 9.4 Hz, 1H), 5.39 (dd, J=9.4 and 9.6 Hz, 1H), 5.52 (d, J=8.9 Hz, 1H), 5.63 (dd, J=8.9 and 9.1 Hz, 1H), 6.42 (s, 1H), 6.50 (s, 1H), 13.14 (s, 1H).

ESI m/z=535 (M+Na).

mp 162.5-164.5° C.

Next, to a mixture of 2'-acetyl-3'-hydroxy-5'-methylphenyl 2,3,4,6-tetra-O-acetyl-5-thio-β-D-glucopyranoside (400 mg, 0.76 mmol) and ethanol (4 mL), 50% aqueous potassium hydroxide (450 μL) was added at room temperature. After stirring at room temperature for 5 minutes, 5-formylbenzofuran (125 mg, 0.86 mmol) was added at room temperature. After stirring at room temperature for an additional 22 hours, 4-(N,N-dimethylamino)pyridine (93 mg, 0.76 mmol) and 10% platinum/carbon (100 mg) were added and stirred under a hydrogen atmosphere at room temperature for 17.5 hours. After filtration to remove the insoluble materials, the filtrate was neutralized with 10% hydrochloric acid and filtered again to remove insoluble materials formed therein. The filtrate was extracted with ethyl acetate and dried over anhydrous magnesium sulfate. After the solvent was distilled off under reduced pressure, the resulting residue was purified by silica gel column chromatography (chloroform:methanol=10:1) to give 2-[3-(benzofuran-5-yl)-1-oxo-2-propenyl]-3-hydroxy-5-methylphenyl 5-thio-β-D-glucopyranoside (116 mg, 33%) as a light-yellow powder.

mp 170.5-177.5° C.

To a mixture of the thus obtained 2'-[3'-(benzofuran-5'-yl)-1'-oxo-2-propenyl]-3'-hydroxy-5'-methylphenyl 5-thio-β-D-glucopyranoside (105 mg, 0.23 mmol) and methanol (5 mL), 10% platinum/carbon (100 mg) was added and stirred under a hydrogen atmosphere at room temperature for 19 hours. After filtration to remove the insoluble materials, the filtrate was evaporated under reduced pressure and the resulting residue was purified by silica gel column chromatography (chloroform:methanol=20:1-9:1) to give the titled compound (47 mg, 43%).

$^1$H-NMR (300 MHz, DMSO-d$_6$): δ 2.27 (s, 3H), 2.90-3.02 (m, 2H), 3.08-3.18 (m, 1H), 3.27-3.40 (m, 3H), 3.52-3.60 (m, 2H), 3.75-3.85 (m, 1H), 4.06-4.13 (m, 1H), 4.73 (t, J=5.4 Hz, 1H), 5.04 (d, J=4.8 Hz, 1H), 5.09 (d, J=4.5 Hz, 1H), 5.36 (d, J=8.9 Hz, 1H), 5.44 (d, J=4.7 Hz, 1H), 6.38 (s, 1H), 6.71 (s, 1H), 6.88 (dd, J=0.9 and 2.2 Hz, 1H), 7.21 (dd, J=1.7 and 8.4 Hz, 1H), 7.47 (d, J=8.4 Hz, 1H), 7.52-7.56 (m, 1H), 7.94 (d, J=2.2 Hz, 1H), 11.88 (brs, 1H).

ESI m/z=497 (M+Na).

mp 171.0-175.0° C.

Example 30 (Compound 34)

2'-(p-Toluidino)phenyl 5-thio-β-D-glucopyranoside 2,3,4,6-Tetra-O-acetyl-5-thio-D-glucopyranose (500 mg, 1.37 mmol), 2-nitrophenol (382 mg, 2.74 mmol), triphenylphosphine (477 mg, 2.74 mmol) and toluene (2.5 mL) were mixed, and to the resulting mixture, diisopropyl azodicarboxylate (40% in toluene, 1.62 mL) was then slowly added dropwise in ice. After stirring at room temperature for 5.5 hours, the reaction mixture was concentrated and the resulting residue was purified by silica gel column chromatography (hexane:ethyl acetate=70:30) to give 2'-nitrophenyl 2,3,4,6-tetra-O-acetyl-5-thio-β-D-glucopyranoside (445 mg, 67%) as a light-yellow powder.

ESI m/z=508 (M+Na).

mp 170.0-171.5° C.

Next, 2'-nitrophenyl 2,3,4,6-tetra-O-acetyl-5-thio-β-D-glucopyranoside (445 mg, 0.917 mmol), methanol (4 mL) and 10% palladium/carbon (40 mg) were mixed and stirred under a hydrogen atmosphere at room temperature for 24 hours. After filtration to remove the insolubles, the filtrate was evaporated under reduced pressure to give 2'-aminophenyl 2,3,4,6-tetra-O-acetyl-5-thio-β-D-glucopyranoside (281 mg, 82%) as a light-brown amorphous substance.

ESI m/z=478 (M+Na).

Next, 2'-aminophenyl 2,3,4,6-tetra-O-acetyl-5-thio-β-D-glucopyranoside (65 mg, 0.143 mmol), 4-methylphenylboric acid (19 mg, 0.143 mmol), Cu(OAc)$_2$ (26 mg, 0.143 mmol), molecular sieves 4A (1 g) and toluene (1 mL) were mixed and stirred for 3 minutes, followed by addition of triethylamine (78 μl, 0.715 mmol) and pyridine (56 μl, 0.715 mmol). Stirring was continued at room temperature for 21 hours. After filtration to remove the insoluble materials, the filtrate was evaporated under reduced pressure and the resulting residue was purified by silica gel column chromatography (hexane:ethyl acetate=2:1) to give 2'-(p-toluidino)phenyl 2,3,4,6-tetra-O-acetyl-5-thio-β-D-glucopyranoside (67 mg, 86%).

ESI m/z=568(M+Na).

mp 112.0-115.0° C.

Next, to a mixture of 2'-(p-toluidino)phenyl 2,3,4,6-tetra-O-acetyl-5-thio-β-D-glucopyranoside (67 mg, 0.123 mmol), and methanol (1.0 mL), 1M NaOMe (12 μl, 0.012 mmol) was added and stirred at room temperature for 3 hours. The reaction mixture was neutralized with dry ice and concentrated. The resulting residue was purified by silica gel column chromatography (chloroform:methanol=10:1) to give the titled compound (24 mg, 53%).

$^1$H-NMR (300 MHz, CD$_3$OD): δ 2.27 (s, 3H), 2.89 (m, 1H), 3.27 (t, J=9.0 Hz, 1H), 3.57 (t, J=9.0, 10.2 Hz, 1H), 3.80 (m, 1H), 3.84 (t, J=9.0 Hz, 1H), 3.93 (m, 1H), 4.96 (d, J=9.0 Hz, 1H), 6.74 (m, 1H), 6.90 (m, 1H), 7.05 (m, 4H), 7.17 (m, 1H), 7.24 (m, 1H).

ESI m/z=400(M+Na).

mp 152.0-153.0° C.

Using the corresponding starting materials and reactants, the same procedures as shown in the above examples were repeated to give the following compounds according to the present invention, which are summarized in Table 1 below, along with the compounds obtained in the above examples.

| Compound No. | Chemical structure | $^1$NMR, MS, mp |
|---|---|---|
| Compound 1 | 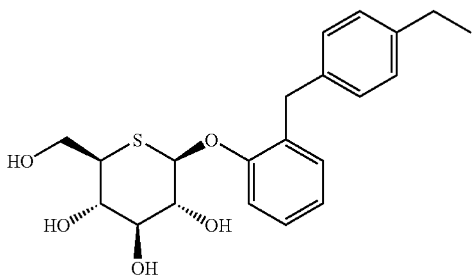 | $^1$H-NMR(300MHz, CD$_3$OD): δ 1.19(t, J=7.3Hz, 3H), 2.58 (q, J=7.3Hz, 2H), 2.88-2.95(m, 1H), 3.29-3.31(m, 1H), 3.55-3.60(m, 1H), 3.74-3.83(m, 2H), 3.90-3.93(m, 1H), 3.97-3.99(m, 2H), 5.17(d, J=8.5Hz, 1H), 6.91(dt, J=1.2, 7.4Hz, 1H), 7.10-7.19(m, 6H), 7.27(d, J=7.9Hz, 1H). ESI m/z = 389(M − H) mp 154.0-169.0° C. |
| Compound 2 | 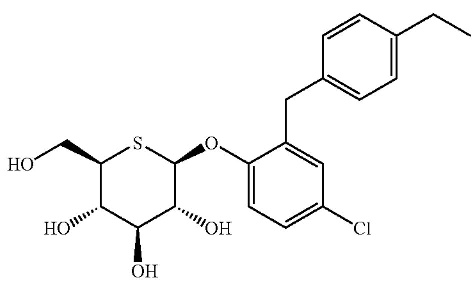 | $^1$H-NMR(300MHz, CD$_3$OD): δ 1.20(t, J=7.6Hz, 3H), 2.60 (q, J=7.6Hz, 2H), 2.87-2.97(m, 1H), 3.27-3.33(m, 1H), 3.57(dd, J=9.1, 10.1Hz, 1H), 3.73-3.84(m, 2H), 3.87-4.00(m, 3H), 5.16(d, J=8.7Hz, 1H), 6.96(d, J=2.6Hz, 1H), 7.08-7.14(m, 4H), 7.15(dd, J=2.6, 8.9Hz, 1H), 7.27 (d, J=8.9Hz, 1H). ESI m/z = 423(M − H) mp 173.5-177.5° C. |
| Compound 3 | 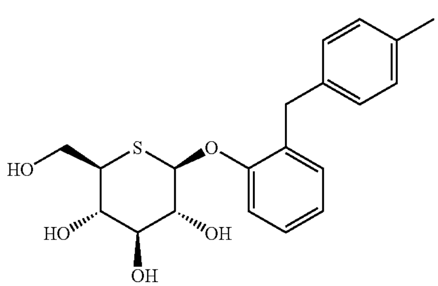 | $^1$H-NMR(300MHz, CD$_3$OD): δ 2.27(s, 3H), 2.88-2.95(m, 1H), 3.28-3.31(m, 1H), 3.57(dd, J=9.2, 10.4Hz, 1H), 3.74-3.83(m, 2H), 3.90-3.95(m, 3H), 5.16(d, J=8.5Hz, 1H), 6.88-7.20(m, 8H). ESI m/z = 399(M + Na) mp 184.0-186.0° C. |

-continued

| Compound No. | Chemical structure | ¹NMR, MS, mp |
|---|---|---|
| Compound 4 | 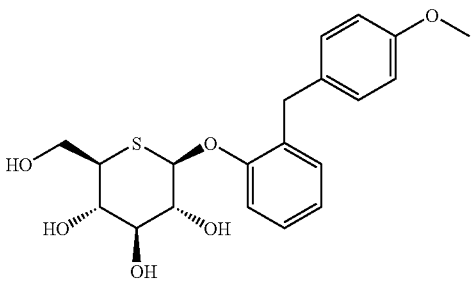 | ¹H-NMR(300MHz, CD$_3$OD): δ 2.91-2.93(m, 1H), 3.29-3.34(m, 1H), 3.58(dd, J=9.2, 10.4Hz, 1H), 3.74(s, 3H), 3.77-3.81(m, 2H), 3.84-3.95(m, 3H), 5.17(d, J=8.7Hz, 1H), 6.78-7.28(m, 8H).<br>ESI m/z = 415(M + Na)<br>mp 166.0-167.5° C. |
| Compound 5 | 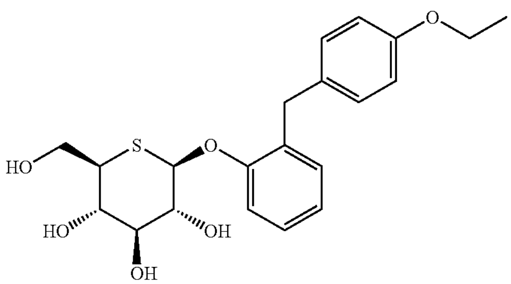 | ¹H-NMR(300MHz, CD$_3$OD): δ 1.35(t, J=7.0Hz, 3H), 2.88-2.95(m, 1H), 3.26- 3.31(m, 1H), 3.57(dd, J= 9.2, 9.8Hz, 1H), 3.74-3.84(m, 2H), 3.90-4.01(m, 5H), 5.17(d, J=8.7Hz, 1H), 6.77-7.28(m, 8H)<br>ESI m/z = 429(M + Na)<br>mp 182.0-183.5° C. |
| Compound 6 | 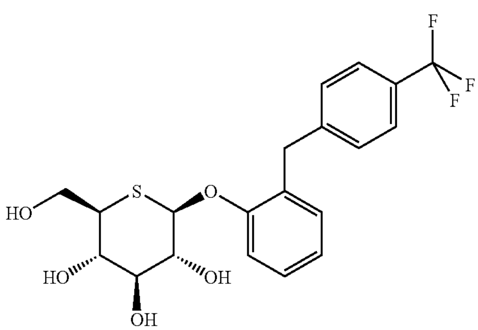 | ¹H-NMR(300MHz, CD$_3$OD): δ 2.88-2.95(m, 1H), 3.29-3.32(m, 1H), 3.56(dd, J=9.0, 10.3Hz, 1H), 3.72-3.89(m, 2H), 3.89-3.94(m, 1H), 4.02-4.08(m, 2H), 5.20(d, J=8.9Hz, 1H), 7.10-7.32(m, 3H), 7.39-7.53(m, 4H).<br>ESI m/z = 454(M + Na)<br>mp 164.0-165.0° C. |
| Compound 7 | 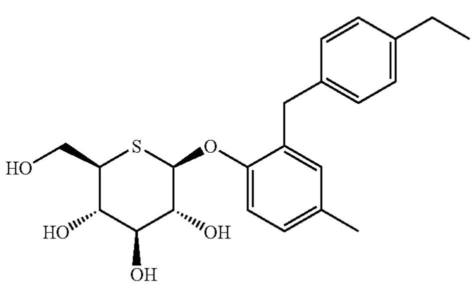 | ¹H-NMR(300MHz, CD$_3$OD): δ 1.19(t, J=7.6Hz, 3H), 2.21(s, 3H), 2.58(q, J=7.6Hz, 2H), 2.85-2.93(m, 1H), 3.27-3.32(m, 1H), 3.55(dd, J= 9.2, 10.4Hz, 1H), 3.73-3.83(m, 2H), 3.88-3.95(m, 3H), 5.11(d, J=8.7Hz, 1H), 6.85(d, J=1.8Hz, 1H), 6.97(dd, J=1.8, 8.6Hz, 1H), 7.05-7.16(m, 3H).<br>ESI m/z = 427(M + Na)<br>mp 154.0-156.0° C. |
| Compound 8 | 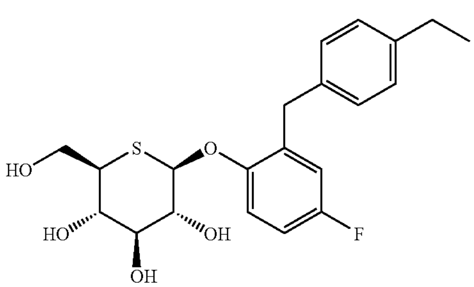 | ¹H-NMR(300MHz, CD$_3$OD): δ 1.20(t, J=7.6Hz, 3H), 2.59(q, J=7.6Hz, 2H), 2.87-2.93(m, 1H), 3.25-3.32(m, 1H), 3.57(dd, J=9.0, 10.2Hz, 1H), 3.74-3.90(m, 2H), 3.91-3.96(m, 3H), 5.12(d, J=8.7Hz, 1H), 6.71(dd, J=3.1, 9.5Hz, 1H), 6.85-6.91(m, 1H), 7.08-7.14(m, 4H), 7.25-7.29(m, 1H).<br>ESI m/z = 431(M + Na)<br>mp 163.0-165.5° C. |

-continued

| Compound No. | Chemical structure | ¹NMR, MS, mp |
|---|---|---|
| Compound 9 | 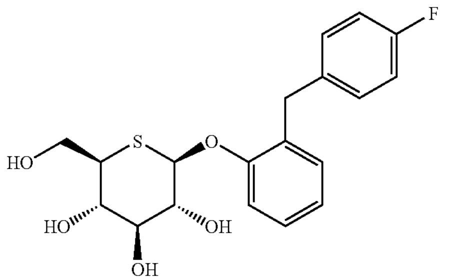 | ¹H-NMR(300MHz, CD₃OD): δ 2.88-2.95(m, 1H), 3.26-3.32(m, 1H), 3.57(dd, J=9.0, 10.1Hz, 1H), 3.73-3.84(m, 2H), 3.84-4.06(m, 3H), 5.19(d, J=8.7Hz, 1H), 6.89-6.98(m, 3H), 6.89-6.98 (m, 3H), 7.05-7.19(m, 1H), 7.21-7.29(m, 4H) ESI m/z = 403(M + Na) mp 157.0-158.5° C. |
| Compound 10 | 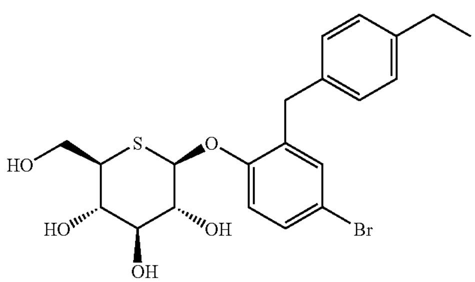 | ¹H-NMR(300MHz, CD₃OD): δ 1.20(t, J=7.6Hz, 3H), 2.59(q, J=7.6Hz, 2H), 2.90-2.93(m, 1H), 3.25-3.33(m, 1H), 3.57(dd, J=9.1, 10.3Hz, 1H), 3.78-3.84(m, 2H), 3.90-3.95(m, 3H), 5.15(d, J=8.7Hz, 1H), 7.11-7.12(m, 5H), 7.21(d, J=8.8Hz, 1H), 7.28(dd, J=2.4, 8.8Hz, 1H). ESI m/z = 493(M + Na) mp 172.0-173.5° C. |
| Compound 11 | 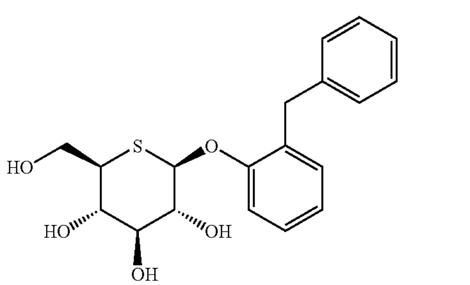 | ¹H-NMR(300MHz, CD₃OD): δ 2.88-2.95(m, 1H), 3.26-3.32(m, 1H), 3.57(dd, J=9.2, 10.1Hz, 1H), 3.74-3.84(m, 2H), 3.90-4.07(m, 3H), 5.18(d, J=8.7Hz, 1H), 6.89-6.94(m, 1H), 7.04-7.06 (m, 1H), 7.11-7.30(m, 7H). ESI m/z = 385(M + Na) mp 171.0-174.0° C. |
| Compound 12 | 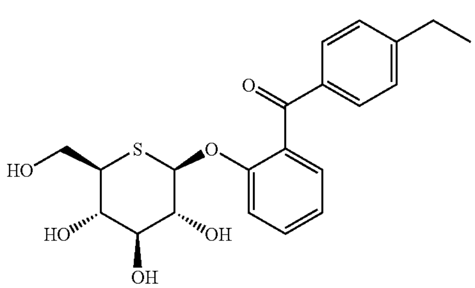 | ¹H-NMR(300MHz, CD₃OD): δ 1.27(t, J=7.6Hz, 3H), 2.73(q, J=7.6Hz, 2H), 2.95(m, 1H), 3.47(dd, J=9.0, 10.1Hz, 1H), 3.54(t, J=8.7Hz, 1H), 3.74 (dd, J=6.2, 11.4Hz, 1H), 3.92(dd, J=3.9, 11.4Hz, 1H), 5.20(d, J=8.7Hz, 1H), 7.13(dt, J=1.4, 6.8Hz, 1H), 7.30-7.35(m, 3H), 7.48-7.58(m, 2H), 7.71(d, J=847Hz, 2H). ESI m/z = 427(M + Na) |
| Compound 13 | 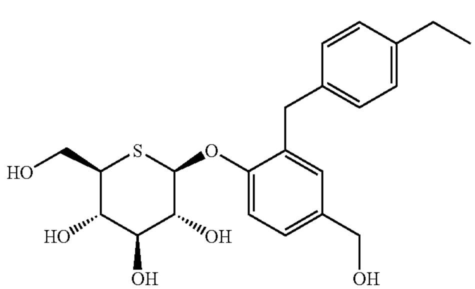 | ¹H-NMR(300MHz, CD₃OD): δ 1.19(t, J=7.6Hz, 3H), 2.57(q, J=7.6Hz, 2H), 2.87-2.95(m, 1H), 3.28-3.33(m, 1H), 3.57(dd, J=8.9, 10.3Hz, 1H), 3.73-3.83(m, 2H), 3.88-4.03(m, 3H), 4.47(s, 2H), 5.17(d, J=8.7Hz, 1H), 7.04-7.19(m, 6H), 7.25(d, J=8.4Hz, 1H). ESI m/z = 443(M + Na) mp 202.5-205.0° C. |

| Compound No. | Chemical structure | $^1$NMR, MS, mp |
|---|---|---|
| Compound 14 | 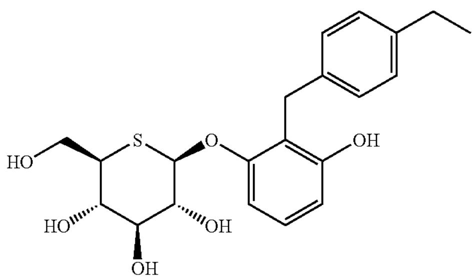 | $^1$H-NMR(300MHz, CD$_3$OD): δ 1.17(t, J=7.6Hz, 3H), 2.55(q, J=7.6Hz, 2H), 2.83-2.91(m, 1H), 3.22-3.30(m, 1H), 3.57(dd, J=9.2, 9.9Hz, 1H), 3.71-3.82(m, 2H), 3.89(d, J=14.3Hz, 1H), 3.90 (dd, 3.7, 11.2Hz, 1H), 4.04(d, J=14.3Hz, 1H), 5.17(d, J=8.7Hz, 1H), 6.50(d, J=8.0Hz, 1H), 6.78(d, J=8.4Hz, 1H), 6.95-7.00(m, 1H), 6.99 (d, J=8.1Hz, 2H), 7.15(d, J=8.1Hz, 2H). ESI m/z = 429(M + Na) mp 238.0-242.5° C. |
| Compound 15 | 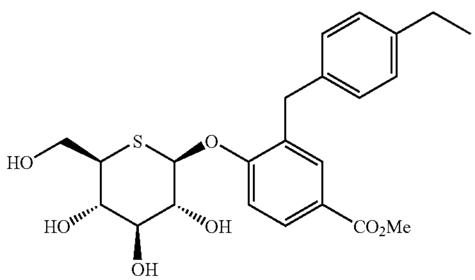 | $^1$H-NMR(300MHz, CD$_3$OD): δ 1.20(t, J=7.6Hz, 3H), 2.59(q, J=7.6Hz, 2H), 2.93-3.03(m, 1H), 3.54-3.64(m, 1H), 3.83(s, 1H), 3.75-4.08(m, 1H), 5.30(d, J=8.7Hz, 1H), 7.07-7.15(m, 4H), 7.37(d, J=8.8Hz, 1H), 7.75(d, J=2.2Hz, 1H), 7.87(dd, J=2.2, 8.8Hz, 1H). ESI m/z = 471(M + Na) mp 196.0-198.0° C. |
| Compound 16 | 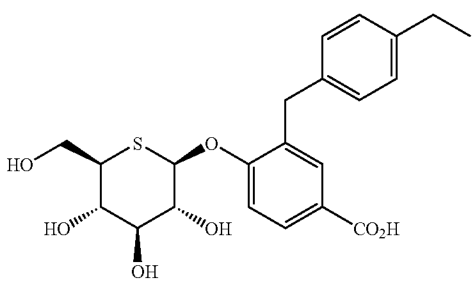 | $^1$H-NMR(300MHz, CD$_3$OD): δ 1.20(t, J=7.7Hz, 3H), 2.59(q, J=7.7Hz, 2H), 2.93-3.03(m, 1H), 3.28-3.35(m, 1H), 3.55-3.64(m, 1H), 3.74-4.08(m, 1H), 5.30(d, J=8.7Hz, 1H), 7.07-7.17 (m, 4H), 7.38(d, J=8.5Hz, 1H), 7.74(d, J=2.0Hz, 1H), 7.88(dd, J=2.0, 8.5Hz, 1H). ESI m/z = 457(M + Na) mp 219.0-220.5° C. |
| Compound 17 | 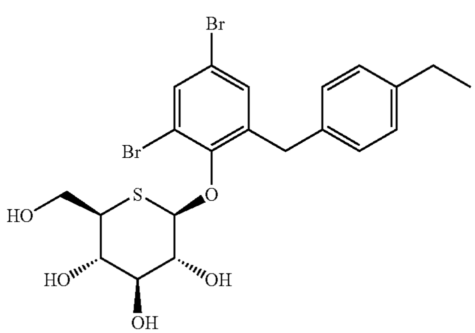 | $^1$H-NMR(300MHz, CD$_3$OD): δ 1.21(t, J=7.6Hz, 3H), 2.54-2.64(m, 3H), 3.19(t, J=8.9Hz, 1H), 3.54(dd, J=9.0, 10.4Hz, 1H), 3.72(dd, J=6.2, 11.5Hz, 1H), 3.87(dd, J=3.6, 11.3Hz, 1H), 3.92 (t, J=8.9Hz), 4.05(d, J=15.7Hz, 2H), 4.21(d, J=15.7Hz, 2H), 5.35(d, J=9.0Hz, 1H), 7.09-7.15(m, 5H), 7.59(d, J=2.5Hz, 1H). ESI m/z = 429(M + Na) |
| Compound 18 | 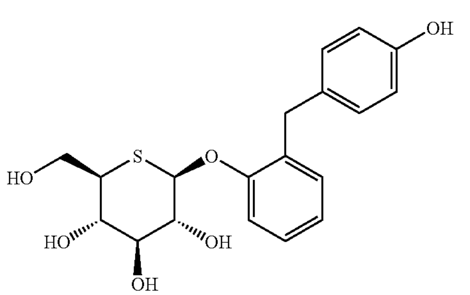 | $^1$H-NMR(300MHz, CD$_3$OD): δ 2.85-2.95(m, 1H), 3.23-3.33(m, 1H), 3.57(dd, J=9.2, 10.4Hz, 1H), 3.73-3.85(m, 2H), 3.88-3.97(m, 3H), 5.16(d, J=8.5Hz, 1H), 6.63-6.70(m, 2H), 6.86-6.93(m, 1H), 6.98-7.05(m, 3H), 7.13-7.20(m, 1H), 7.23-7.30(m, 1H). ESI m/z = 401(M + Na) mp 189.5.0-191.0° C. |

-continued

| Compound No. | Chemical structure | ¹NMR, MS, mp |
|---|---|---|
| Compound 19 | 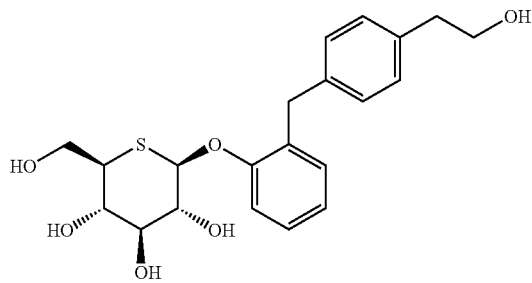 | ¹H-NMR(300MHz, CD$_3$OD): δ 2.76(t, J=7.0Hz, 1H), 2.85-2.95(m, 1H), 3.23-3.33(m, 1H), 3.56(dd, J=9.1, 10.2Hz, 1H), 3.71(t, J=7.0Hz, 2H), 3.73-3.83(m, 2H), 3.88-4.05(m, 2H), 5.16(d, J=8.7Hz, 1H), 6.85-6.95(m, 1H), 7.03-7.20(m, 6H), 7.24-7.30(m, 1H).<br>ESI m/z = 429(M + Na)<br>mp 154.5.0-156.5° C. |
| Compound 20 | 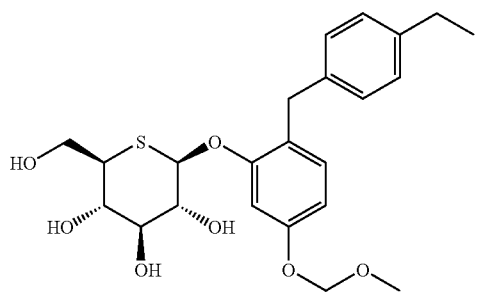 | ¹H-NMR(300MHz, CD$_3$OD): δ 1.19(t, J=7.6Hz, 3H), 2.58(q, J=7.6Hz, 2H), 2.88-2.97(m, 1H), 3.28-3.33(m, 1H), 3.44(s, 3H), 3.56(dd, J=9.0, 10.3Hz, 1H), 3.72-3.82(m, 2H), 3.83-3.96(m, 3H), 5.12-5.17(m, 3H), 6.62(dd, J=2.4, 8.4Hz, 1H), 6.93(d, J=8.4Hz, 1H), 6.97(d, J=2.4Hz, 1H), 7.03-7.12(m, 4H).<br>ESI m/z = 473(M + Na)<br>mp 175.5-180.0° C. |
| Compound 21 | 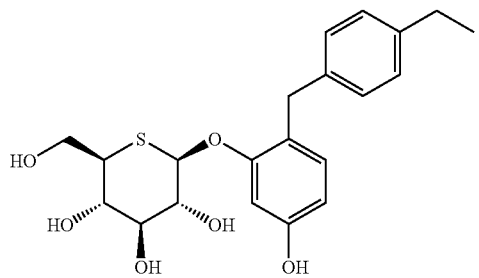 | ¹H-NMR(300MHz, CD$_3$OD): δ 1.19(t, J=7.6Hz, 3H), 2.57(q, J=7.6Hz, 2H), 2.85-2.94(m, 1H), 3.24-3.33(m, 1H), 3.56(dd, J=9.0, 10.3Hz, 1H), 3.73-3.90(m, 2H), 3.92(dd, J=3.7, 7.8Hz, 3H), 5.08(d, J=8.7Hz, 1H), 6.37(dd, J=2.3, 8.2Hz, 1H), 6.76(d, J=2.3Hz, 1H), 6.83(d, J=8.2Hz, 1H), 7.00-7.10(m, 4H).<br>ESI m/z = 429(M + Na)<br>mp 172.0-173.5° C. |
| Compound 22 | 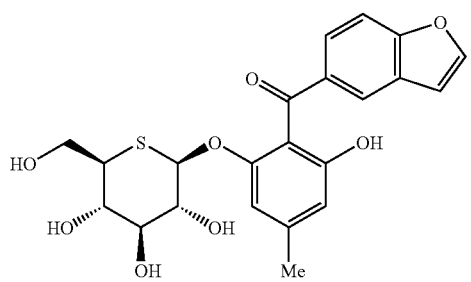 | ¹H-NMR(300MHz, CD$_3$OD): δ 2.27(s, 3H), 2.90-3.02(m, 2H), 3.08-3.18(m, 1H), 3.27-3.40(m, 3H), 3.52-3.60(m, 2H), 3.75-3.85(m, 1H), 4.06-4.13(m, 1H), 4.73(t, J=5.4Hz, 1H), 5.04(d, J=4.8Hz, 1H), 5.09(d, J=4.5Hz, 1H), 5.36(d, J=8.9Hz, 1H), 5.44(d, J=4.7Hz, 1H), 6.38(s, 1H), 6.71(s, 1H), 6.88(dd, J=0.9, 2.2Hz, 1H), 7.21(dd, J=1.7, 8.4Hz, 1H), 7.47(d, J=8.4Hz, 1H), 7.52-7.56(m, 1H), 7.94(d, J=2.2Hz, 1H), 11.8(brs, 1H).<br>ESI m/z = 497(M + Na), mp 171.0-175.0° C. |
| Compound 23 | 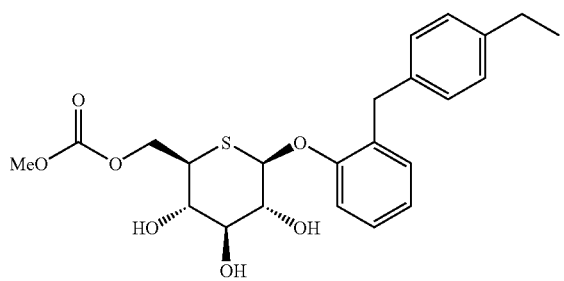 | ¹H-NMR(300MHz, CD$_3$OD): δ 1.19(t, J=7.6Hz, 3H), 2.58(q, J=7.6Hz, 2H), 3.04-3.14(m, 1H), 3.26-3.34(m, 1H), 3.57(dd, J=9.2, 10.3Hz, 1H), 3.74(s, 3H), 3.76-3.85(m, 1H), 3.92(d, J=14.0 Hz, 1H), 3.99(d, J=14.0Hz, 1H), 4.35(dd, J= 6.2, 11.3Hz, 1H), 4.48(dd, J=3.3, 11.3Hz, 1H), 5.19(d, J=8.7Hz, 1H), 6.88-6.95(m, 1H), 7.02-7.28(m, 7H).<br>ESI m/z = 471(M + Na)<br>mp 102.0-104.5° |

-continued

| Compound No. | Chemical structure | ¹NMR, MS, mp |
|---|---|---|
| Compound 24 | 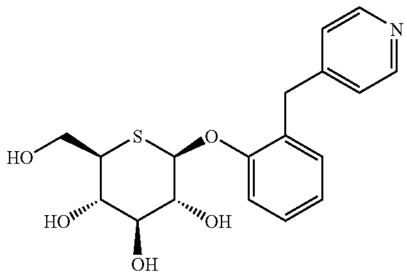 | ESI m/z = 389(M + Na)<br>mp 179.0-180.0° C. |
| Compound 25 | 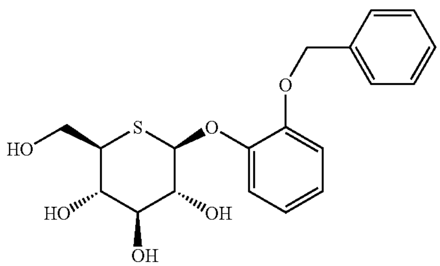 | ESI m/z = 401(M + Na)<br>mp 148.0-150.0° C. |
| Compound 26 | 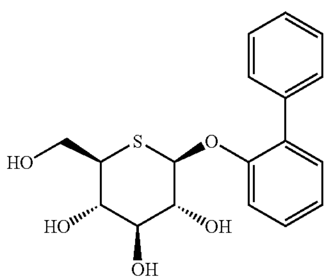 | ¹H-NMR(300MHz, CD3OD): δ 2.87(ddd, J=3.6, 6.0, 10.1Hz, 1H), 3.26(dd, J=8.7, 9.0Hz, 1H), 3.51 (dd, J=9.0, 10.1Hz, 1H), 3.67(t, J=8.7Hz, 1H), 3.73(dd, J=6.0, 11.3Hz, 1H), 3.89(dd, J=3.6, 11.3Hz, 1H), 5.25(d, J=8.7Hz, 1H), 7.08(m, 1H), 7.25-7.41(m, 6H), 7.53-7.56(m, 2H)<br>ESI m/z = 371(M + Na) |
| Compound 27 | 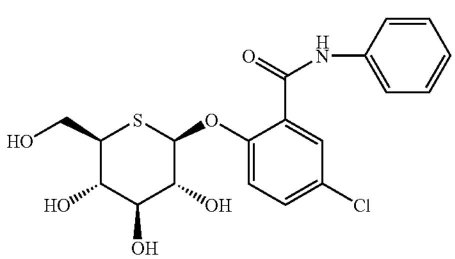 | ESI m/z = 448, 459(M + Na)<br>mp 96.0-105.0° C. |
| Compound 28 | 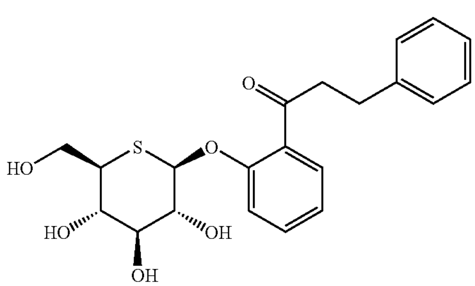 | ¹H-NMR(300MHz, CD3OD): δ 2.95-3.08(m, 3H), 3.29-3.40(m, 3H), 3.56(t, J=8.9Hz, 1H), 3.78-3.85(m, 2H), 3.94(dd, J=3.9, 11.8Hz, 1H), 5.33(d, J=8.9Hz, 1H), 7.05-7.25(m, 6H), 7.45-7.55(m, 3H).<br>ESI m/z = 427(M + Na) |

-continued

| Compound No. | Chemical structure | ¹NMR, MS, mp |
|---|---|---|
| Compound 29 | (structure) | ESI m/z = 413(M + Na)<br>mp 82.0-86.0° C. |
| Compound 30 | (structure) | ESI m/z = 429(M + Na) |
| Compound 31 | (structure) | ESI m/z = 481, 483(M + Na)<br>mp 72.0-80.0° C. |
| Compound 32 | (structure) | ¹H-NMR(300MHz, CD3OD): δ 1.21(t, J=7.6 Hz, 3H), 2.61(q, J=7.6Hz, 2H), 2.68-2.70(m, 1H), 3.20-3.30(m, 1H), 3.45(dd, J=1.2, 10.3Hz, 1H), 3.70-3.79(m, 2H), 3.80-3.94(m, 1H), 4.00(d, J=15.5Hz, 1H), 4.13(d, J=15.5Hz, 1H), 5.18(d, J=8.9Hz, 1H), 6.49-6.61(m, 1H), 6.82-6.87(m, 1H), 7.12(bs, 4H).<br>ESI m/z = 449(M + Na) |
| Compound 33 | (structure) | ¹H-NMR(300MHz, CD3OD): δ 2.86(ddd, J=3.7, 6.2, 11.5Hz, 1H), 3.26(t, J=8.9 Hz, 1H), 3.53(t, J=8.9Hz, 1H), 3.71(t, J=8.9Hz, 1H), 3.75(dd, J=6.2, 11.5Hz, 1H), 3.90(dd, J=3.7, 11.5Hz, 1H), 5.18(d, J=8.9Hz, 1H), 6.82(m, 2H), 6.89(dd, J=1.6, 8.2Hz, 1H), 6.99(dt, J=1.6, 8.2Hz, 1H), 7.07-7.13(m, 3H), 7.37(dd, J=1.6, 8.2Hz, 1H).<br>ESI m/z = 401(M + Na) |

-continued

| Compound No. | Chemical structure | ¹NMR, MS, mp |
|---|---|---|
| Compound 34 | 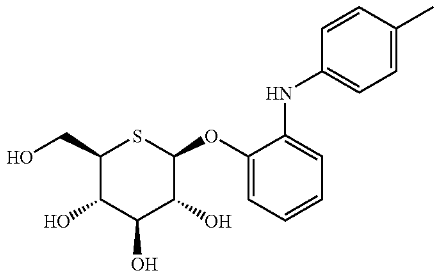 | ¹H-NMR(300MHz, CD3OD): δ 2.27(s, 3H), 2.89 (m, 1H), 3.27(t, J=9.0Hz, 1H), 3.57(t, J= 9.0, 10.2Hz, 1H), 3.80(m, 1H), 3.84(t, J= 9.0Hz, 1H), 3.93(m, 1H), 4.96(d, J=9.0Hz, 1H), 6.74(m, 1H), 6.90(m, 1H), 7.05(m, 4H), 7.17(m, 1H), 7.24(m, 1H). ESI m/z = 400(M + Na) mp 152.0-153.0° C. |
| Compound 35 | 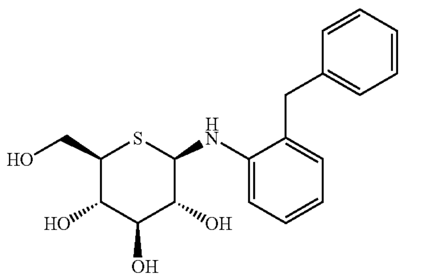 | a mixture of α anomer:β anomer = 9:5 ESI m/z = 384(M + Na) mp 144.0-151.0° C. |
| Compound 36 | 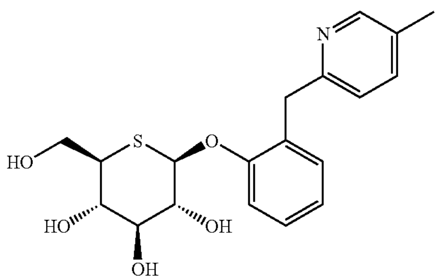 | ESI m/z = 400(M + Na) mp 177.0-180.0° C. |
| Compound 37 | 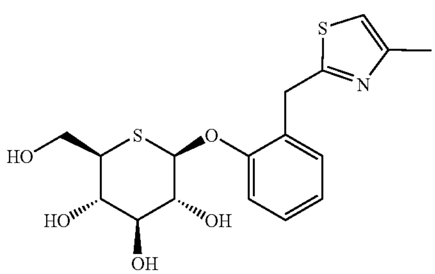 | ESI m/z = 406(M + Na) mp 197.0-200.0° C. |
| Compound 38 | 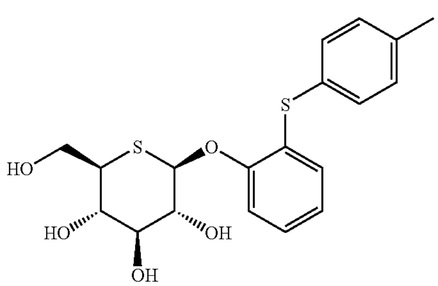 | ESI m/z = 417(M + Na) mp 140.0-142.0° C. |

-continued
| Compound No. | Chemical structure | ¹NMR, MS, mp |
|---|---|---|
| Compound 39 | 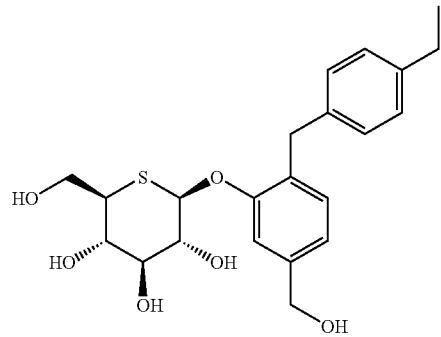 | ¹H-NMR(300MHz, CD₃OD): δ 1.19(t, J=7.6Hz, 3H), 2.57(q, J=7.6Hz, 2H), 2.92 (ddd, J=3.6, 6.2, 10.2Hz, 1H), 3.57(dd, J= 9.0, 10.2Hz, 1H), 3.76(dd, J=6.2, 11.3Hz, 1H), 3.81(t, J=8.9Hz, 1H), 3.90-4.01(m, 3H), 4.57(s, 2H), 5.19(d, J=8.7Hz, 1H), 6.91(m, 1H), 7.01(m, 1H), 7.06(m, J$_{AB}$ = 8.3Hz, 2H), 7.10(m, J$_{AB}$ = 8.3Hz, 2H), 7.29(s, 1H). ESI m/z = 443(M + Na). mp 206.0-211.0° C. |
| Compound 40 | 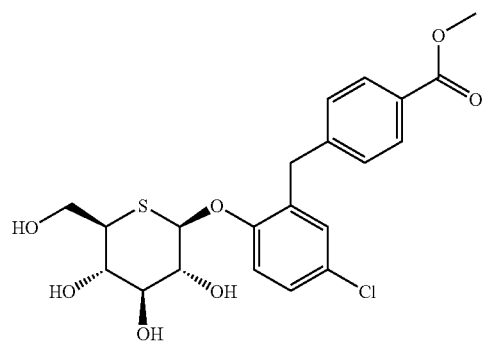 | ESI m/z = 443(M + Na) mp 74.0-76.0° C. |
| Compound 41 | 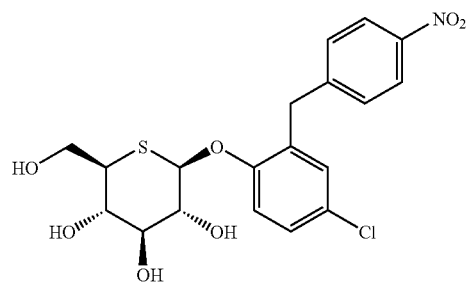 | ESI m/z = 464, 466(M + Na) mp 180.0-182.0° C. |
| Compound 42 | 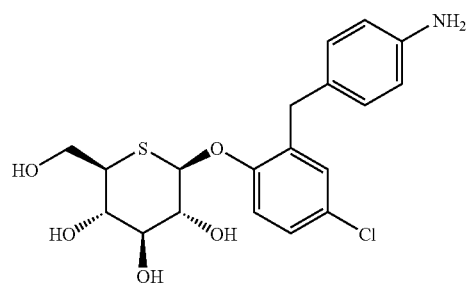 | ESI m/z = 434, 436(M + Na) mp 206.0-208.0° C. |

-continued

| Compound No. | Chemical structure | ¹NMR, MS, mp |
|---|---|---|
| Compound 43 | 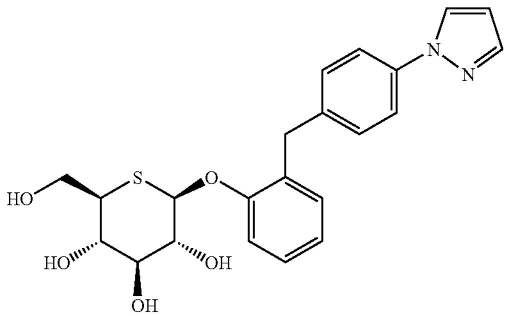 | ESI m/z = 451(M + Na)<br>mp 208.0-210.0° C. |
| Compound 44 | 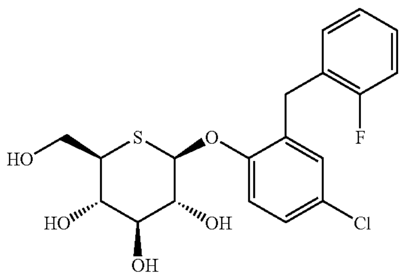 | ESI m/z = 437, 439(M + Na)<br>mp 170.0-173.0° C. |
| Compound 45 | 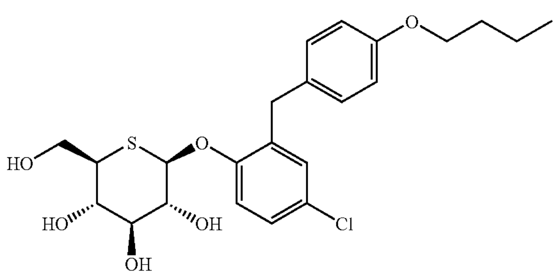 | ESI m/z = 491, 493(M + Na)<br>mp 166.0-169.0° C. |
| Compound 46 | 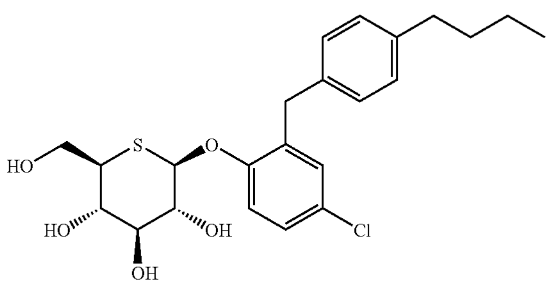 | ESI m/z = 475, 477(M + Na)<br>mp 165.0-168.0° C. |
| Compound 47 | 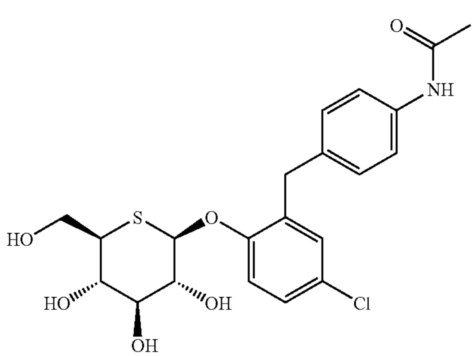 | ESI m/z = 476, 478(M + Na)<br>mp 235.0-236.5° C. |

-continued

| Compound No. | Chemical structure | ¹NMR, MS, mp |
|---|---|---|
| Compound 48 | 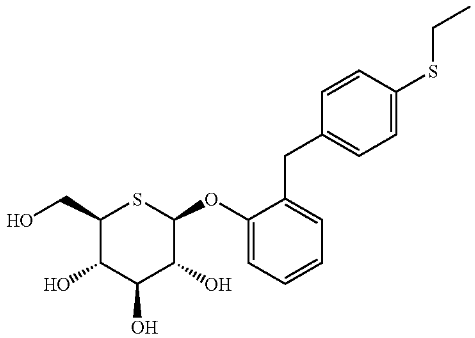 | ESI m/z = 445(M + Na)<br>mp 174.0-176.5° C. |
| Compound 49 | 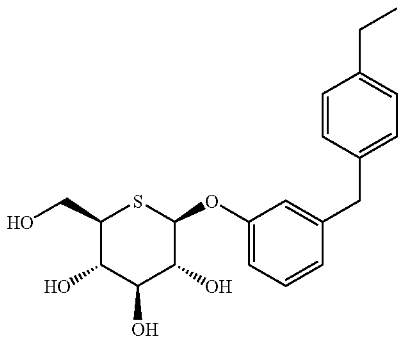 | ESI m/z = 413(M + Na)<br>mp 132.0-134.0° C. |
| Compound 50 | 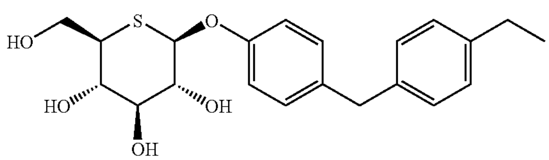 | ESI m/z = 413(M + Na)<br>mp 137.0-138.5° C. |
| Compound 51 | 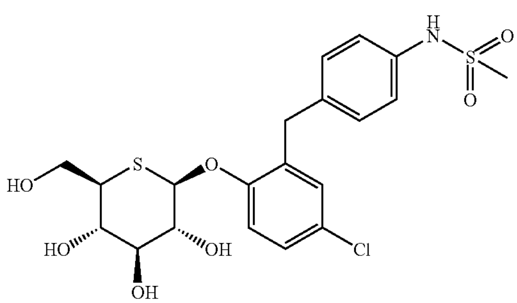 | ESI m/z = 680, 682(M + Na)<br>mp 151.0-153.0° C. |
| Compound 52 | 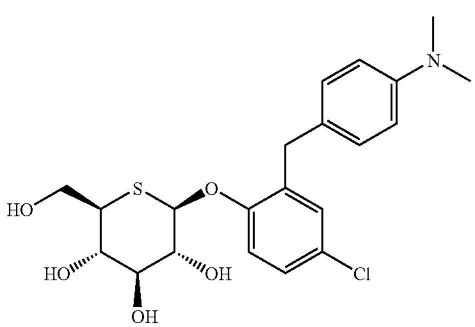 | ESI m/z = 462, 464(M + Na)<br>mp 183.0-184.0° C. |

-continued

| Compound No. | Chemical structure | $^1$NMR, MS, mp |
|---|---|---|
| Compound 53 | 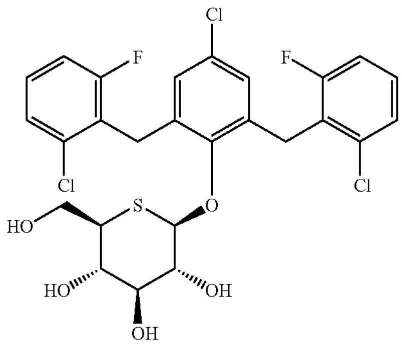 | ESI m/z = 613, 615, 617, 619(M + Na)<br>mp 112.0-118.0° C. |
| Compound 54 | 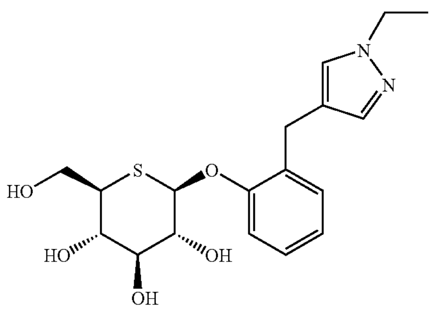 | ESI m/z = 403(M + Na)<br>mp 175.0-177.5° C. |
| Compound 55 | 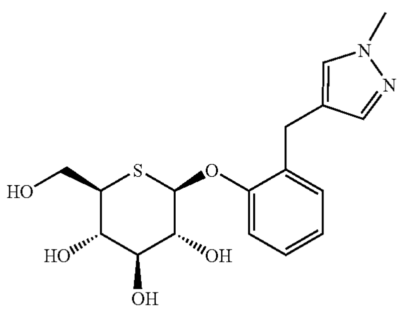 | ESI m/z = 389(M + Na)<br>mp 148.5-149.5° C. |
| Compound 56 | 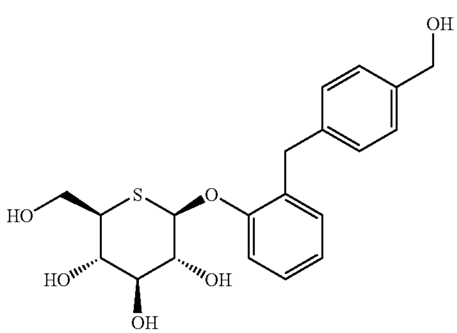 | ESI m/z = 415(M + Na)<br>mp 184.0-186.5° C. |
| Compound 57 | 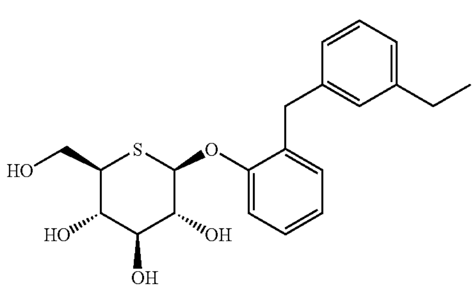 | ESI m/z = 413(M + Na)<br>mp 144.0-145.0° C. |

-continued

| Compound No. | Chemical structure | ¹NMR, MS, mp |
|---|---|---|
| Compound 58 | 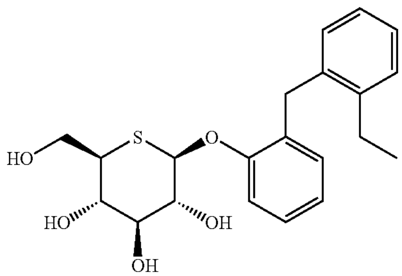 | ESI m/z = 413(M + Na)<br>mp 96.0-101.0° C. |
| Compound 59 | 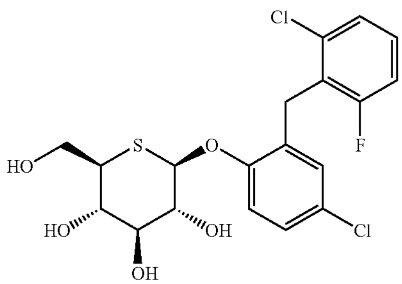 | ESI m/z = 471, 473(M + Na)<br>mp 183.5-185.0° C. |
| Compound 60 | 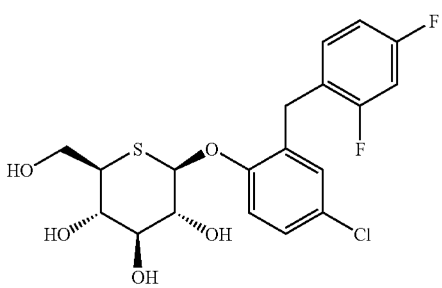 | ESI m/z = 455, 457(M + Na)<br>mp 175.5-177.0° C. |
| Compound 61 | 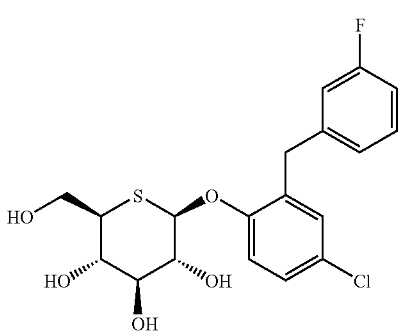 | ESI m/z = 437, 439(M + Na)<br>mp 182.0-183.0° C. |

| Compound No. | Chemical structure | ¹NMR, MS, mp |
|---|---|---|
| Compound 62 | 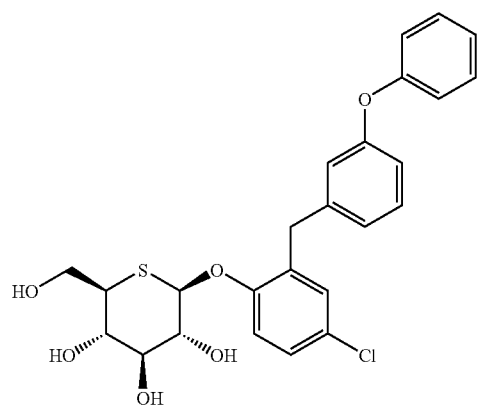 | ESI m/z = 511, 513(M + Na)<br>mp 124.5-127.0° C. |
| Compound 63 | 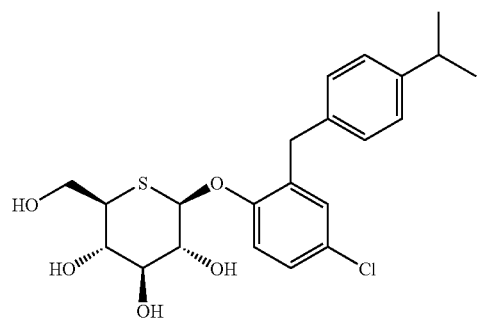 | ESI m/z = 461, 463(M + Na)<br>mp 146.0-148.5° C. |
| Compound 64 | 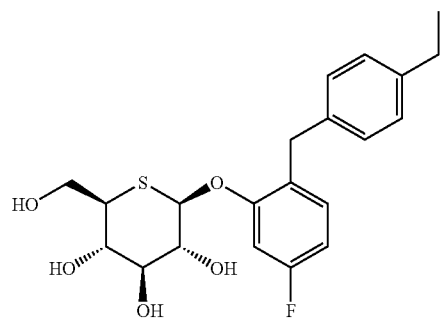 | ESI m/z = 431(M + Na)<br>mp 156.0-157.0° C. |
| Compound 65 | 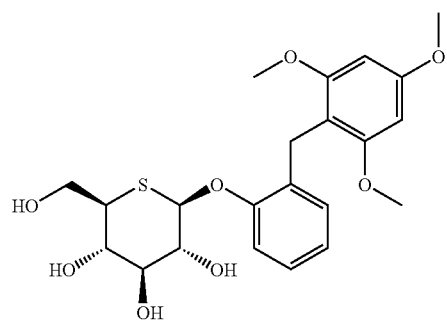 | ESI m/z = 475(M + Na)<br>mp 100.0-105.0° C. |

-continued

| Compound No. | Chemical structure | ¹NMR, MS, mp |
|---|---|---|
| Compound 66 | 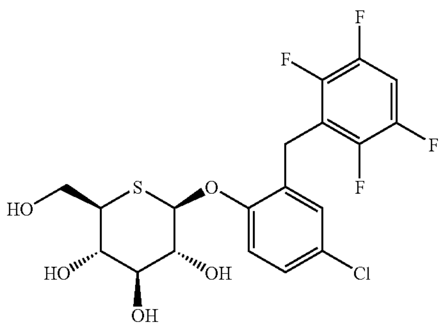 | ESI m/z = 491, 493(M + Na)<br>mp 204.0-211.0° C. |
| Compound 67 | 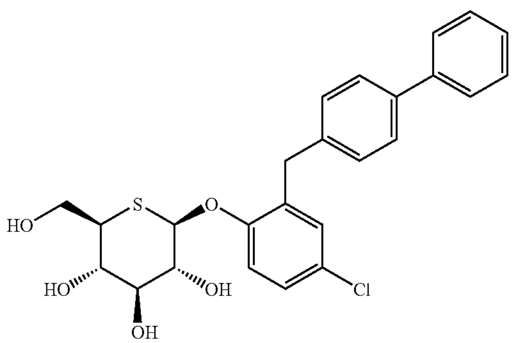 | ESI m/z = 495, 497(M + Na)<br>mp 187.0-195.0° C. |
| Compound 68 | 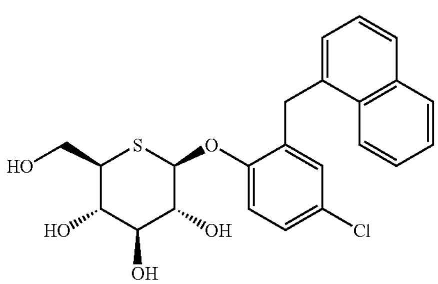 | ESI m/z = 469, 471(M + Na)<br>mp 170.0-175.0° C. |
| Compound 69 | 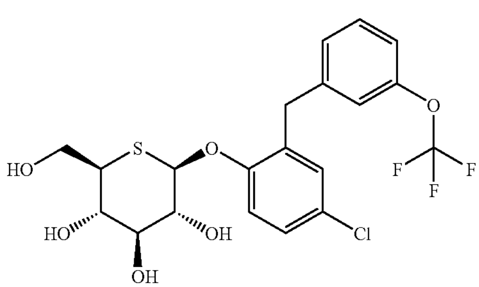 | ESI m/z = 503, 505(M + Na)<br>mp 146.0-148.0° C. |
| Compound 70 | 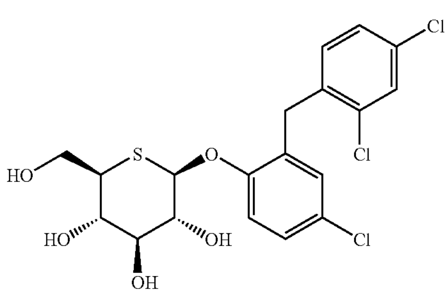 | ESI m/z = 487, 489, 491, 493(M + Na)<br>mp 172.0-174.0° C. |

-continued
| Compound No. | Chemical structure | ¹NMR, MS, mp |
|---|---|---|
| Compound 71 | 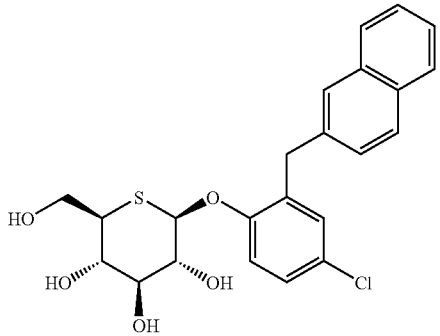 | ESI m/z = 469, 471(M + Na)<br>mp 192.0-194.0° C. |
| Compound 72 | 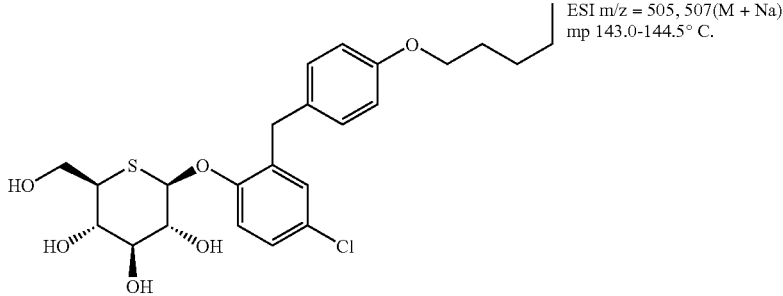 | ESI m/z = 505, 507(M + Na)<br>mp 143.0-144.5° C. |
| Compound 73 | 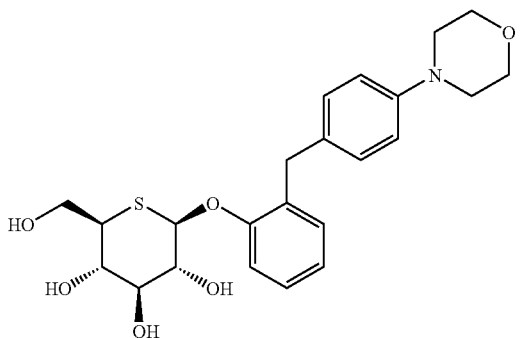 | ESI m/z = 470(M + Na)<br>mp 174.0-176.5° C. |
| Compound 74 | 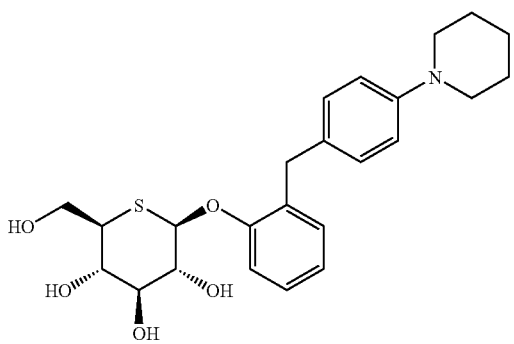 | ESI m/z = 468(M + Na)<br>mp 156.5-160.0° C. |

-continued
| Compound No. | Chemical structure | ¹NMR, MS, mp |
|---|---|---|
| Compound 75 | 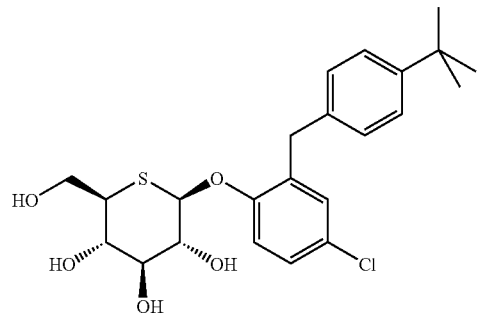 | ESI m/z = 475, 477(M + Na)<br>mp 79.0-82.5° C. |
| Compound 76 | 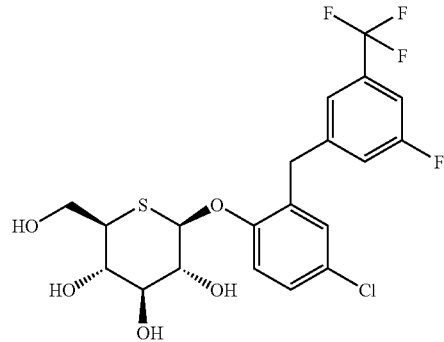 | ESI m/z = 505, 507(M + Na)<br>mp 126.0-129.0° C. |
| Compound 77 | 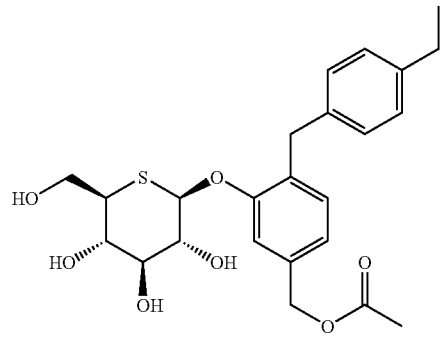 | mp 158.0-160.0° C. |
| Compound 78 | 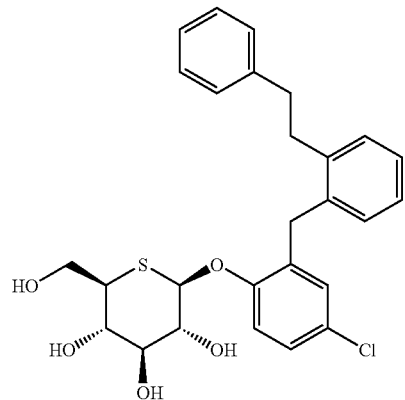 | ESI m/z = 523, 525(M + Na)<br>mp 128.0-130.0° C. |

-continued
| Compound No. | Chemical structure | ¹NMR, MS, mp |
|---|---|---|
| Compound 79 | 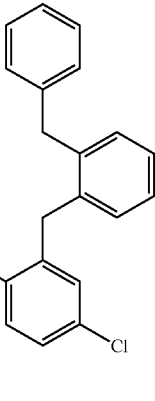 | ESI m/z = 509, 511(M + Na)<br>mp 150.5-151.5° C. |
| Compound 80 | 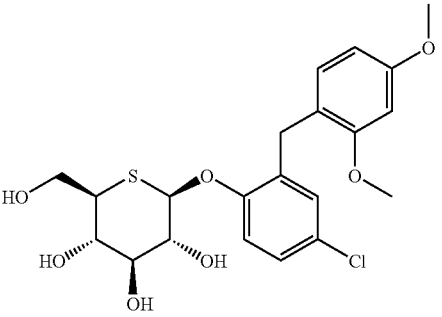 | ESI m/z = 479, 481(M + Na)<br>mp 195.5-197.0° C. |
| Compound 81 | 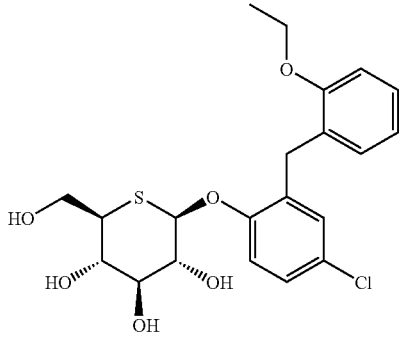 | ESI m/z = 463, 465(M + Na)<br>mp 196.5-198.5° C. |
| Compound 82 | 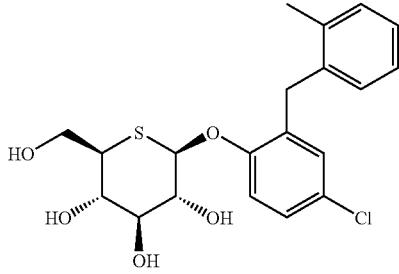 | ESI m/z = 433, 435(M + Na)<br>mp 147.0-149.0° C. |

| Compound No. | Chemical structure | ¹NMR, MS, mp |
|---|---|---|
| Compound 83 | 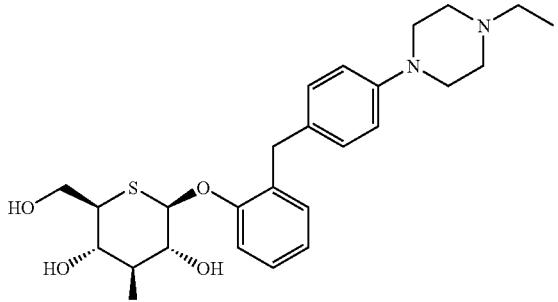 | ¹H-NMR(300MHz, CD$_3$OD): δ 1.14(t, J=7.3Hz, 3H), 2.49(q, J=7.3Hz, 2H), 2.62-2.65(m, 4H), 2.90(ddd, J=3.6, 6.2, 10.1Hz, 1H), 3.13-3.16(m, 4H), 3.57(dd, J=9.0, 10.1Hz, 1H), 3.76(dd, J=6.2, 11.5Hz, 1H), 3.81(t, J=8.7Hz, 1H), 3.86-3.96(m, 3H), 5.16(d, J=8.7Hz, 1H), 6.87-6.93(m, 3H), 7.02-7.19(m, 4H), 7.26(d, J=7.8Hz, 2H).<br>ESI m/z = 497(M + Na). |
| Compound 84 | 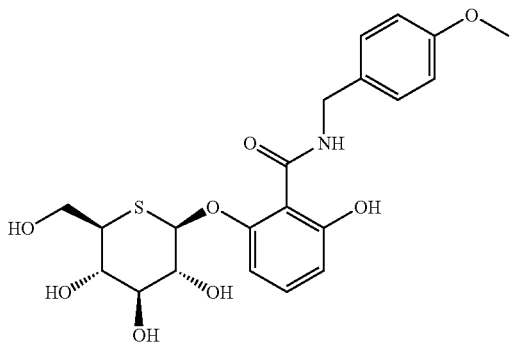 | ESI m/z = 474(M + Na)<br>mp 183.0-185.0° C. |
| Compound 85 | 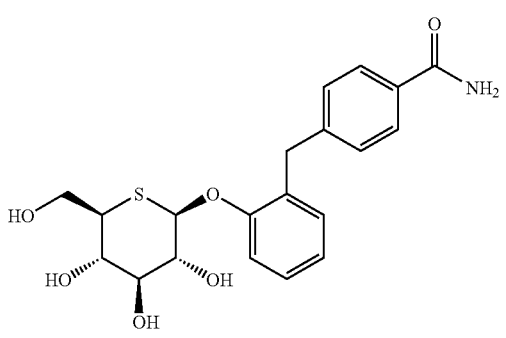 | ESI m/z = 428(M + Na)<br>mp 215.5-216.0° C. |
| Compound 86 | 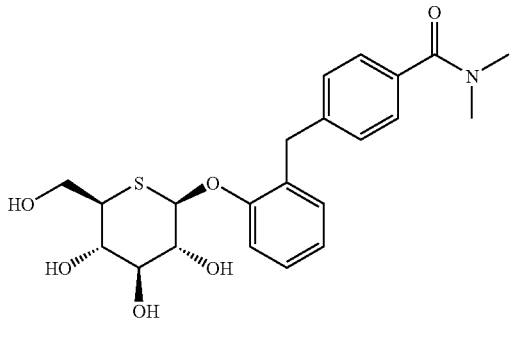 | ESI m/z = 458(M + Na)<br>mp 193.5-194.0° C. |

-continued

| Compound No. | Chemical structure | ¹NMR, MS, mp |
|---|---|---|
| Compound 87 | 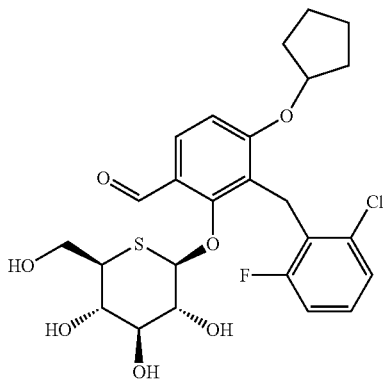 | ¹H-NMR(300MHz, CD3OD): δ 1.25-1.51(m, 8H), 2.78-2.95(m, 1H), 3.26(t, J=9.0Hz, 1H), 3.52-4.00(m, 4H), 4.28(d, J=15.0Hz, 1H), 4.35(d, J=15.0Hz, 1H), 5.10(d, J=9.0Hz, 1H), 6.82-6.99(m, 2H), 7.08-7.19(m, 2H), 7.76(d, J=8.7Hz, 2H), 10.37(s, 1H).<br>ESI m/z = 549, 551(M + Na) |
| Compound 88 | 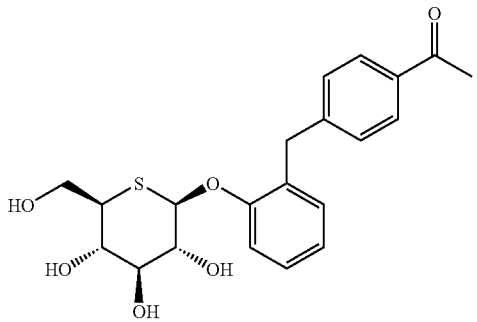 | ¹H-NMR(300MHz, CD3OD): δ 2.56(s, 3H), 2.91 (ddd, J=3.7, 6.2, 10.1Hz, 1H), 3.55(dd, J=9.0, 10.1Hz, 1H), 3.75(dd, J=6.2, 11.5Hz, 1H), 3.79 (dd, J=8.7, 9.0Hz, 1H), 3.91(dd, J=3.7, 11.5Hz, 1H), 4.02(d, J=14.8Hz, 1H), 4.15(d, J=14.8 Hz, 1H), 5.19(d, J=8.7Hz, 1H), 6.94(m, 1H), 7.10(m, 1H), 7.20(m, 1H), 7.20(m, 1H), 7.35(m, $J_{AB}$ = 8.7Hz, 2H), 7.88(m, $J_{AB}$ = 8.7Hz, 2H).<br>ESI m/z = 427(M + Na) |
| Compound 89 | 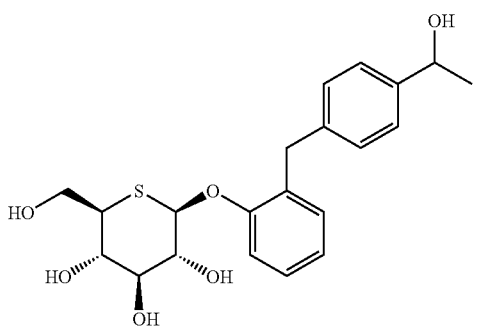 | ¹H-NMR(300MHz, CD3OD): δ 1.40(d, J=6.5 Hz, 3H), 2.94(ddd, J=3.7, 6.2, 10.1Hz, 1H), 3.56 (dd, J=9.0, 10.1Hz, 1H), 3.77(dd, J=6.2, 11.3Hz, 1H), 3.80(t, J=8.9Hz, 1H), 3.90(dd, J=3.7, 11.3Hz, 1H), 3.95(d, J=15.2Hz, 1H), 4.03(d, J=15.2Hz, 1H), 5.17(d, J=8.7Hz, 1H), 6.90(m, 1H), 7.04(m, 1H), 7.14-7.29(m, 6H).<br>ESI m/z = 429(M + Na) |
| Compound 90 | 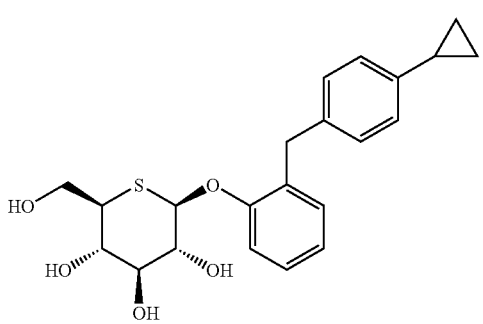 | ESI m/z = 425(M + Na)<br>mp 148.0-148.5° C. |

| Compound No. | Chemical structure | $^1$NMR, MS, mp |
|---|---|---|
| Compound 91 | 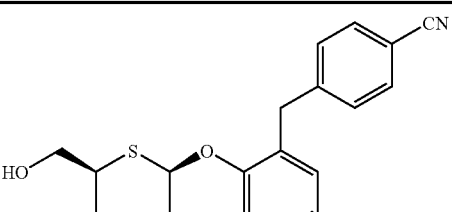 | $^1$H-NMR(300MHz, CD3OD): δ 2.91(ddd, J= 3.7, 6.2, 10.3Hz, 1H), 3.55(dd, J=8.9, 10.3Hz, 1H), 3.75(dd, J=6.1, 11.5Hz, 1H), 3.77(t, J= 8.9Hz, 1H), 3.91(dd, J=3.7, 11.5Hz, 1H), 4.02(d, J=14.9Hz, 1H), 4.16(d, J=14.9Hz, 1H), 5.20(d, J=8.9Hz, 1H), 6.95(m, 1H), 7.13(m, 1H), 7.22(m, 1H), 7.30(m, 1H), 7.41(m, $J_{AB}$ = 8.7Hz, 2H), 7.59(m, $J_{AB}$ = 8.7Hz, 2H).<br>ESI m/z = 410(M + Na) |
| Compound 92 | 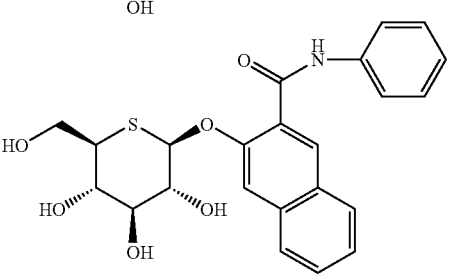 | ESI m/z = 464(M + Na)<br>mp 200.0-202.0° C. |

TEST EXAMPLE

According to the reported procedure (Aanal. Biochem., vol. 201, p. 301, 1984), a suspension of rat renal brush border membrane vehicles (BBMVs) was prepared (protein concentration: 4 mg/mL). This suspension (50 μL) was pre-incubated at 37° C. for 2 minutes, followed by addition of 150 μL reaction solution containing a test compound dissolved in DMSO (final DMSO content: 1%) as well as 100 mM mannitol, 100 mM NaSCN or KSCN, 10 mM HEPES/Tris (pH 7.4), D-glucose (final concentration: 0.1 mM) and 1 μCi D-[6-$^3$H]glucose (Amersham). After reaction at 37° C. for 5 seconds, 1 mL ice-cold reaction stop solution (150 mM NaCl, 10 mM HEPES/Tris (pH 7.4), 0.3 mM phloridzin) was added to the reaction mixture to stop the reaction. The reaction mixture was immediately filtered by rapid filtration using a membrane filter (pore size: 0.45 μm, HAWP02500, Millipore) to separate BBMVs. This membrane filter was washed three times with 4.5 mL ice-cold reaction stop solution, dried sufficiently and then assayed for radioactivity using a liquid scintillation counter (Beckman) to determine the amount of glucose trapped inside the BBMVs on the membrane filter.

Assuming that the amount of trapped glucose in the absence of a test compound was set to 100%, the concentration required for the test compound to cause 50% inhibition of the amount of trapped glucose was calculated ($IC_{50}$ value).

The results obtained were shown in Table 2 below.

TABLE 2

| Compound | $IC_{50}$ (μM) |
|---|---|
| Compound 1 | 0.20 |
| Compound 2 | 0.39 |
| Compound 3 | 0.38 |
| Compound 4 | 0.56 |
| Compound 5 | 0.48 |
| Compound 6 | 0.62 |
| Compound 7 | 0.35 |
| Compound 8 | 0.38 |
| Compound 9 | 0.16 |
| Compound 10 | 2.40 |

INDUSTRIAL APPLICABILITY

The present invention enables the provision of 5-thio-β-D-glucopyranoside compounds or pharmaceutically acceptable salts thereof which have an excellent inhibitory effect on SGLT2 activity. The compounds of the present invention are effective as prophylactic or therapeutic agents for diabetes, diabetes-related diseases or diabetic complications.

The invention claimed is:

1. A 5-thio-β-D-glucopyranoside compound of the following formula or a pharmaceutically acceptable salt thereof or a hydrate thereof:

(i)

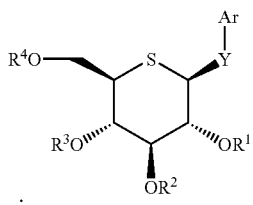

wherein
Y represents —O— or —NH—,
$R^1$, $R^2$, $R^3$ and $R^4$, which may be the same or different, each represent a hydrogen atom, a $C_{2-10}$ acyl group, a $C_{7-10}$ aralkyl group, a $C_{2-6}$ alkoxycarbonyl group, a $C_{1-6}$ alkoxy-$C_{2-10}$ acyl group or a $C_{1-6}$ alkoxy-$C_{2-6}$ alkoxycarbonyl group,
Ar represents an aryl group substituted with —X-$A^1$, in which the aryl group may further be substituted with the same or different 1 to 4 substituents selected from:
a halogen atom;
a hydroxyl group;
a $C_{1-6}$ alkyl group which may be substituted with 1 to 4 substituents selected from the group consisting of a halogen atom and a hydroxyl group;
a group represented by the formula:

—($CH_2$)$_m$-Q wherein m represents an integer of 0 to 4 and Q represents a formyl group, an amino group, a nitro group, a cyano group, a carboxyl group, a sulfonic acid group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N—($C_{1-6}$ alkyl)aminocarbonyl group, or an N,N-di($C_{1-6}$ alkyl)aminocarbonyl group; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group, X represents —($CH_2$)n-, —CO($CH_2$)n-, —CH(OH)($CH_2$)n-, —O—($CH_2$)n-, —CONH($CH_2$)n-, —NHCO($CH_2$)n-, wherein n represents an integer of 0 to 3, —COCH=CH—, —S— or —NH—, and $A^1$ represents an aryl group, a heteroaryl group or a 4- to 6-membered heterocycloalkyl group, each of which may be substituted with the same or different 1 to 4 substituents selected from:

a halogen atom;
a hydroxyl group;
a $C_{1-6}$ alkyl group which may be substituted with 1 to 4 substituents selected from the group consisting of a halogen atom and a hydroxyl group;
a group represented by the formula:

—($CH_2$)m'-Q' wherein m' represents an integer of 0 to 4 and Q' represents a formyl group, an amino group, a nitro group, a cyano group, a carboxyl group, a sulfonic acid group, a $C_{1-6}$ alkoxy group which may be substituted with 1 to 4 substituents selected from the group consisting of a halogen atom and a hydroxyl group, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N—($C_{1-6}$ alkyl)aminocarbonyl group, or an N,N-di($C_{1-6}$ alkyl)aminocarbonyl group; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group.

2. A 5-thio-β-D-glucopyranoside compound of the following formula or a pharmaceutically acceptable salt thereof or a hydrate thereof:

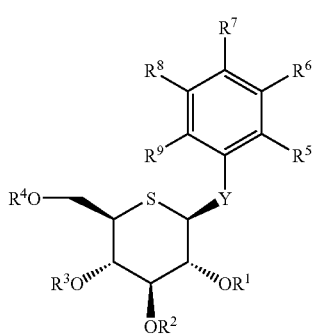

(I)

wherein
Y represents —O— or —NH—,
$R^1$, $R^2$, $R^3$ and $R^4$, which may be the same or different, each represent a hydrogen atom, a $C_{2-10}$ acyl group, a $C_{7-10}$ aralkyl group, a $C_{2-6}$ alkoxycarbonyl group, a $C_{1-6}$ alkoxy-$C_{2-10}$ acyl group or a $C_{1-6}$ alkoxy-$C_{2-6}$ alkoxycarbonyl group, and at least one of $R^5$, $R^6$, $R^7$, $R^8$ and $R^9$ represents —X-$A^1$ and the other, which may be the same or different, each represent:

a hydrogen atom;
a halogen atom;
a hydroxyl group;
a $C_{1-6}$ alkyl group which may be substituted with 1 to 4 substituents selected from the group consisting of a halogen atom and a hydroxyl group;
a group represented by the formula:

—($CH_2$)m-Q wherein m represents an integer of 0 to 4 and Q represents a formyl group, an amino group, a nitro group, a cyano group, a carboxyl group, a sulfonic acid group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N—($C_{1-6}$ alkyl)aminocarbonyl group, or an N,N-di($C_{1-6}$ alkyl)aminocarbonyl group; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group, X represents —($CH_2$)n-, —CO($CH_2$)n-, —CH(OH)($CH_2$)n-, —O—($CH_2$)n-, —CONH($CH_2$)n-, —NHCO($CH_2$)n-, wherein n represents an integer of 0 to 3, —COCH=CH—, —S— or —NH—, and $A^1$ represents an aryl group, a heteroaryl group or a 4- to 6-membered heterocycloalkyl group, each of which may be substituted with the same or different 1 to 4 substituents selected from:

a halogen atom;
a hydroxyl group;
a $C_{1-6}$ alkyl group which may be substituted with 1 to 4 substituents selected from the group consisting of a halogen atom and a hydroxyl group;
a group represented by the formula:

—($CH_2$)m'-Q' wherein m' represents an integer of 0 to 4 and Q' represents a formyl group, an amino group, a nitro group, a cyano group, a carboxyl group, a sulfonic acid group, a $C_{1-6}$ alkoxy group which may be substituted with 1 to 4 substituents selected from the group consisting of a halogen atom and a hydroxyl group, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N—($C_{1-6}$ alkyl)aminocarbonyl group, or an N,N-di($C_{1-6}$ alkyl)aminocarbonyl group; or a $C_{3-7}$ cycloalkyl group, a $C_{3-7}$ cycloalkyloxy group, an aryl group, a $C_{7-10}$ aralkyl group, an aryloxy group, a C$_{7-10}$ aralkyloxy group, a C$_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a C$_{1-6}$ alkyl group and a C$_{1-6}$ alkoxy group.

3. The 5-thio-β-D-glucopyranoside compound according to claim 2, wherein Y is —O—, or a pharmaceutically acceptable salt thereof or a hydrate thereof.

4. The 5-thio-β-D-glucopyranoside compound according to claim 2, wherein R$^5$ is —X-A$^1$, or a pharmaceutically acceptable salt thereof or a hydrate thereof.

5. The 5-thio-β-D-glucopyranoside compound according to claim 4, wherein X is —(CH$_2$)n-, wherein n represents an integer of 0 to 3, or a pharmaceutically acceptable salt thereof or a hydrate thereof.

6. The 5-thio-β-D-glucopyranoside compound according to claim 4, wherein X is —CO(CH$_2$)n-, wherein n represents an integer of 0 to 3, or a pharmaceutically acceptable salt thereof or a hydrate thereof.

7. A 5-thio-β-D-glucopyranoside compound of the following formula or a pharmaceutically acceptable salt thereof or a hydrate thereof:

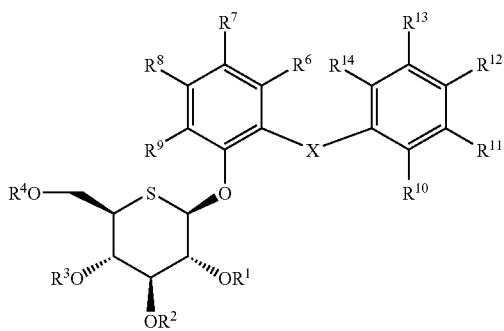

(II)

wherein
X represents —(CH$_2$)n-, —CO(CH$_2$)n-, —CH(OH)(CH$_2$)n-, —O—(CH$_2$)n-, —CONH(CH$_2$)n-, —NHCO(CH$_2$)n-, wherein n represents an integer of 0 to 3, —COCH═CH—, —S— or —NH—, R$^1$, R$^2$, R$^3$ and R$^4$, which may be the same or different, each represent a hydrogen atom, a C$_{2-10}$ acyl group, a C$_{7-10}$ aralkyl group, a C$_{2-6}$ alkoxycarbonyl group, a C$_{1-6}$ alkoxy-C$_{2-10}$ acyl group or a C$_{1-6}$ alkoxy-C$_{2-6}$ alkoxycarbonyl group, R$^6$, R$^7$, R$^8$ and R$^9$, which may be the same or different, each represent:
a hydrogen atom;
a halogen atom;
a hydroxyl group;
a C$_{1-6}$ alkyl group which may be substituted with 1 to 4 substituents selected from the group consisting of a halogen atom and a hydroxyl group;
a group represented by the formula:

—(CH$_2$)$m$-Q wherein m represents an integer of 0 to 4 and Q represents a formyl group, an amino group, a nitro group, a cyano group, a carboxyl group, a sulfonic acid group, a C$_{1-6}$ alkoxy group which may be substituted with 1 to 4 halogen atoms, a C$_{1-6}$ alkoxy-C$_{1-6}$ alkoxy group, a C$_{2-10}$ acyloxy group, a C$_{2-10}$ acyl group, a C$_{2-6}$ alkoxycarbonyl group, a C$_{1-6}$ alkylthio group, a C$_{1-6}$ alkylsulfinyl group, a C$_{1-6}$ alkylsulfonyl group, —NHC(═O)H, a C$_{2-10}$ acylamino group, a C$_{1-6}$ alkylsulfonylamino group, a C$_{1-6}$ alkylamino group, an N,N-di(C$_{1-6}$ alkyl)amino group, a carbamoyl group, an N—(C$_{1-6}$ alkyl)aminocarbonyl group, or an N,N-di(C$_{1-6}$ alkyl)aminocarbonyl group; or a C$_{3-7}$ cycloalkyl group, a C$_{3-7}$ cycloalkyloxy group, an aryl group, a C$_{7-10}$ aralkyl group, an aryloxy group, a C$_{7-10}$ aralkyloxy group, a C$_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a C$_{1-6}$ alkyl group and a C$_{1-6}$ alkoxy group, and R$^{10}$, R$^{11}$, R$^{12}$, R$^{13}$ and R$^{14}$, which may be the same or different, each represent:
a hydrogen atom;
a halogen atom;
a hydroxyl group;
a C$_{1-6}$ alkyl group which may be substituted with 1 to 4 substituents selected from the group consisting of a halogen atom and a hydroxyl group;
a group represented by the formula:

—(CH$_2$)$m'$-Q' wherein m' represents an integer of 0 to 4 and Q' represents a formyl group, an amino group, a nitro group, a cyano group, a carboxyl group, a sulfonic acid group, a C$_{1-6}$ alkoxy group which may be substituted with 1 to 4 halogen atoms, a C$_{1-6}$ alkoxy-C$_{1-6}$ alkoxy group, a C$_{2-10}$ acyloxy group, a C$_{2-10}$ acyl group, a C$_{2-6}$ alkoxycarbonyl group, a C$_{1-6}$ alkylthio group, a C$_{1-6}$ alkylsulfinyl group, a C$_{1-6}$ alkylsulfonyl group, —NHC(═O)H, a C$_{2-10}$ acylamino group, a C$_{1-6}$ alkylsulfonylamino group, a C$_{1-6}$ alkylamino group, an N,N-di(C$_{1-6}$ alkyl)amino group, a carbamoyl group, an N—(C$_{1-6}$ alkyl)aminocarbonyl group, or an N,N-di(C$_{1-6}$ alkyl)aminocarbonyl group; or a C$_{3-7}$ cycloalkyl group, a C$_{3-7}$ cycloalkyloxy group, an aryl group, a C$_{7-10}$ aralkyl group, an aryloxy group, a C$_{7-10}$ aralkyloxy group, a C$_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a C$_{1-6}$ alkyl group and a C$_{1-6}$ alkoxy group.

8. The 5-thio-β-D-glucopyranoside compound according to claim 7, wherein X is —CH$_2$—, or a pharmaceutically acceptable salt thereof or a hydrate thereof.

9. The 5-thio-β-D-glucopyranoside compound according to claim 7, wherein X is —O— or —NH—, or a pharmaceutically acceptable salt thereof or a hydrate thereof.

10. A 5-thio-β-D-glucopyranoside compound of the following formula or a pharmaceutically acceptable salt thereof:

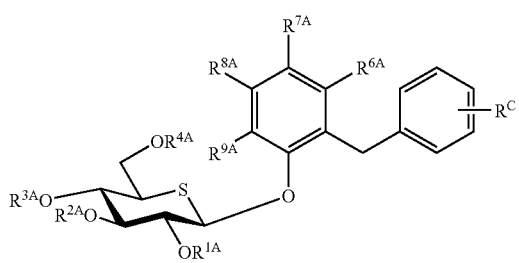

(A)

wherein R$^{6A}$ to R$^{9A}$, which may be the same or different, each represent a hydrogen atom, a halogen atom, a C$_{1-6}$ alkyl group, a C$_{1-6}$ alkoxy group, a C$_{1-6}$ alkoxy-C$_{1-6}$ alkoxy group, a carboxyl group, a C$_{2-6}$ alkoxycarbonyl group, a hydroxyl group or a hydroxy-C$_{1-4}$ alkyl group, R$^C$ represents a hydrogen atom, a halogen atom, a C$_{1-6}$ alkyl group, a C$_{1-6}$ alkoxy group, a hydroxy-$C_{1-4}$ alkyl group, a halogen-substituted $C_{1-6}$ alkyl group or a $C_{1-6}$ alkylthio group, $R^{4A}$ represents a hydrogen atom, a $C_{2-6}$ alkoxycarbonyl group or a $C_{2-6}$ alkanoyl group, and $R^{1A}$ to $R^{3A}$, which may be the same or different, each represent a hydrogen atom, a $C_{2-8}$ alkanoyl group or a benzoyl group.

11. A 5-thio-β-D-glucopyranoside compound of the following formula or a pharmaceutically acceptable salt thereof:

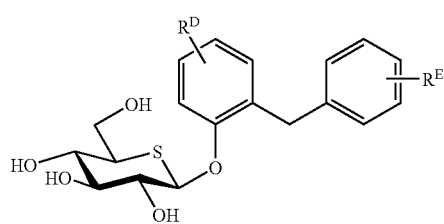

(B)

wherein $R^D$ represents a hydrogen atom, a halogen atom, a $C_{1-6}$ alkyl group or a hydroxy-$C_{1-4}$ alkyl group, and $R^E$ represents a hydrogen atom, a halogen atom, a $C_{1-6}$ alkyl group, a $C_{1-6}$ alkoxy group or a hydroxy-$C_{1-4}$ alkyl group.

12. A 5-thio-β-D-glucopyranoside compound of the following formula or a pharmaceutically acceptable salt thereof or a hydrate thereof:

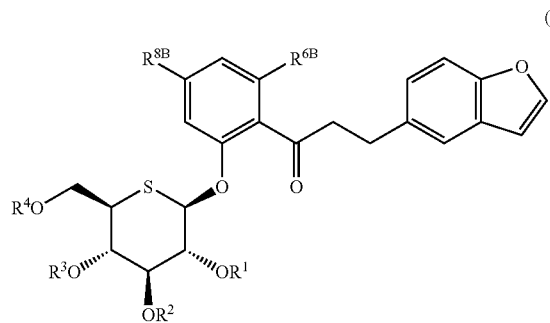

(C)

wherein $R^1$, $R^2$, $R^3$ and $R^4$, which may be the same or different, each represent a hydrogen atom, a $C_{2-10}$ acyl group, a $C_{7-10}$ aralkyl group, a $C_{2-6}$ alkoxycarbonyl group, a $C_{1-6}$ alkoxy-$C_{2-10}$ acyl group or a $C_{1-6}$ alkoxy-$C_{2-6}$ alkoxycarbonyl group, $R^{6B}$ represents a hydrogen atom, a halogen atom, a hydroxyl group, a $C_{2-10}$ acyloxy group, or a $C_{1-6}$ alkyl or $C_{1-6}$ alkoxy group which may be substituted with 1 to 4 halogen atoms, and $R^{8B}$ represents a hydrogen atom, a halogen atom or a $C_{1-6}$ alkyl group which may be substituted with 1 to 4 halogen atoms.

13. A pharmaceutical preparation, which comprises the 5-thio-β-D-glucopyranoside compound according to any one of claims 1 to 12 or a pharmaceutically acceptable salt thereof or a hydrate thereof as an active ingredient.

14. A method of treating a condition treatable by inhibiting sodium-dependent glucose transporter 2 activity said method comprising administering to a subject in need of treatment a pharmaceutically effective amount of the 5-thio-β-D-glucopyranoside compound according to claim 1, a pharmaceutically acceptable salt thereof or a hydrate thereof.

15. The method according to claim 14, wherein the condition is diabetes, diabetes-related diseases or diabetic complications.

16. A pharmaceutical preparation, which comprises the 5-thio-β-D-glucopyranoside compound according to any one of claims 1 to 12 or a pharmaceutically acceptable salt thereof or a hydrate thereof, in combination with at least one drug selected from the group consisting of an insulin sensitizer selected from the group consisting of a PPARγ agonist; a PPARα/γ agonist; a PPARδ agonist; and a PPARα/γ/δ agonist, a glycosidase inhibitor, a biguanide, an insulin secretagogue, an insulin formulation and a dipeptidyl peptidase IV inhibitor.

17. A pharmaceutical preparation, which comprises the 5-thio-β-D-glucopyranoside compound according to any one of claims 1 to 12 or a pharmaceutically acceptable salt thereof or a hydrate thereof, in combination with at least one drug selected from the group consisting of a hydroxymethylglutaryl coenzyme A reductase inhibitor, a fibrate, a squalene synthase inhibitor, an acyl-coenzyme A:cholesterol acyltransferase inhibitor, a low-density lipoprotein receptor promoter, a microsomal triglyceride transfer protein inhibitor and an anorectic.

18. A 5-thio-β-D-glucopyranoside compound of the following formula or a pharmaceutically acceptable salt thereof or a hydrate thereof:

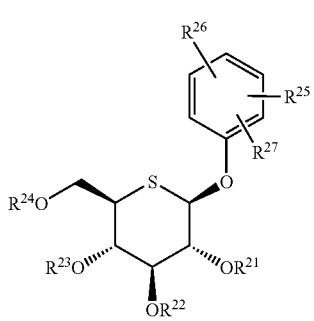

(III)

wherein
$R^{21}$, $R^{22}$, $R^{23}$ and $R^{24}$, which may be the same or different, each represent a hydrogen atom or a $C_{2-10}$ acyl group,
$R^{25}$ represents an amino group, a $C_{2-6}$ alkanoyl group, a carboxyl group, a formyl group, a $C_{2-6}$ alkoxycarbonyl group or a hydroxyl group, and
$R^{26}$ and $R^{27}$, which may be the same or different, each represent a hydrogen atom, a halogen atom, a hydroxyl group, a $C_{1-6}$ alkyl group which may be substituted with 1 to 4 substituents selected from the group consisting of a halogen atom and a hydroxyl group, or a $C_{1-6}$ alkoxy group which may be substituted with 1 to 4 halogen atoms.

* * * * *